(12) United States Patent
Brown et al.

(10) Patent No.: US 8,682,597 B2
(45) Date of Patent: Mar. 25, 2014

(54) ESTIMATING DETAILED COMPOSITIONAL INFORMATION FROM LIMITED ANALYTICAL DATA

(75) Inventors: James M. Brown, Flemington, NJ (US); Anantha Sundaram, Fairfax, VA (US); Roland B. Saeger, Runnemede, NJ (US); Helen S. Wellons, Annandale, NJ (US); Clinton R. Kennedy, West Chester, PA (US); Stephen B. Jaffe, Moorestown, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 810 days.

(21) Appl. No.: 12/287,541

(22) Filed: Oct. 10, 2008

(65) Prior Publication Data

US 2009/0105966 A1 Apr. 23, 2009

Related U.S. Application Data

(60) Provisional application No. 60/999,111, filed on Oct. 16, 2007.

(51) Int. Cl.
*G01N 31/00* (2006.01)

(52) U.S. Cl.
USPC .................................. 702/30; 702/22; 702/23

(58) Field of Classification Search
USPC .............................................. 702/22–23, 137
See application file for complete search history.

(56) References Cited

U.S. PATENT DOCUMENTS

| | | | |
|---|---|---|---|
| 3,508,047 A * | 4/1970 | Mott et al. | .................. 250/252.1 |
| 5,121,337 A | 6/1992 | Brown | |
| 5,291,422 A * | 3/1994 | Esztergar | ........................ 702/30 |
| 5,349,193 A | 9/1994 | Mott et al. | |
| 5,668,374 A * | 9/1997 | DiFoggio et al. | ........ 250/339.12 |
| 5,817,517 A | 10/1998 | Perry et al. | |
| 6,275,775 B1 | 8/2001 | Baco et al. | |
| 6,662,116 B2 | 12/2003 | Brown | |
| 7,153,688 B2 | 12/2006 | Mango | |
| 2006/0047444 A1 | 3/2006 | Brown et al. | |
| 2007/0114377 A1 | 5/2007 | Qian et al. | |

FOREIGN PATENT DOCUMENTS

WO   2006126647 A1   11/2006

OTHER PUBLICATIONS

Cover et al., "Entropy, Relative Entropy and Mutual Information", Elements of Information Theory, 1991, John Wiley & Sons, Inc., ISBN 0-471-20061-1, Chapter 2, pp. 12-49.*
Jaffe et al., "Extension of Structure-Oriented Lumping to Vacuum Resid", Ind. Eng. Chem. Res. 2005, vol. 44, No. 26, pp. 9840-9852.

(Continued)

*Primary Examiner* — Mischita Henson
(74) *Attorney, Agent, or Firm* — Ronald D. Hantman; Glenn T. Barrett

(57) ABSTRACT

A method for determining the composition of a material including the steps of fitting multivariate analytical data of the material to a combination of multivariate analytical data in a database to determine coefficients of the combination so as to determine a reference model of composition based on the coefficients and the compositions in the database, wherein the database includes multivariate analytical data of database materials whose compositions are known, and reconciling the reference model of composition to match properties of the material.

24 Claims, 37 Drawing Sheets

(56) References Cited

OTHER PUBLICATIONS

Quann et al., "Structure-Oriented Lumping: Describing the Chemistry of Complex Hydrocarbon Mixtures", Ind. Eng. Chem. Res. 1992, vol. 31, No. 11, pp. 2483-2497.

Ghosh et al., "Detailed Composition-Based Model for Predicting the Cetane Number of Diesel Fuels", Ind. Eng. Chem. Res. 2006, vol. 45, No. 1, pp. 346-351.

Quann et al., "Development of a Detailed Gasoline Composition-Based Octane Model", Ind. Eng. Chem. Res. 2006, vol. 45, No. 1, pp. 337-345.

Quann et al., "Building Useful Models of Complex Reaction Systems in Petroleum Refining", Chemical Engineering Society, 1996, vol. 51, No. 10, pp. 1615-1635.

Singapore Search Report issued Nov. 16, 2012 in corresponding Singapore Application No. 201102857-8, 7 pgs.

Singapore Written Opinion issued Nov. 16, 2012 in corresponding Singapore Application No. 201102857-8, 10 pgs.

* cited by examiner

Benzenes (X=-6)
| | alkyl carbons | MW |
|---|---|---|
| ⬡ | 0 | 78 |
Naphthalenes (X=2)
| | alkyl carbons | MW |
|---|---|---|
| ⬡⬡ | 0 | 128 |
Fluorenes (X=-2)
| | alkyl carbons | MW |
|---|---|---|
| ⬡▽⬡ | 0 | 166 |
Dibenzothiophenes (X=2)
| | alkyl carbons | MW |
|---|---|---|
| ⬡S⬡ | 0 | 184 |
FIG. 34
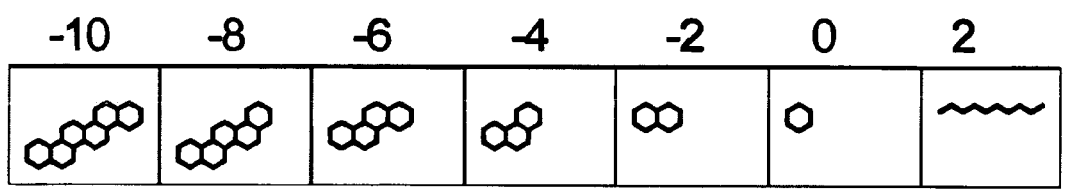
FIG. 35
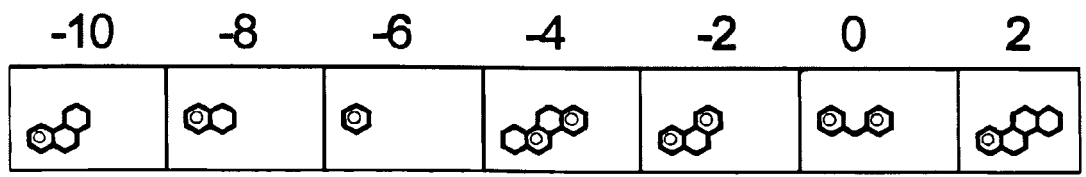
FIG. 36
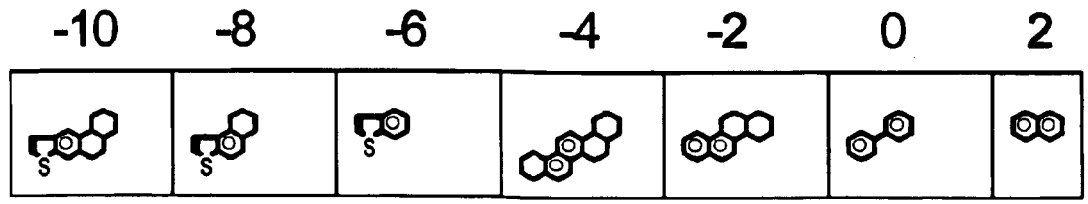
FIG. 37

ESTIMATING DETAILED COMPOSITIONAL INFORMATION FROM LIMITED ANALYTICAL DATA

This application claims the benefit of U.S. Provisional Application 60/999,111 filed Oct. 16, 2007.

BACKGROUND OF THE INVENTION

The present invention is a method to determine a detailed model of composition of a crude oil, a crude oil distillate, or a petroleum process stream. The successful development of the technology described herein will reduce the need for detailed analytical analysis, e.g. high-detail hydrocarbon analysis (HDHA) of refinery feeds, intermediate streams and products, and will enhance the utility of Real Time Optimization (RTO) and Optimizable Refinery Models (ORMs) by allowing more frequent (easier, cheaper, faster) analysis of actual feedstocks and products.

Perry and Brown (U.S. Pat. No. 5,817,517) demonstrated the use of FT-IR to estimate constituent classes of molecules (e.g. "lumps") in streams such as feeds to catalytic cracking units. This method does not provide the detailed compositional information of the current invention.

High-Detailed Hydrocarbon Analysis (HDHA) is an analytical protocol for measuring a detailed hydrocarbon composition of a crude oil or crude distillate or petroleum process stream. The acronym HDHA is also used for the Model of Composition produced by this analysis. The specific analytical protocol and the molecular information contained in the HDHA depend on the boiling range of the material being analyzed.

- For a naphtha stream boiling below approximately 350° F., a detailed analysis can be accomplished via gas chromatography using methods such as ASTM D 5134, D 5443, and D 6729, D 6730 or other similar methods. These analyses provide complete molecular descriptions, distinguishing among isomers.
- For a kerosene stream with a nominal boiling range of 350° F.-550° F., a detailed analysis can be accomplished using the method of Qian, et. al. (US 2007/0114377 A1) This analysis distinguishes among the molecular types in the kerosene, but does not discern exact molecular (isomeric) structure.
- An analytical protocol for analyzing gas oil materials boiling between approximately 550° F. and 1050° F. is described below in Appendices A-C. This heavy HDHA (H-HDHA) is a complex protocol involving various chromatographic separations followed by elemental and mass spectral analyses of separated fractions. Again, this analysis distinguishes among molecular types but not among isomers.
- For vacuum resid materials boiling above 1050° F., individual molecules cannot be measured for the entire boiling range. Jaffe, Freund and Olmstead (Extension of Structure-Oriented Lumping to Vacuum Residua, Jaffe, Stephen B.; Freund, Howard; Olmstead, William N.; *Ind. Eng. Chem. Res.* V 44, p. 9840-9852, 2005.) described how molecular compositions can be inferred by extrapolating the gas oil compositions so as to be consistent with other measurements such as elemental analysis (C, H, S, N, O, Ni and V), average molecular weight, Nuclear Magnetic Resonance (NMR), infrared (IR), ultra-violet visible (UV-visible) spectroscopy and separation techniques such as short path distillation, high performance liquid chromatography (HPLC), gas chromatography (GC) and solvent solubility.

For wider boiling materials such as crude oils, the HDHA analysis requires that the total material be distilled into naphtha, kerosene, gas oil and resid fractions which are separately analyzed via the protocols discussed above. The distillation can be accomplished via methods such as ASTM D 2892 and D 1160. The data for the individual cuts is then combined into a complete description of the wider boiling material.

HDHA compositions are currently measured on different process streams. These detailed compositions are used in the development of SOL-based refinery process models (see R. J. Quann and S. B. Jaffe (*Ind. Eng. Chem. Res.* 1992, 31, 2483-2497 and Quann, R. J.; Jaffe, S.B. *Chemical Engineering Science* v51 n 10 pt A May 1996. p 1615-1635, 1996), and serve as a reference "template" of typical stream compositions. The HDHA method, while giving detailed results, is also elaborate and expensive, and is not suited for on-line implementation. Therefore, when composition of a sample is required for use in process control or optimization, synthesis techniques (step 2 of the current invention) are typically used to adjust a fixed reference template selected based on prior experience to match measured property targets such as API and boiling curve. However, systematic reference selection techniques do not exist and the quality of the eventually estimated composition crucially depends upon the reference. Estimating composition from properties can be difficult to impossible if poor judgment and criteria are used to select the reference. Availability of a whole sample, multivariate analytical techniques such as FTIR, supply a crucial piece of the composition puzzle that can be used to construct this critical "reference" composition. Brown (U.S. Pat. No. 6,662,116 B2) has described the use of FTIR measurements and a "Virtual Assay" analysis methodology for estimating for crude assay information. This analysis methodology can be used to estimate HDHA data, but the resultant composition estimates may not adequately match measured property values. The estimated compositions, however, are often superior references for the synthesis of an accurate detailed composition.

SUMMARY OF THE INVENTION

Petroleum streams are complex mixtures of hydrocarbons containing enormous numbers of distinct molecular species. These streams include any hydrocarbon stream from processes that change petroleum's molecular composition. The streams are so complex, and have so many distinct molecular species that any molecular approximation of the composition is essentially a model, that is, a model-of-composition (MoC)

The present invention provides a method for estimating the detailed model-of-composition of an unknown material. The estimation method involves two steps. The first step uses a multivariate analytical technique such as spectroscopy, or a combination of a multivariate technique and sample property-analysis, (e.g. spectroscopy plus API, elemental data, viscosity and/or boiling curve), to construct an initial estimate of composition, e.g. a template composition called "the reference". In the second step, this reference composition is refined through an optimization algorithm to adjust the template composition to match a set of additional analytical data or properties called "targets" (e.g. a distillation or simulated distillation curve) so as to provide a self-consistent model of composition for the unknown material. The specific targets used in the second step may be sample type dependent, and they may vary depending on the ultimate use of the composition data. The algorithm in the second step minimally modifies the reference composition to preserve the underlying molecular signature while attaining the target values. This latter use of a regression algorithm to adjust the reference composition so that it matches known property targets is referred to as "synthesis" or "tuning". The validity of this method is supported by examples where the initial reference is close to the measured composition and examples where the initial reference is far from the measured composition.

Petroleum is a complex mixture containing thousands of distinct hydrocarbon species including paraffins, cyclic paraffins, multi-ring aromatics, and various heteroatomic hydrocarbons (most commonly containing O, S, and N). Virgin petroleum crude oils contain molecules of a wide boiling point range from highly volatile $C_4$ hydrocarbons to nonvolatile asphaltenes. Detailed compositional analysis of petroleum is critical for determining the quality of petroleum feedstreams, for determining the suitability of feedstreams for use in the manufacture of desired products, for developing process and refinery models, and for controlling and optimizing refining processes. Unfortunately, the measurement of detailed compositional data has traditionally been both time consuming and expensive, and such detailed composition data was seldom available in timely fashion for decision making, control or optimization. The current invention uses spectroscopy in combination with a few relatively inexpensive and rapid property analyses to provide detailed estimates of composition on a time frame suitable for decision making, control and optimization.

Spectroscopy has been employed for compositional analysis of petroleum, but such applications have been largely limited to analyses of naphtha range materials where the number of molecular species is more limited, or to the analysis of heavier feeds in terms of molecular lumps—groups of molecules based on functional similarities. The use of spectroscopy to perform step 1 of the current invention on crude oils has been previously described by Brown (U.S. Pat. No. 6,662,116 B2). Brown does not discuss the combination of the spectroscopic analysis with synthesis (step 2 of the present invention) to provide an improved estimate of composition.

Currently, for petroleum process modeling, control and optimization, a less detailed molecular lumping scheme may be employed so that the limited composition may be estimated based on fewer, quicker and less expensive measurements. Alternatively, a detailed composition may be estimated once, and the composition is assumed to be sufficiently constant to allow the use of this fixed detailed composition in modeling, control and optimization. Step 2 of the present invention can be used to adjust this fixed detailed composition to match property measurement data. The present invention provides maximum benefit over current practices in instances where the stream being analyzed varies widely over time, or where there is insufficient information to establish a suitable reference for Step 2.

BRIEF DESCRIPTION OF THE DRAWINGS

FIG. 34 shows sample homologous series core structures.

FIG. 35 shows saturate cores.
FIG. 36 shows 1-ring aromatic cores.
FIG. 37 shows 2-ring aromatic cores.

DETAILED DESCRIPTION OF THE PREFERRED EMBODIMENTS

Petroleum mixtures are made up of an exceedingly large number of individual molecular components. These streams are so complex, and have so many distinct molecular species that any molecular approximation of the composition is essentially a model, i.e. a model-of-composition. Such a model-of-composition is used to simulate the physical and chemical transformations that occur in refinery processes, and to estimate the properties of the various petroleum feed and product streams. Analytical methods for approximating the detailed compositional profile of petroleum mixtures as a large, but finite, number of components already exist. For instance, High Detailed Hydrocarbon Analysis (HDHA) is a protocol used in ExxonMobil to represent complex petroleum mixtures as an internally consistent set of components. The HDHA protocol for a petroleum mixture yields a model-of-composition. Process and product property models (see for example Ghosh, P., Hickey, K. J., Jaffe, S. B., "Development of a Detailed Gasoline Composition-Based Octane Model", *Ind. Eng. Chem. Res.* 2006, 45, 227-345 and Ghosh, P., Jaffe, S. B., "Detailed Composition-Based Model for Predicting the Cetane Number of Diesel Fuels", Ind. Eng. Chem. Res. 2006, 45, 346-351.) built on this model of composition are used in a large number of engineering and business applications such as plant optimization, raw materials acquisition and process troubleshooting. Several of these stream properties are computed from correlations in which molecular-lump property densities take simple blending rules (e.g. linear) with respect to their wt % abundances in a stream's model-of-composition (see Section on Property Correlations below). However, development of detailed crude oil and plant stream analytical data to support these activities can be time consuming and expensive. The ability to estimate such compositions quickly and cheaply from limited amounts of measurements on any given sample would enhance the applicability and utility of these applications, reduce associated costs, and reduce R&D cycle times significantly. It would also facilitate development of on-line composition inference protocols that could be used to improve applications such as Real Time Optimization (RTO), and may have applicability to on-line blending.

Figure 1:
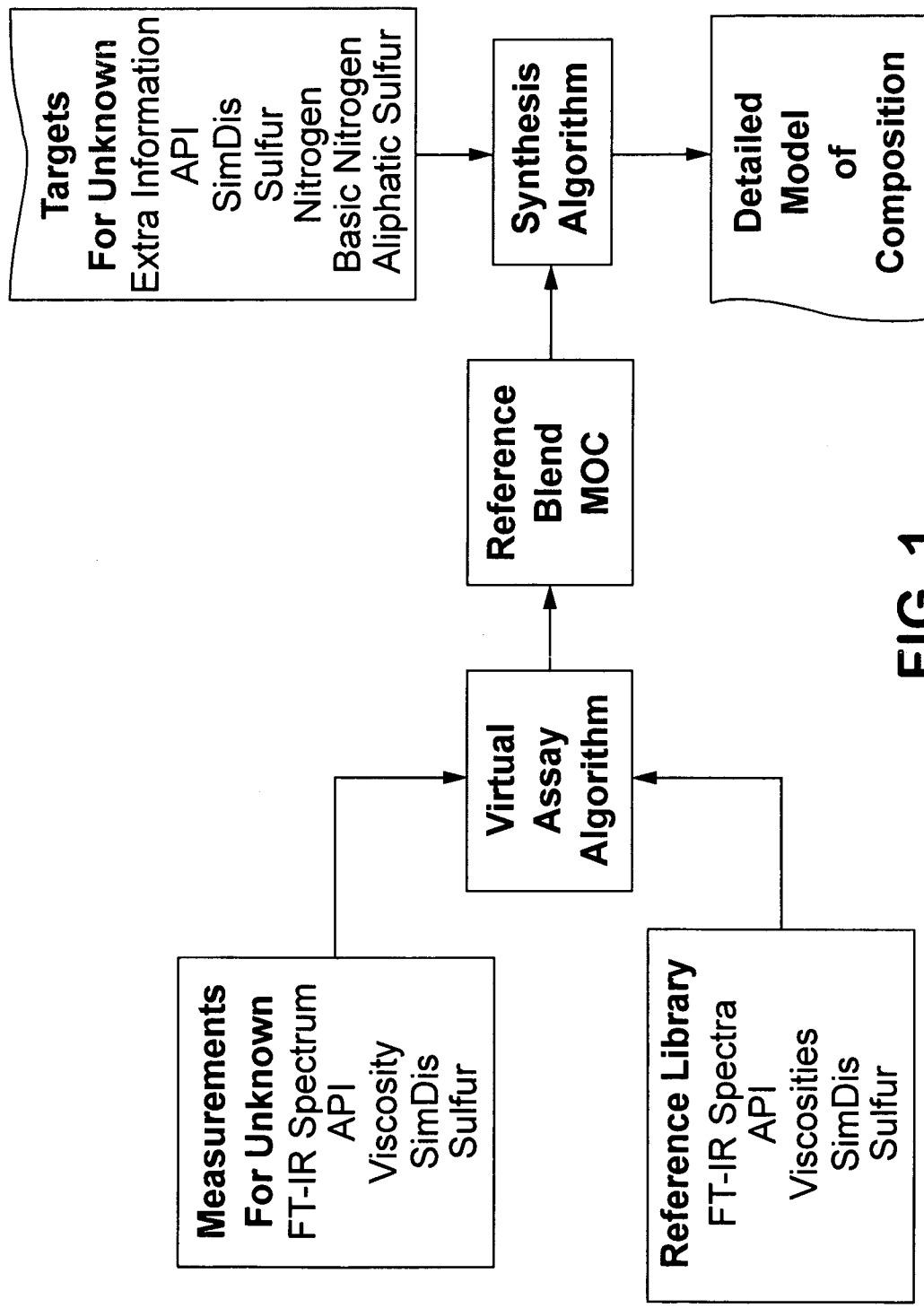
FIG. 1 shows a schematic diagram of the procedure of the invention described herein.

The current invention provides a more rapid and less expensive means of estimating a detailed composition for a crude oil or petroleum mixture in two steps. In the first step, a "reference" or "template" composition is estimated from multivariate analytical data alone, or in combination with a small set of measured properties using the method of Brown. In the second step, this reference composition is refined to match a set of measured properties using an optimization algorithm referred to as "synthesis" or "tuning". We have found that this "reference" (or "template") composition (defined in terms of a specified model of composition) of an unknown petroleum crude or fraction, can be obtained through the use of (1) multivariate analytical techniques such as FTIR alone, or in combination with a small set of appropriately chosen property measurements of the sample whose composition is sought, (2) a library (database) of similar samples that have measured multivariate analytical data (FTIR), measured HDHA and measured properties and (3) an optimization algorithm as described by Brown which constructs the reference composition for the sample as a blend of similar samples in the library so that the multivariate (FTIR) and property data for the blend is consistent with the multivariate (FTIR) data and property made on that sample. The synthesis algorithm is then applied to adjust the reference composition to meet known properties of the unknown sample. The different steps of this procedure are illustrated schematically in FIG. 1.

The property measurements used in steps 1 and 2 may include but are not limited to API gravity, viscosity, distillation or simulated (GC) distillation (SimDis, for instance ASTM D 2887), sulfur content, nitrogen content, aliphatic sulfur content, and basic nitrogen content. The properties used in step 1 may be the same or different from those used in step 2.

Step 1: Estimating the "Reference" Composition

Brown (U.S. Pat. No. 6,662,116 B2 and US 2006/0047444 A1) described how an unknown crude oil can be analyzed as a blend on known crude oils based on fitting the FT-IR spectrum of the unknown alone, or in combination with inspections such as API gravity and viscosity as a linear combination of spectra and inspections of reference crudes. This method is used to estimate assay data for the unknown crude based on the calculated blend and the assay data of the reference crudes. Similarly, this method can be used to estimate a reference HDHA for the unknown crude based on the calculated blend and the measured HDHA of the reference crudes. The method can also be employed for analysis of petroleum feed and product streams. In Step 2, this reference HDHA can then be tuned to measured assay properties to yield an accurate estimate of the detailed composition of the unknown crude/stream.

If the FT-IR spectrum is used alone, then the analysis involves the minimization of the difference between the FT-IR spectrum of the unknown and that calculated as the linear combination of the FT-IR spectra of the blend of the reference crudes.

$$\min((\hat{x}_u - x_u)^T (\hat{x}_u - x_u)) \quad [1a]$$

$$\hat{x}_u = Xc_u \quad [1b]$$

$x_u$ is a column vector containing the FT-IR for the unknown crude, and X is the matrix of FT-IR spectra of the reference crudes. The FT-IR spectra are measured on a constant volume of crude oil, so they are blended on a volumetric basis. Both $x_u$ and X are orthogonalized to corrections (baseline polynomials, water vapor spectra, and liquid water spectra) as described in U.S. Pat. No. 6,662,116 B2.

To ensure that the composition calculated is non-negative, the minimization is conveniently done using a non-negative least squares. The analysis provides coefficients for a linear combination of the reference crudes that most closely matches (in a least squares sense) the spectrum of the unknown crude.

U.S. Pat. No. 6,662,116 and US 2006/0047444 A1 also describes an analysis of crude oil based on FT-IR data augmented with API Gravity and kinematic viscosity. The algorithm attempts to minimize the difference between the data for the unknown crude and that calculated for a blend of reference crudes using [2]

$$\min \left( \left\| \begin{bmatrix} \hat{x}_u \\ w_{API}\hat{\lambda}_u(API) \\ w_{Visc}\hat{\lambda}_u(Visc) \end{bmatrix} - \begin{bmatrix} x_u \\ w_{API}\lambda_u(API) \\ w_{Visc}\lambda_u(Visc) \end{bmatrix} \right\|^T \right) \quad [2a]$$

$$\hat{x}_u = Xc_u, \hat{\lambda}_u(API) = \Lambda_{(API)}c_u, \text{ and } \hat{\lambda}_u(visc) = \Lambda_{(visc)}c_u \quad [2b]$$

$x_u$ is a column vector containing the FT-IR for the unknown crude, and X is the matrix of FT-IR spectra of the reference crudes. The FT-IR spectra are measured on a constant volume of crude oil, so they are blended on a volumetric basis. Both $x_u$ and X are orthogonalized to corrections (baseline polynomials, water vapor spectra, and liquid water spectra). $x_u$ is augmented by adding two additional elements to the bottom of the column, $w_{API}\lambda_u^{(API)}$, and $w_{Visc}\lambda_u^{(Visc)}$. $\lambda_u^{(api)}$ and $\lambda_u^{(visc)}$ are the volumetrically blend-able versions of the API gravity (i.e. specific gravity) and viscosity for the unknown, and $\Lambda_{(API)}$ and $\Lambda_{(visc)}$ are the corresponding volumetrically blend-able inspections for the reference crudes. $w_{API}$ and $w_{visc}$ are the weighting factors for the two inspections. The $\hat{x}_u$ and $\hat{\lambda}_u$ values are the estimates of the spectrum and inspections based on the calculated linear combination with coefficients $c_u$. The linear combination is preferably calculated using a nonnegative least squares algorithm. The weights, w, in [2] have the form [3].

$$w = \frac{2.77 \cdot \alpha \cdot \varepsilon}{R}. \quad [3]$$

R is the reproducibility of the inspection data calculated at the level for the unknown being analyzed. $\varepsilon$ is the average per point variance of the corrected reference spectra in X, and is set to 0.005 for crude or intermediate stream spectra collected in a 0.2-0.25 mm cell. $\alpha$ is an adjustable parameter. $\alpha$ is chosen by an optimization procedure described below.

For analysis of kerosene and gas-oil petroleum streams using FT-IR augmented with Simulated Distillation (SimDis) data, algorithm of U.S. Pat. No. 6,662,116 was modified to allow for use of inspections including ones where there is more than one value per sample. When using three inspections, the current invention minimizes $$\min \left( \left\| \begin{bmatrix} \hat{x}_u \\ w_{API}\hat{\lambda}_u(API) \\ w_{E300}\hat{\lambda}_u(E300) \\ w_{E400}\hat{\lambda}_u(E400) \\ w_{E500}\hat{\lambda}_u(E500) \\ w_{E600}\hat{\lambda}_u(E600) \\ w_{E700}\hat{\lambda}_u(E700) \\ w_{E800}\hat{\lambda}_u(E800) \\ w_{E900}\hat{\lambda}_u(E900) \\ w_{E1000}\hat{\lambda}_u(E1000) \\ w_{Sul}\hat{\lambda}_u(Sul) \end{bmatrix} - \begin{bmatrix} x_u \\ w_{API}\lambda_u(API) \\ w_{E300}\lambda_u(E300) \\ w_{E400}\lambda_u(E400) \\ w_{E500}\lambda_u(E500) \\ w_{E600}\lambda_u(E600) \\ w_{E700}\lambda_u(E700) \\ w_{E800}\lambda_u(E800) \\ w_{E900}\lambda_u(E900) \\ w_{E1000}\lambda_u(E1000) \\ w_{Sul}\lambda_u(Sul) \end{bmatrix} \right\|^T \right) \quad [3a]$$

$$\hat{x}_u = Xc_u, \hat{\lambda}_u(API) = \Lambda_{(API)}c_u, \quad [3b]$$
$$\hat{\lambda}_u(E300) = \Lambda_{(E300)}c_u, \ldots \hat{\lambda}_u(Sul) = \Lambda_{(Sul)}c_u$$

The $\lambda_u^{(E300)}$ represents the volumetrically blend-able SimDis data. SimDis data is typically reported as temperatures for fixed weight percent off, and is thus cannot be used not directly. The SimDis data is converted to a volumetrically blend-able form in two steps: (1) the SimDis curve is interpolated using a cubic interpolation and the curve is evaluated at points spanning the temperature range of interest, for instance at 300, 400, 500, 600, 700, 800, 900 F points. and 1000° F.; if the SimDis range does not span these temperatures, the data is augmented with zeros below or 100% above to ensure proper behavior of the cubic interpolation at the endpoints. (2) the weight percent of sample evaporated at each temperature is multiplied by the sample specific gravity to give a volumetrically blend-able value. $\Lambda_{(E300)}$ is the corresponding data for the reference samples. $\hat{\lambda}_u^{(E300)}$ is the estimate of $\lambda_u^{(E300)}$ based on the linear blend with coefficients $c_u$. $\lambda_u^{(Sul)}$ is volumetrically blendable sulfur data for the unknown, generated as the weight percentage sulfur times the sample specific gravity, $\Lambda_{(Sul)}$ is the corresponding data for the reference samples, and $\hat{\lambda}_u^{(Sul)}$ is the estimate of $\Lambda_u^{(Sul)}$ based on the linear blend.

For the weighting of the SimDis data in [3a], the adjustable parameter, $\alpha$, may be set to the same value for all SimDis points. Alternatively, since the SimDis data is least accurate near the initial boiling point and final boiling point, the weights of temperatures that fall below some minimum cutoff (e.g. 5% off) or above some maximum cutoff (e.g. 95% off) for the unknown being analyzed may be set to zero so as to use only the more accurate SimDis data. The value of $\alpha$ is determined by an optimization procedure designed to maximize the accuracy of the reference HDHA. One such optimization procedure is described in Appendix D.

Once the coefficients $c_u$ for the blend are calculated, the HDHA for the unknown is estimated as the corresponding blend of the HDHAs of the reference samples. Note that if the analysis is done using a multivariate analytical technique such as FT-IR, the coefficients $c_u$ will represent volume fractions of the references in the blend. Since the HDHA data will typically be expressed on a weight or weight percentage basis, a conversion from volume to weight basis is required. If h is a vector of HDHA data for a reference sample, then h can be converted from weight fraction (or percentage) to volume fraction (or percentage) by dividing each element of h by the specific gravity of the corresponding molecule, and renormalizing the resulting vector to sum to unity (or 100%) to produce a volumetric representation of the HDHA. The volumetric vectors for the references are combined in the proportions indicated by the coefficients $c_u$ to produce a volumetric HDHA vector for the unknown. Each element of the vector is multiplied by the specific gravity of the corresponding molecule, and the vector is renormalized to sum to unity (or 100%) to produce the weight fraction (or percentage) based HDHA estimate for the unknown.

Step 2: Synthesis: Reconciling Analytical Measurements to the Model-of-Composition The second step of this invention is to reconcile analytical measurements to the model-of-composition. In particular, the model-of-composition must reproduce all measurements in the analytical protocol as closely as possible, and at the same time satisfy a set of property balances, e.g. mass and elemental composition. Often, these property balances are expressed as a system of linear equations, e.g.

$$b_j = \sum_{i=1}^{N} \alpha_{ji} w_i.$$

Here, the measured value of the property in the j-th balance is $b_j$. The density of property j in molecular lump i is $a_{ji}$. The wt % abundance of molecular lump i in the MoC is $w_i$ . . . . The property densities $a_{ji}$ are either computed directly from each lump's elemental composition, or are correlated to measurements conducted on samples of known composition.

One embodiment of this reconciliation procedure is to treat it as a constrained optimization problem: we optimize the model-of-composition's fidelity to the test results of the analytical protocol subject to the property balance constraints. Another embodiment of the reconciliation procedure is successive substitution, an iterative procedure in which the model-of-composition is adjusted to match the results of the analytical protocol in a prescribed sequence until changes in the model-of-composition between iterations fall below a prescribed tolerance.

a) Reconciliation by Constrained Optimization

In the constrained optimization embodiment, we start with a model-of-composition whose reference molecular lump weight percents $\{w_i^*\}$ exactly the results from Step 1. Next, we seek a new set of weight percents $\{w_i\}$ that are minimally different from those of the reference, yet satisfy the property balances described above. To find these weight percents, we minimize the Lagrangian L (see Denn, M. M. "Optimization by Variational Methods", Chapter 1, McGraw-Hill, NYC, 1969.), defined by:

$$L \equiv \sum_{i=1}^{N} w_i * \ln(w_i / w_i^*) + \sum_{j=1}^{NP} \lambda_j \left( b_j - \sum_{i=1}^{N} \alpha_{ji} w_j \right) \quad (4)$$

The first term in Equation (4) is the Shannon information entropy content of the model-of-composition's weight percents $\{w_i\}$ relative to that of the reference weight percents $\{w_i^*\}$ (see e.g. Cover, T. M. and J. A. Thomas, "Elements of Information Theory", p. 18. J. Wiley & Sons, 1991) $\lambda_j$ is the Lagrangian multiplier of the j-th property balance constraint. NP is the total number of property balances considered in reconciliation. N is the number of molecular lumps in the model of composition. The Lagrangian L is minimized when the following stationary conditions are satisfied:

$$\frac{\delta L}{\delta w} = 0, \frac{\partial L}{\partial \lambda_j} = 0 \text{ for } j = 1, \ldots, NP \quad (5)$$

From $\partial L/\partial \lambda_j = 0$ we recover the linear property balance equations $$b_j = \sum_{i=1}^{N} \alpha_{ji} w_j.$$

We evaluate the functional derivative $\delta L/\delta w$ using calculus of variations (see e.g. Davis, H. T., "Statistical Mechanics of Phases, Interphases and Thin Films", Chapter 12, VCH Publishers, 1996.). For the Lagrangian in Equation (6), the stationary solution is $$w_i = w_i * \exp\left( -1 + \sum_{j=1}^{NP} \alpha_{ij} \lambda_j \right) \text{ for } i = 1, \ldots, N \quad (6)$$

Next, we substitute the stationary solution (7) into the property balance equations and eliminate the unknown weight percents $\{w_i\}$:

$$\sum_{i=1}^{N} \alpha_{ji} w_i * \exp\left( -1 + \sum_{k=1}^{NP} \lambda_k \alpha_{ki} \right) = b_j \text{ for } j = 1, \ldots, NP \quad (7)$$

We solve the nonlinear algebraic equations (7) on a digital computer for the Lagrangian multipliers $\{\lambda_k\}$ using Newton's method. Once we have solved the equation system (7) for these Lagrangian multipliers, we substitute them into the stationary solution (6) and obtain the weight percents of the reconciled model-of-composition $\{w_i\}$.

In the above embodiment of the reconciliation algorithm, linear property balance equations make the Lagrangian L (see Eqn. (4)) convex; i.e. one and only set of weight percents $\{w_i\}$ both locally and globally minimize L (see Ref. (see e.g. Cover, T. M. and J. A. Thomas, "Elements of Information Theory", p. 14. J. Wiley & Sons, 1991). Thus, linear property constraint equations are preferred in the above embodiment of the reconciliation algorithm. However, nonlinear property balances constraints may be used. In this embodiment, the Lagrangian L reads $$L \equiv \sum_{i=1}^{N} w_i * \ln(w_i/w_i^*) + \sum_{j=1}^{NP} \lambda_j (b_j - A_j(\{w_i\})) \quad (7a)$$

where the property function $A_j(\{w_i\})$ is any twice-differentiable function of the molecular lump weight percents $\{w_i\}$. Examples include: nonlinear algebraic equations, or the output of any algorithm that takes the molecular lump weight percents $\{w_i\}$ as inputs. In the latter example, the first and second derivatives of the property function $A_j(\{w_i\})$ with respect to molecular lump weights $w_j$ can be approximated by finite-differences (see e.g. Numerical Analysis, Burden, R. L., J. D. Faires, A. C. Reynolds (ed.), 2nd Ed., Prindle, Weber & Schmidt (publishers), NYC, pp. 124-132).

As in the linear constraint embodiment, we recover the property balance equations $b_j = A_j(\{w_i\})$ from the stationary solution condition $\partial L/\partial \lambda_j = 0$ when imposed on the Lagrangian L shown in Eqn. (7a). Similarly, the stationary solution condition $\partial L/\partial w = 0$ reads $$w_i = w_i * \exp\left(-1 + \sum_{j=1}^{NP} \lambda_j \frac{\partial A_j}{\partial w_i}\right) \quad (7b)$$

where the unknown weight percents $\{w_i\}$ cannot be readily eliminated as unknowns, as in the linear constraint embodiment detailed above. Instead, the equation system (7b) and the property balance equations $b_j = A_j(\{w_i\})$ must be solved iteratively for both the unknown weight percents $\{w_i\}$, and the Lagrangian multipliers $\{\lambda_k\}$. Newton's method can comprise this iterative scheme if the property balance functions $A_j(\{w_i\})$ are twice-differentiable with respect to the weight percents $w_j$, (see above). However, if the property functions $A_j(\{w_i\})$ are nonlinear, the Lagrangian L shown in Eqn. (7a) may or may not be convex, and multiple solutions to the unknown weight percents $\{w_i\}$, and the Lagrangian multipliers $\{\lambda_k\}$ are possible.

b) Reconciliation by Successive Substitution

As in the constrained optimization reconciliation method described above, this embodiment of the reconciliation procedure also starts with model-of-composition whose reference molecular lump weight percents $\{w_i^*\}$ exactly the results from Step 1. Adjustments to the weight percents $\{w_i^*\}$ are done in sequence, i.e. the reconciled weight percents $\{w_i\}$ computed from the j–the property balance become the reference weight percents $\{w_i^*\}$ of the j+1-th property balance. Below we describe weight percent adjustment formulae for a scalar and distributed property targets, and the successive substitution reconciliation algorithm.

a) Scalar Property Targets

Scalar properties take a single number for the entire sample.

Simple Ratio Properties

A simple ratio property is linear in weight percents, its property density $a_{ji}$ is nonzero for selected molecules, and equals zero for others. Examples of simple ratio properties include elemental composition. For simple ratio properties, we combine the property balance with a total mass balance to obtain:

$$w_i = w_i * \frac{b_j}{\sum_{k=1}^{N} \alpha_{jk} w_k} \text{ for } \alpha_{ji} > 0 \quad (8)$$

Once we have adjusted (ratioed) the weight percents of molecules that possess the simple ratio property j, we adjust the weights of the molecules that do not possess this property:

$$w_i = w_i * \frac{100 - \sum_{\alpha_{jk}>0} w_k}{\sum_{\alpha_{jk}=0} w_k^*} \text{ for } \alpha_{ji} = 0 \quad (9)$$

Averaged Properties

Averaged properties are scalar properties whose property densities $a_{ji} \neq 0$ for all molecular lumps $i = 1, \ldots, N$. Examples of such averaged properties include API gravity, hydrogen content, octane number, and pour point. For averaged properties, the ratio method summarized in Equations 8 and 9 will not work. Instead, we have developed a factor $\phi$ that is a continuous function of the averaged property j whose target value equals $b_j$. This factor adjusts upward the weights of molecules whose property density $a_{ji}$ is less than that of the target $b_j$, and it adjusts downward the weights of molecules whose property density $a_{ji}$ is greater than the target value $b_j$. The net result is to shift the distribution of weights $\{w_i\}$ toward a distribution that satisfies the property constraint equation $$\sum_{i=1}^{N} \alpha_{ji} w_i = b_j.$$

The continuous factor $\phi$ takes a cubic polynomial in the property value b:

$$\phi(b) = A_1 b^3 + A_2 b^2 + A_3 b + A_4 \quad (10)$$

We determine the four constants $A_1$ through $A_4$ with the following constraints:

Conservation of total weight:

$$100 = \sum_{i=1}^{N} w_i \phi \quad (11a)$$

Averaged property constraint:

$$b_j = \sum_{i=1}^{N} \alpha_{ji} w_i \phi \quad (11b)$$

Smoothness at extreme values of the property j:

$$0 = \frac{\partial \phi}{\partial b} \text{ at } b = b_{min,j} \quad (11c)$$

$$0 = \frac{\partial \phi}{\partial b} \text{ at } b = b_{max,j} \quad (11d)$$

After we impose the constraints (11a-d) upon the factor $\phi$ defined in Equation 10, the factors and adjusted weights $\{w_i\}$ are computed as follows:

$$\phi = 1 + \gamma \Delta b_i \tag{12}$$

$$\gamma = \frac{b_j - \sum_{i=1}^{N} w_i * \alpha_{ji}}{\sum_{i=1}^{N} \alpha_{ji} w_i * \Delta b_i} \tag{13}$$

$$\Delta b_i = \left(\alpha_{ji}^3 - \frac{\sum_{i=1}^{N} \alpha_{ji}^3 w_i^*}{\sum_{i=1}^{N} w_i^*}\right) - \frac{3(b_{min,j} + b_{max,j})}{2}\left(\alpha_{ji}^2 - \frac{\sum_{i=1}^{N} \alpha_{ji}^2 w_i^*}{\sum_{i=1}^{N} w_i^*}\right) + \tag{14}$$

$$3(b_{min,j} + b_{max,j})\left(\alpha_{ji} - \frac{\sum_{i=1}^{N} \alpha_{ji} w_i^*}{\sum_{i=1}^{N} w_i^*}\right)$$

$$w_i = w_i * (1 + \gamma \Delta b_i) \text{ for } i = 1, \ldots, N \tag{15}$$

We avoid the occurrence of $\phi<0$ by restricting the property target range ($b_{min,j}$, $b_{max,j}$). If the actual target $b_j$ is outside this range, we approach this target in multiple steps.

In the case of multiple average property targets, we may calculate separate weight factors $\phi_j$ for each target property j. However, we have achieved much greater effectiveness by using a single factor that includes the dependence of all averaged property targets. The factor adds all cubic polynomials together in Equation 10, with three additional parameters for each target. Constraints in Equation 11 are also used for each property. Final factors and weight adjustments are similar in form to Equations 12-15.

Distributed Property Targets

In general, a distributed property target occurs when the property to be matched varies with some independent variable. The distribution of weight distilled with boiling point temperature, i.e. the distillation curve, is the most frequently encountered distributed target. In the successive substitution method, we design a factor $\phi$ that effectively "redistills" the reference weight distribution $\{w_i^*\}$ during each iteration of the reconciliation algorithm we describe below.

Figure 2:
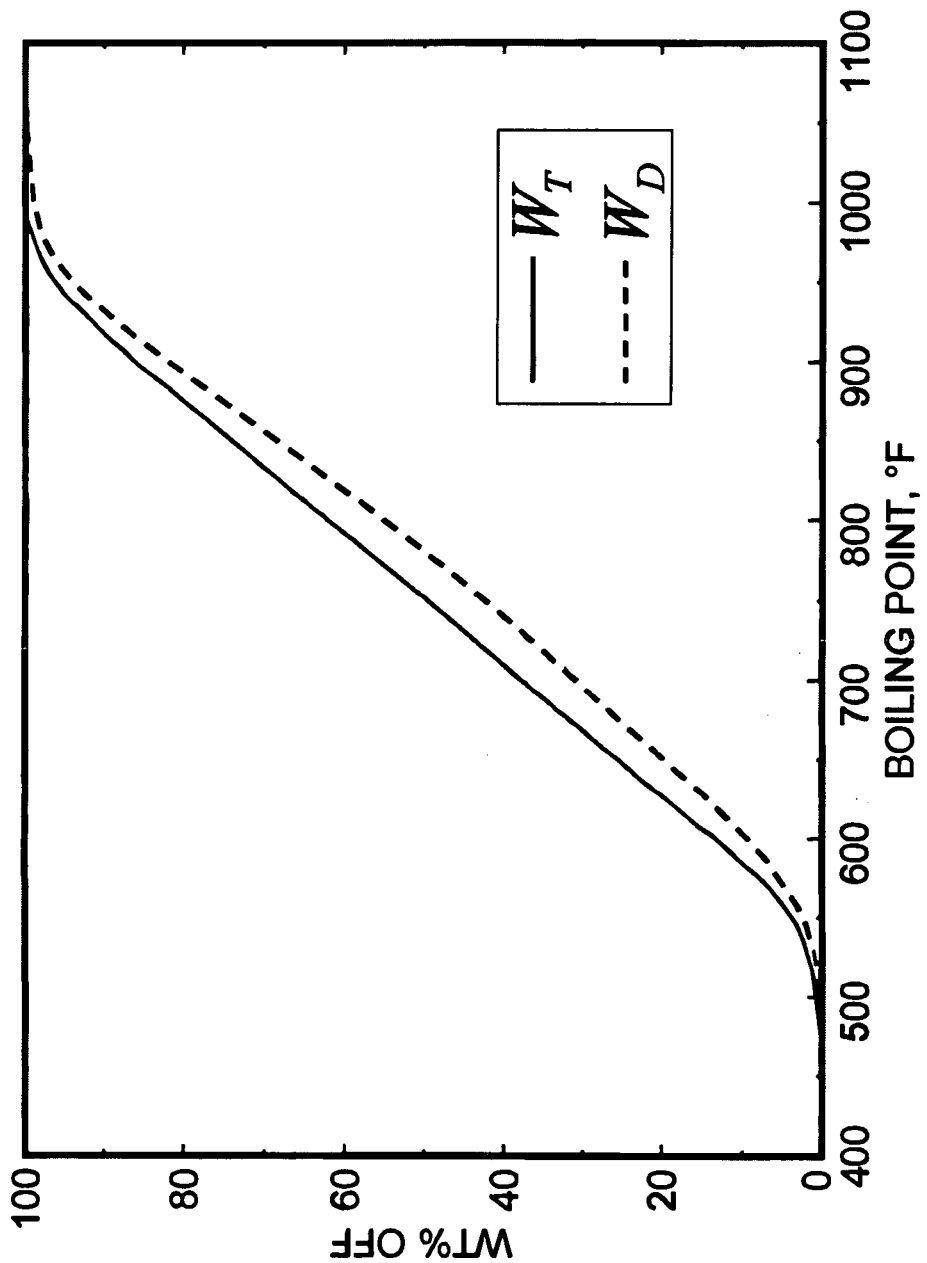
FIG. 2 shows example target ($W_T$) and reference ($W_D$) boiling point distributions.
Figure 3:
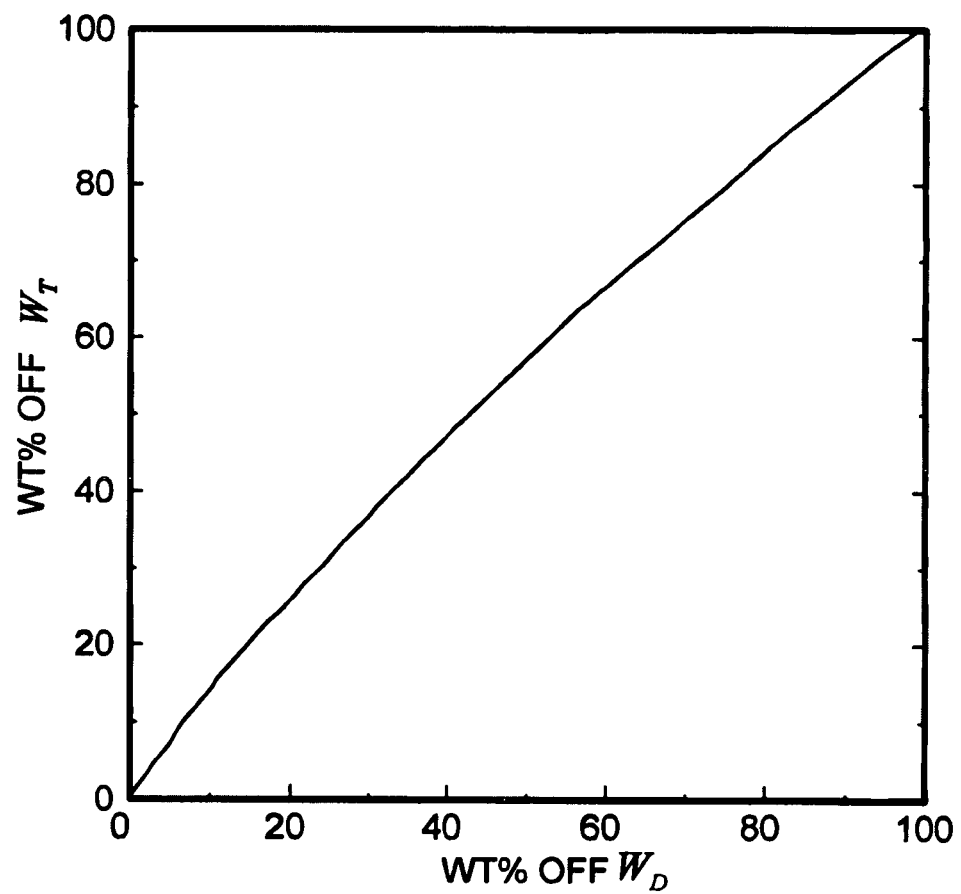
FIG. 3 shows a plot comparing the target ($W_T$) and reference ($W_D$) cumulative distributions.
Figure 4:
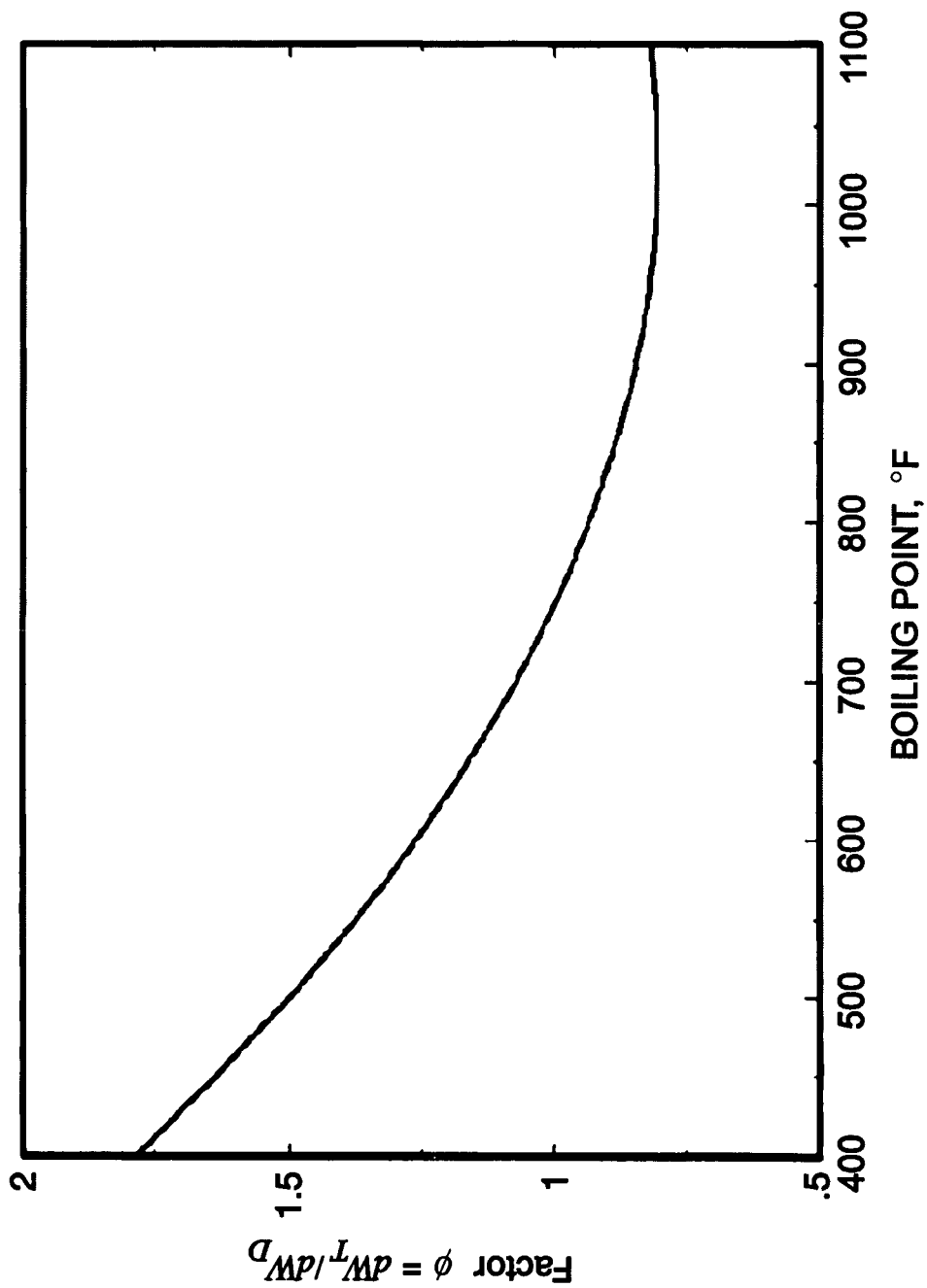
FIG. 4 shows a how the factor, $\phi$, used to adjust the reference weights varies with boiling point.

Let W(BP) represent the cumulative weight percent distilled off at boiling point BP. The measured target distribution is $W_T$, and $W_D$ is calculated from the reference weight distribution $\{w_i^*\}$ of the molecular lumps. Both of these cumulative weight distributions are monotonically increasing functions of the boiling point BP (see FIG. 2). In practice, the cumulative weight distribution $W_T$ is measured at discrete boiling points. Also, we calculate the distribution $W_D$ at the boiling points of each molecular lump. However, we may interpolate between these discrete boiling points using smooth functions that preserve the monotonically increasing nature of a cumulative weight distribution. After this interpolation, we determine the target distribution $W_T$ as a function of the calculated distribution $W_D$ at the same distillation boiling points (see FIG. 3). Finally, we calculate the factor $\phi=dW_T/dW_D$ as a function of boiling point (see FIG. 4). We use the factor $\phi$ to adjust the reference weights as follows:

$$w_i = \frac{100 w_i * \phi(BP_i)}{\sum_{j=1}^{N} w_j * \phi(BP_j)} \text{ for } i = 1, \ldots, N \tag{13}$$

where $BP_i$ is the boiling point of molecular lump i.

c) The Successive Substitution Reconciliation Algorithm

Figure 5:
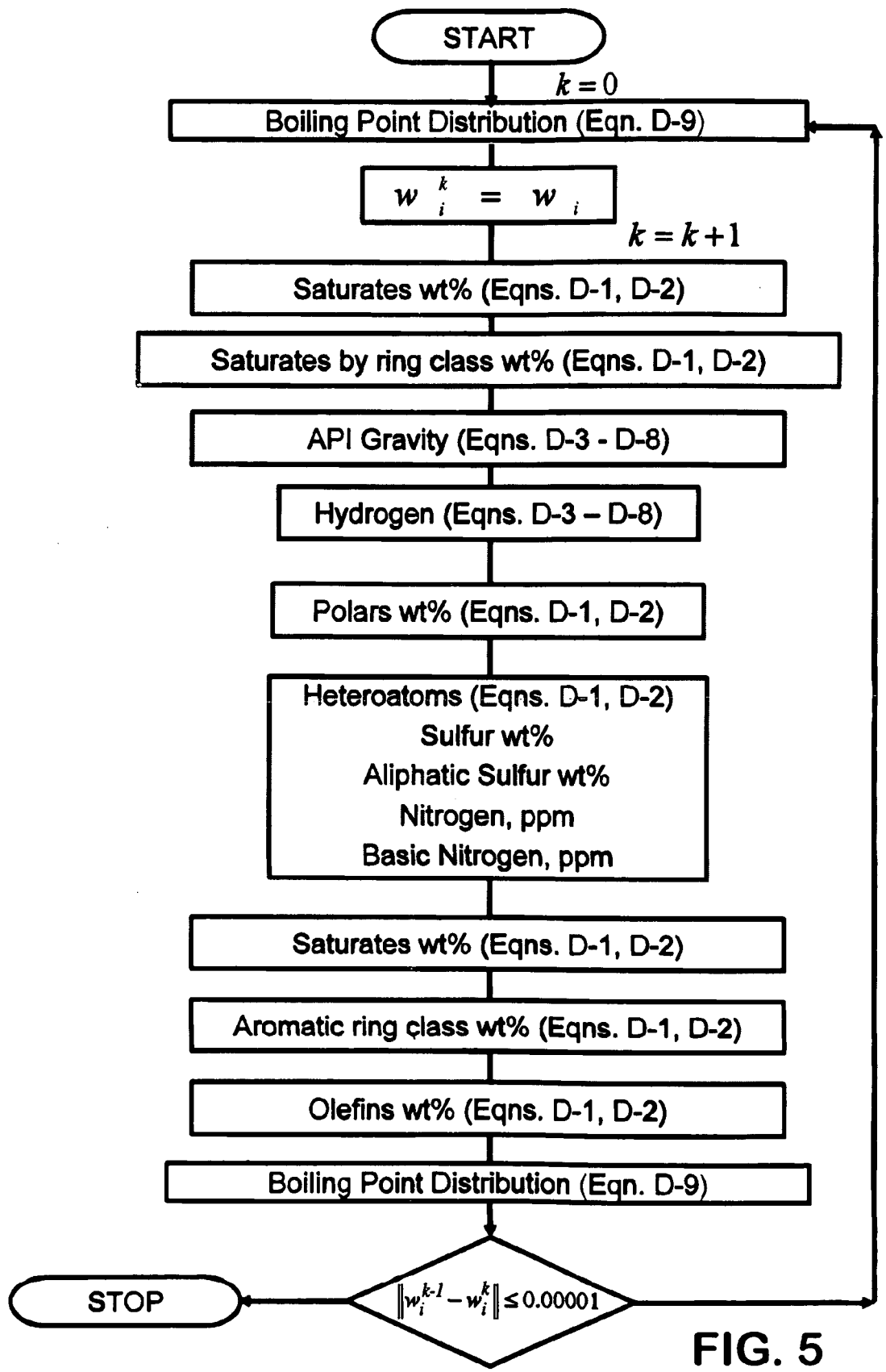
FIG. 5 shows a flowchart for the iterative model-of-composition synthesis algorithm.

In FIG. 5, we show the typical embodiment of the successive substitution reconciliation where a reference model-of-composition is adjusted to match one distributed target (boiling point), and more than one scalar property targets. In general, adjusting weight percents to match each target in sequence disrupts the previous match so that the weight percent adjustments are relaxed, or dampened, to ensure convergence of the successive substitution algorithm.

d) Targets Based on Multivariate Analytical Measurement

The targets used in reconciliation may include ones estimated based on the multivariate analytical data used Step 1 of the invention. These targets may be calculated based on the reference composition determined from Step 1. Alternatively, these targets may be estimated via regression models developed for this purpose. Such regression models can be developed using standard chemometric techniques such as Multi-linear Regression (MLR), Principal Components Regression (PCR), or Partial Least Squares (PLS) or via the method of Brown (U.S. Pat. No. 5,121,337, Jun. 9, 1992). The multivariate analytical data for the references in the library database for Step 1 are regressed against measured target data to form a predictive model. This model may then be applied to the multivariate data for the unknown being analyzed to estimate a target to use in Step 2. For example, a regression model can be built to relate FT-IR spectra of the references to aromatic carbon content measured by NMR. Said model is used to estimate an aromatic carbon content target for the sample being analyzed.

EXAMPLES 1 & 2

The current invention can be used to estimate a composition for a crude oil, or distillation cuts thereof. In Step 1, the methodology of U.S. Pat. No. 6,662,116 and US 2006/0047444 A1 is used to estimate a blend of reference crudes for which models of composition have been measured. The blend of these models of composition serves as a reference for subsequent synthesis in Step 2. If the crude oil being analyzed is one for which crude assay data was either measured, or estimated using the methods of U.S. Pat. No. 6,662,116 or US 2006/0047444 A1, then properties estimated from the model of composition match those of the assay. In this case, the targets used in the Step 2 synthesis will typically be distributed targets (property values as a function of boiling point) rather than bulk targets (properties of the whole sample). Examples 1 and 2 compare models of composition built using bulk and distributed targets.

The validity of the technique was demonstrated as follows. A library of 73 crudes was collected, every member of which had, (i) a measured HDHA composition, (ii) a measured assay, (iii) a FTIR spectrum and (iv) other bulk properties (including API gravity and viscosity). A series of test runs (known as cross-validation runs) were conducted by selectively removing one crude at a time from the library and treating it as a sample of unknown composition, in order to estimate its composition from the remaining 72 crudes using the procedure outlined above. Each test run consisted of three steps. First, a blend of the 72 crudes was constructed that best matched the FTIR spectrum, API and viscosity of the sample removed using the methodology of U.S. Pat. No. 6,662,116 and US 2006/0047444 A1. Next, the HDHA based compositions of the 72 crudes were blended in proportion of the blend suggested in the previous step to obtain the "reference" composition. Finally, the synthesis algorithm was applied on the reference composition to match additional measured either bulk or distributed targets of the removed sample, such as gravity (API or specific), the boiling curve, nitrogen, basic nitrogen, sulfur and aliphatic sulfur. The estimated composition was then compared to the actual measured composition available from the removed sample's HDHA.

EXAMPLE 1

An MSO Edmonton crude oil was analyzed using the method of this invention relative to the remaining 72 crudes in the library. In the first step, the spectrum, API gravity and viscosity of the crude oil are used as inputs, and the method of U.S. Pat. No. 6,662,116 is used to calculate a blended reference. The blend recipe is shown in Table 1.

TABLE 1

| Component | % |
|---|---|
| WEST TEXAS INTERMEDIATE | 17.89 |
| MESA 30 | 13.59 |
| ELK BASIN HEAVY | 12.71 |
| MARGHAM CONDENSATE | 10.36 |
| QATAR MARINE | 8.05 |
| SMILEY COLEVILLE | 7.36 |
| OSEBERG BLEND | 6.39 |
| MIDALE | 6.2 |
| WEST TEXAS SOUR | 4.63 |
| ZAFIRO | 2.4 |
| URALS | 2.21 |
| OSO CONDENSATE | 2.19 |
| HAWKINS MIX | 1.88 |
| SYNCRUDE | 1.86 |
| FORCADOS | 1.55 |
| VASCONIA BLEND | 0.74 |

Figure 6:
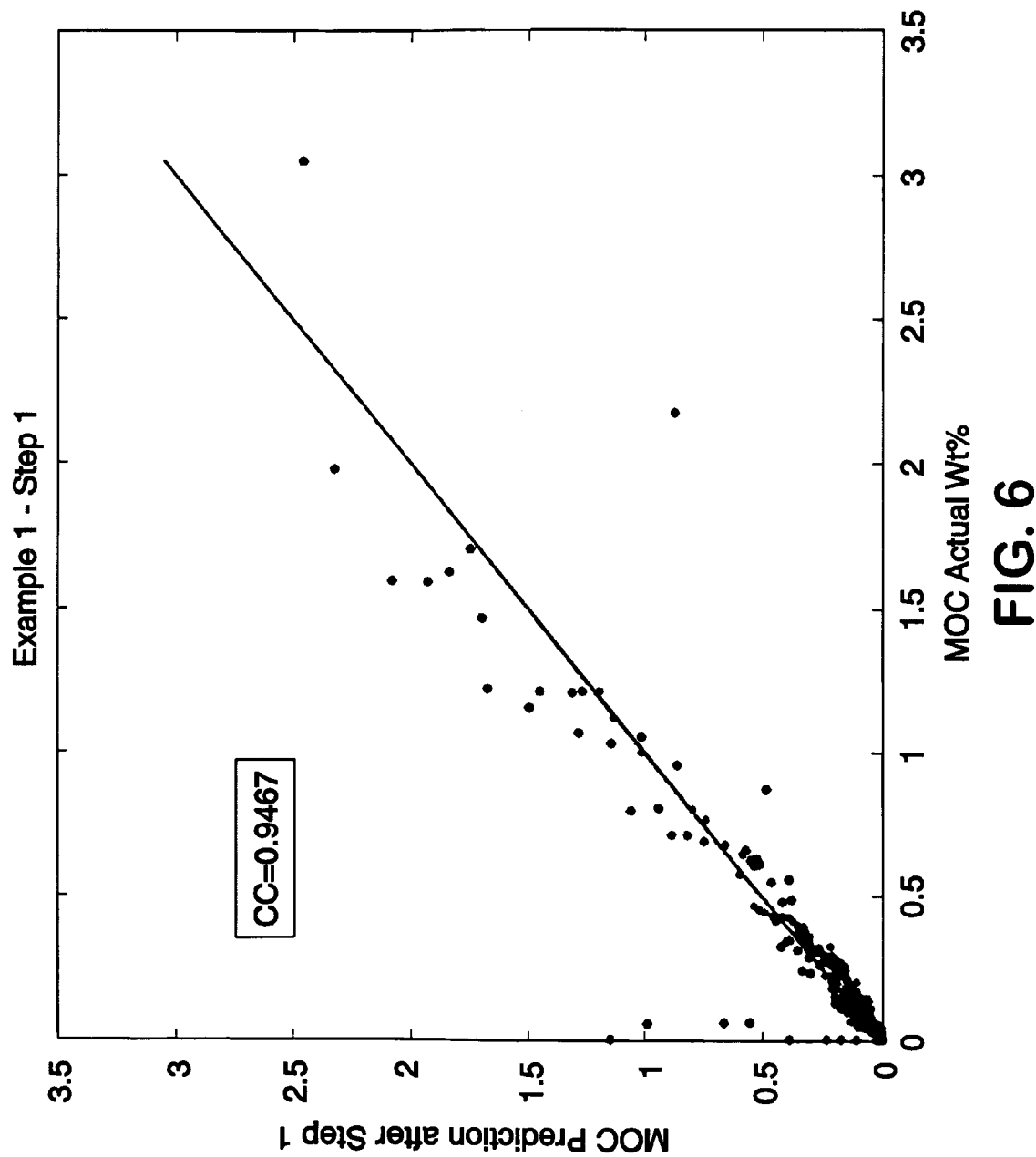
FIG. 6 shows a parity plot comparing the MOC for Example 1, Step 1 to the measured MOC.
Figure 7:
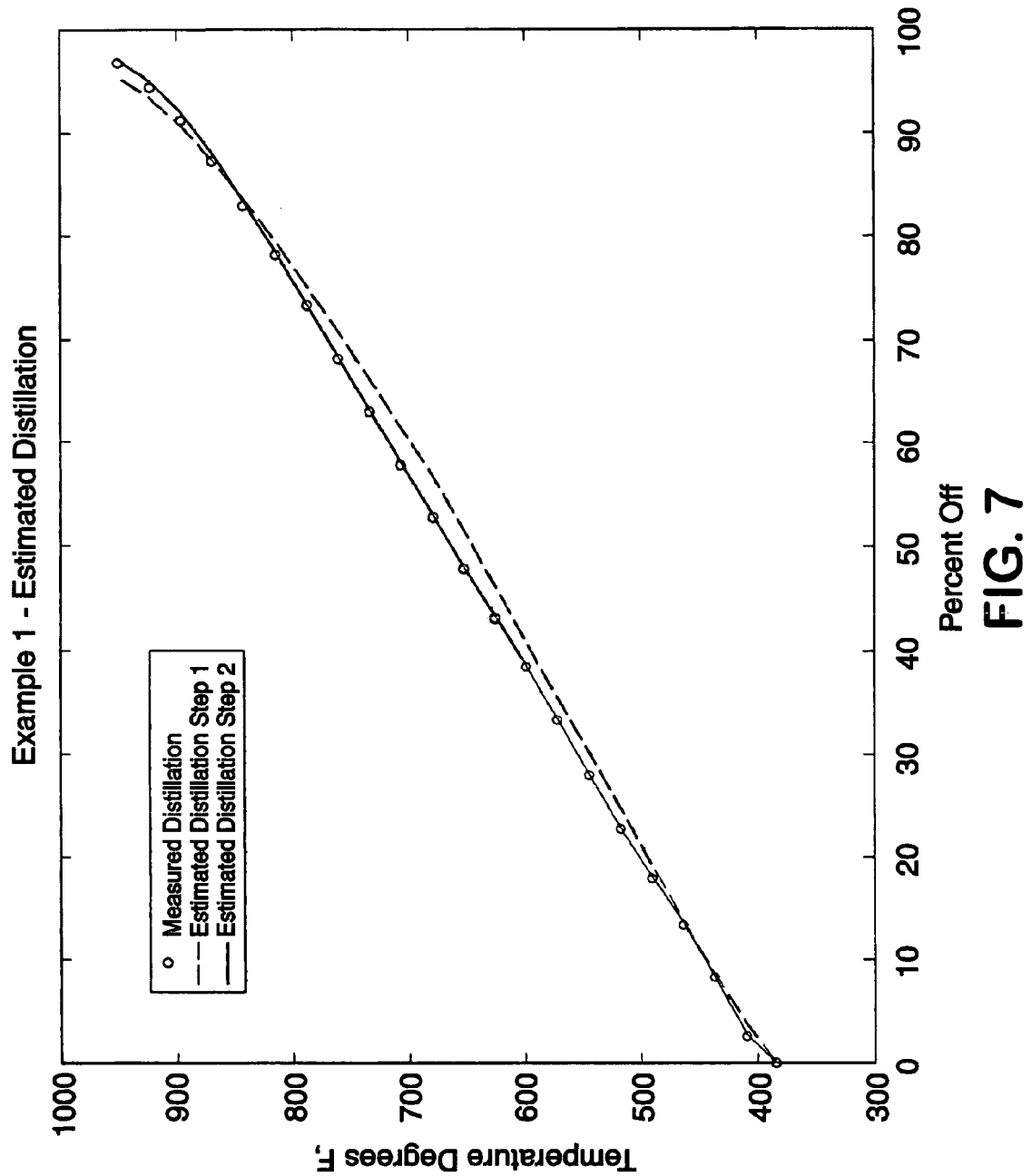
FIG. 7 compares the distillation calculated from the MOC of Example 1, Step 1 to the measured distillation.

FIG. 6 compares the weights for the model of composition calculated from this blended reference (y-axis, MOC predicted after step 1) to those measured for the MSO Edmonton crude α-axis, MOC actual wt %). Brown (US2006/0047444 A1) defined a Fit Quality Ratio (FQR) as a measure of how well the spectrum and inspections of the unknown (MSO Edmonton) are matched by the calculated blend, a value of less than 1 being very good fits, between 1 and 1.5 acceptable and larger values indicative of poorer fits. An FQR of 1.02 was obtained in this example indicating the blend is a reasonably good match to the sample being analyzed. In FIG. 6, the diagonal parity line represents complete agreement between the MOC estimated by step 1 of the current invention and the measured MOC. The fact that most MOC components fall close to the parity line demonstrates the ability of the FTIR based blending algorithm to capture the significant molecular trends of the actual composition in the reference. The correlation coefficient between the estimated and measured MOCs is 0.9467. Despite this good agreement, properties calculated from the blended reference MOS are not in complete agreement with those measured. For example, the 30.45 API gravity calculated from the blended reference MOC is higher than the 28.98 measured value (Table 2). Similarly, the estimated distillation curve (FIG. 7 dashed line) does not exactly match the measured distillation (FIG. 7 open circles).

Figure 8:
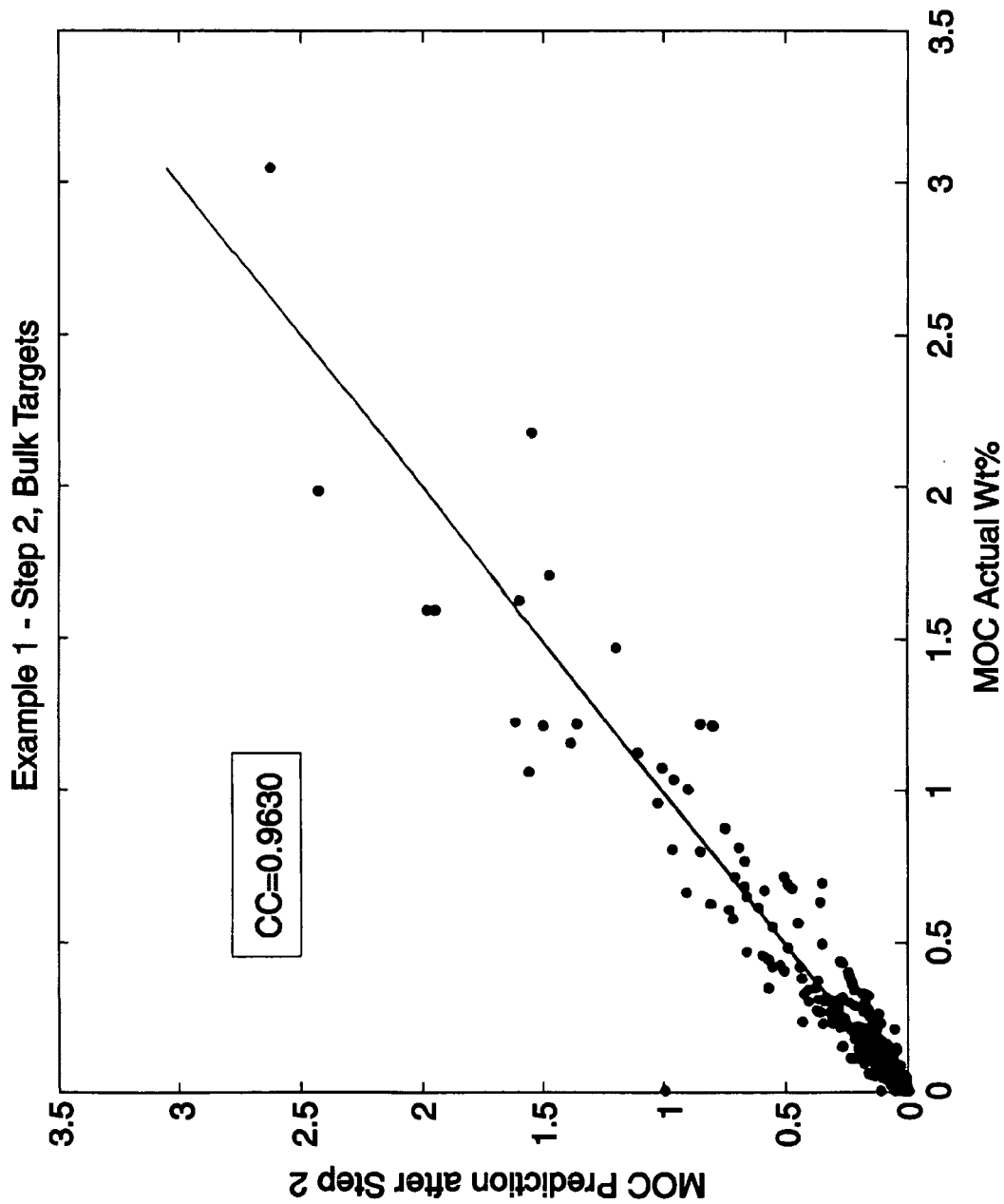
FIG. 8 shows a parity plot comparing the MOC for Example 1, Step 2 using bulk targets to the measured MOC.
Figure 9:
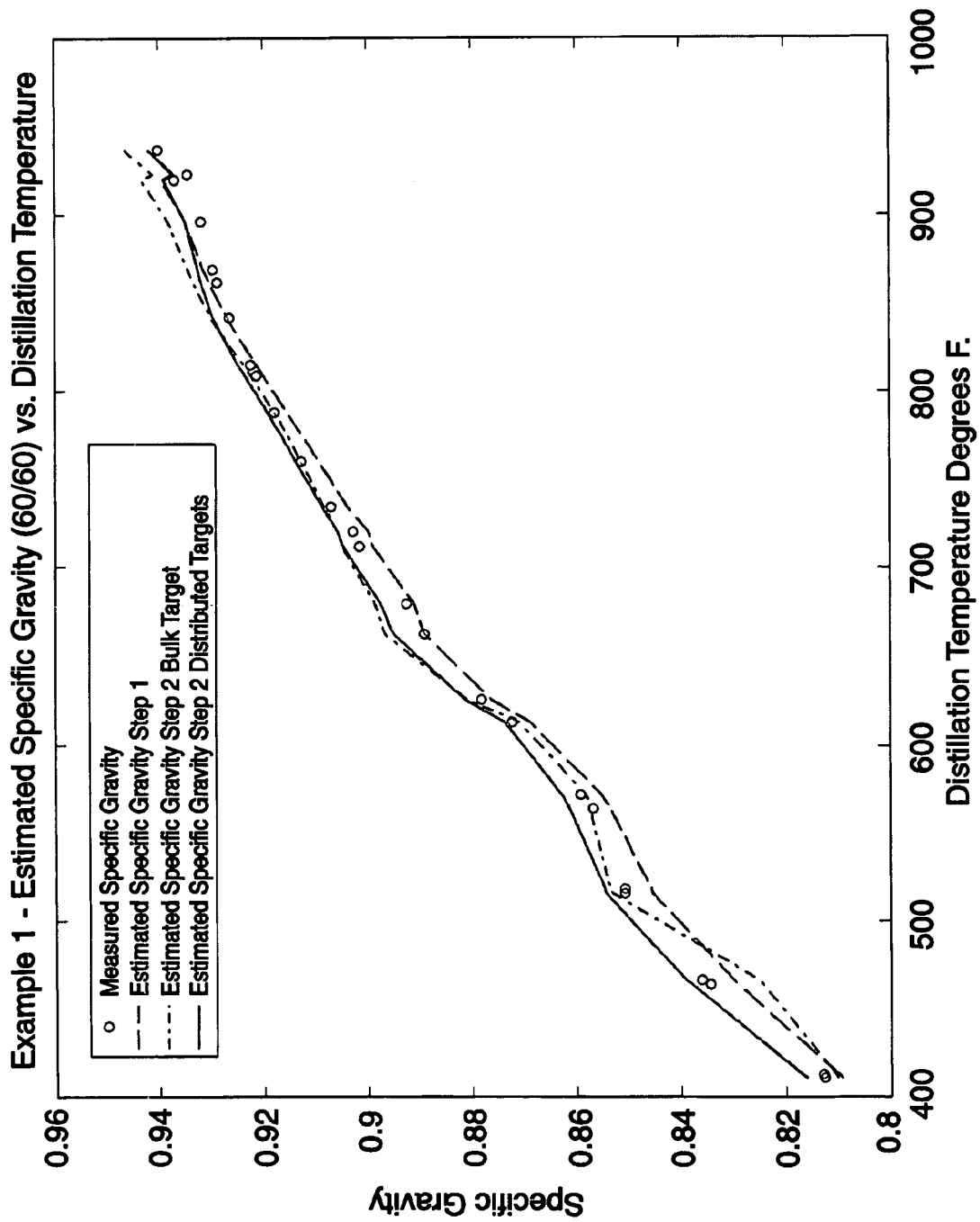
FIG. 9 compares specific gravity calculated from the MOCs for Example 1 after Step 1, Step 2 using bulk targets, and Step 2 using distributed targets to the measured specific gravity.
Figure 10:
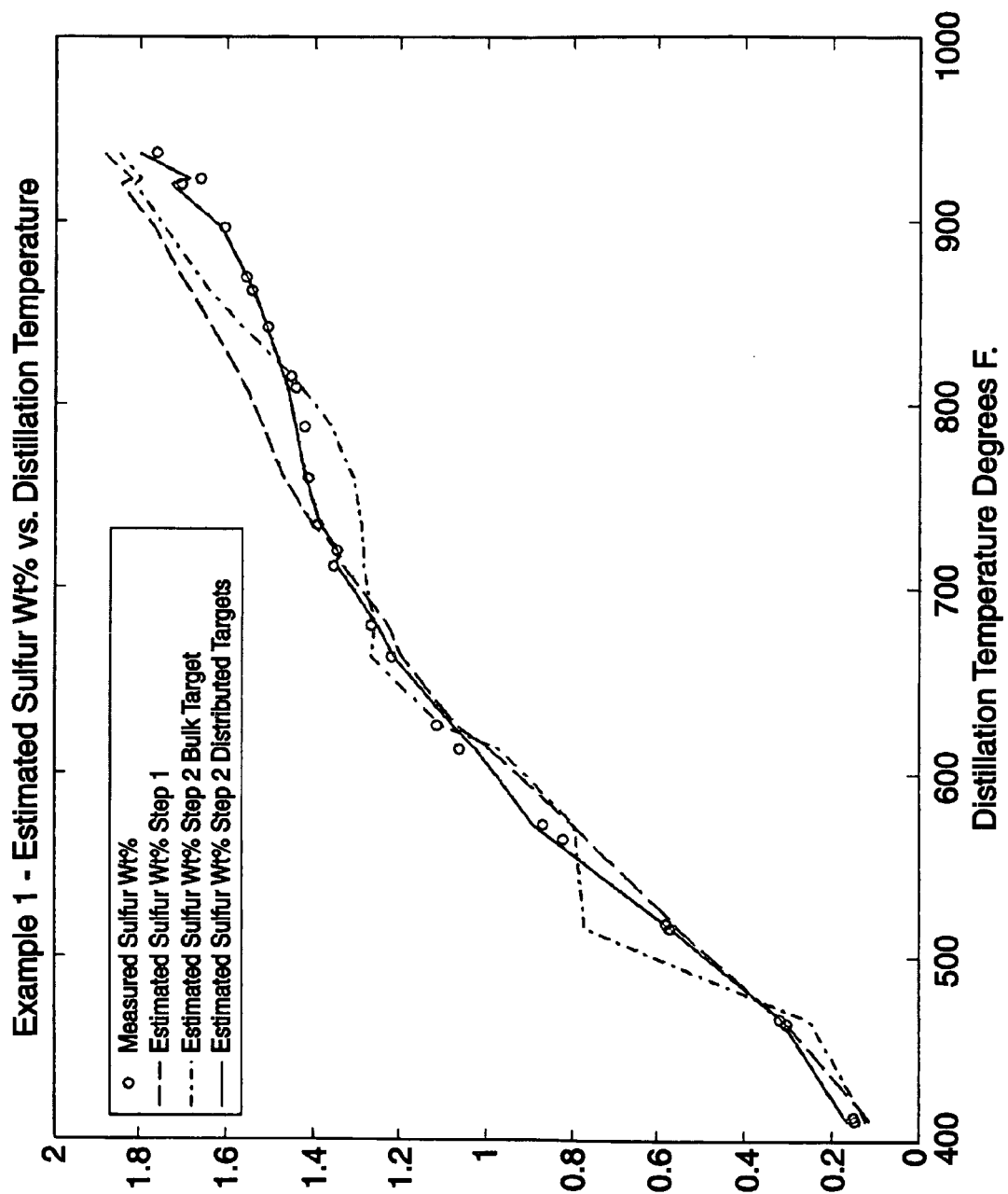
FIG. 10 compares sulfur calculated from the MOCs for Example 1 after Step 1, Step 2 using bulk targets, and Step 2 using distributed targets to the measured sulfur.
Figure 11:
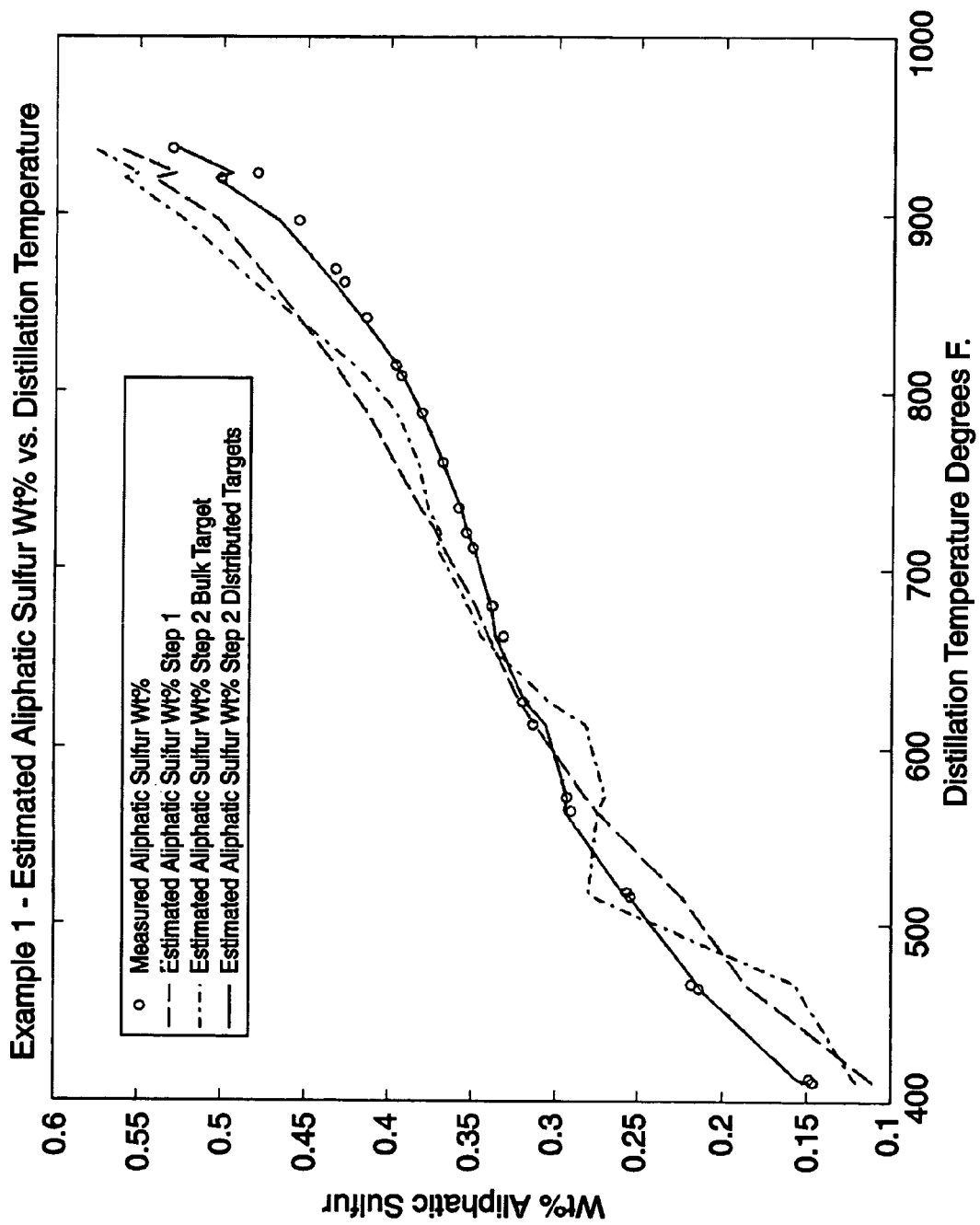
FIG. 11 compares aliphatic sulfur calculated from the MOCs for Example 1 after Step 1, Step 2 using bulk targets, and Step 2 using distributed targets to the measured aliphatic sulfur.
Figure 12:
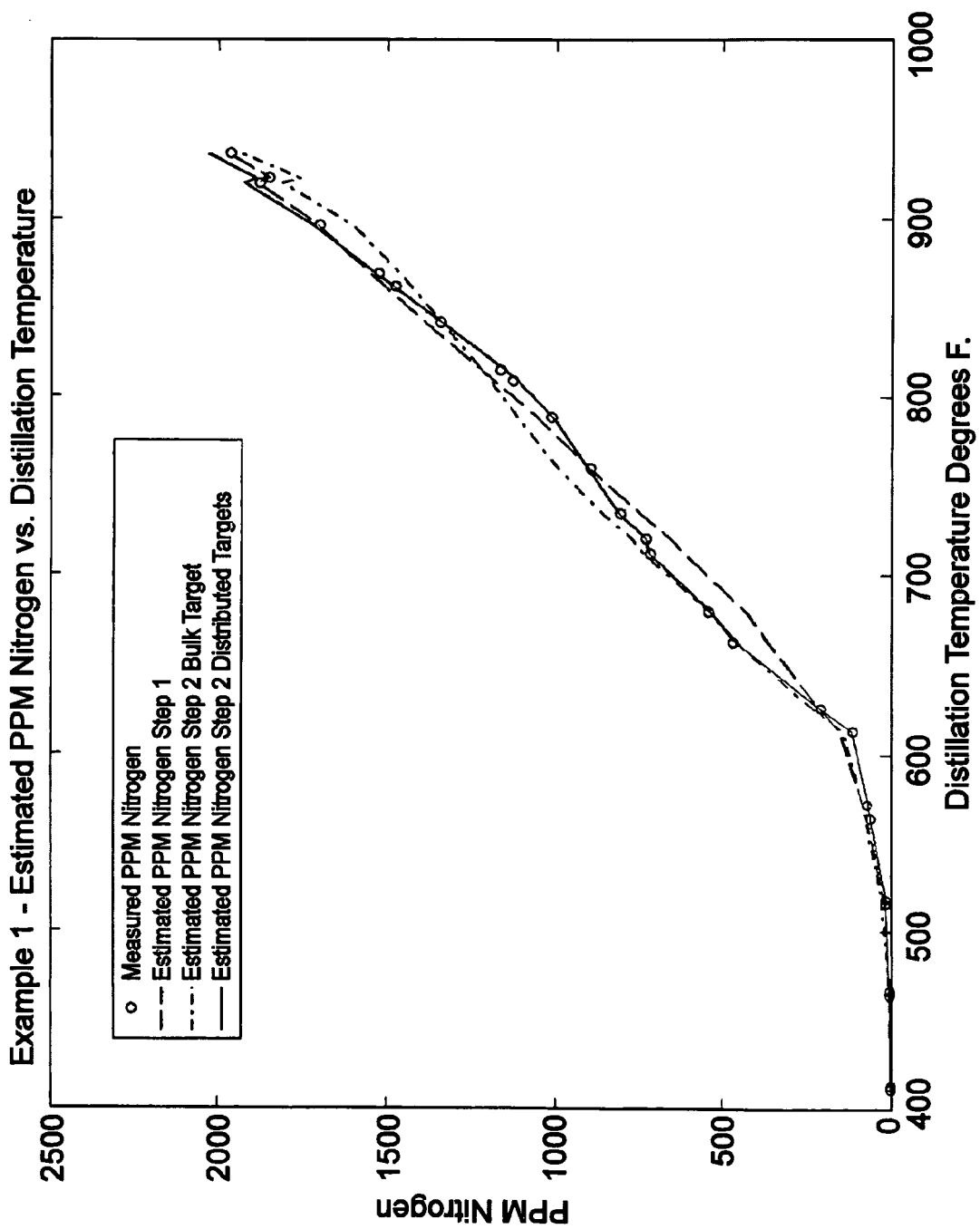
FIG. 12 compares nitrogen calculated from the MOCs for Example 1 after Step 1, Step 2 using bulk targets, and Step 2 using distributed targets to the measured nitrogen.

FIG. 8 compares the weights for the model of composition after step 2 synthesis to bulk properties (y-axis) to those measured for the MSO Edmonton crude α-axis). The step 2 synthesis provides only marginal improvement in the correlation coefficient (0.9630 after synthesis), but the MOC now more closely matches the measured property targets. From Table 2, the API and Sulfur agree exactly with the measured targets. From FIG. 7, the estimated distillation (solid curve) now agrees more closely with the measured data (open circles). FIGS. 9-12 compare the property values for the model of composition after step 1 (dashed lines), step 2 synthesis to bulk properties (dash-dot lines), step 2 synthesis to distributed properties (solid lines) to the measured property data (open circles. Since the blended reference is a very good approximation of the composition, the distributed properties only move slightly during synthesis as shown in FIGS. 9-12. For synthesis to bulk properties, there are minor differences between the estimate property distributions generated using this invention (dash-dot lines) and those measured (open circles), even for those properties that are used as targets. However, for synthesis to distributed targets (solid lines), the estimated property distribution for the target properties agree with those the measured data. The result demonstrates how the synthesis allows for a match to all these targets while retaining the correct structure of the compositional patterns.

TABLE 2

| | Actual | Blended Reference | Tuned to Bulk Targets | Tuned to Dist Targets |
|---|---|---|---|---|
| API | 28.98 | 30.45 | 28.98 | 28.54 |
| SAT wt % | 64.4 | 65.2 | 62.6 | 61.5 |
| n-PAR wt % | 12.05 | 11.23 | 10.8 | 10.16 |
| i-PAR wt % | 12.37 | 15.93 | 14.3 | 13.6 |
| 1-ring | 19.04 | 20.2 | 18.75 | 18.61 |
| 2-ring | 12.55 | 12.25 | 12.32 | 12.66 |
| 3-ring | 5.74 | 4.41 | 4.89 | 5 |
| 4-ring | 2.11 | 1.07 | 1.33 | 1.32 |
| 5-ring | 0.5 | 0.12 | 0.16 | 0.16 |
| 6-ring | 0.03 | 0.03 | 0.03 | 0.03 |
| S wt % | 1.05 | 1.01 | 1.05 | 1.05 |
| aliph S wt % | 0.33 | 0.32 | 0.33 | 0.33 |
| tot N ppm | 615.32 | 536.36 | 615.62 | 607.7 |
| basic N ppm | 187.14 | 187.35 | 187.94 | 185.43 |
| H2 wt % | 12.81 | 12.9 | 12.75 | 12.69 |
| POLAR wt % | 0.53 | 0.53 | 0.56 | 0.53 |
| ARO + SUL wt % | 35.07 | 34.23 | 36.88 | 37.93 |
| ARC1 | 13.47 | 13.44 | 14.02 | 14.51 |
| ARC2 | 10.17 | 10.07 | 10.78 | 11.44 |
| ARC3 | 5.76 | 5.37 | 6.04 | 6.1 |
| ARC4 | 2.96 | 2.52 | 3.03 | 2.91 |
| RI@70 | 1.4703 | 1.4668 | 1.4716 | 1.473 |
| % CA | 16.11 | 15.79 | 16.94 | 17.56 |
| pour pt C. | 24.1 | 20.5 | 21.7 | 20.7 |
| cloud pt C. | 31.8 | 30.8 | 30.4 | 29.7 |
| freeze pt C. | 31.8 | 30.8 | 30.4 | 29.7 |
| TAN mg/g | 0.2 | 0.2 | 0.2 | 0.2 |

EXAMPLE 2

Figure 13:
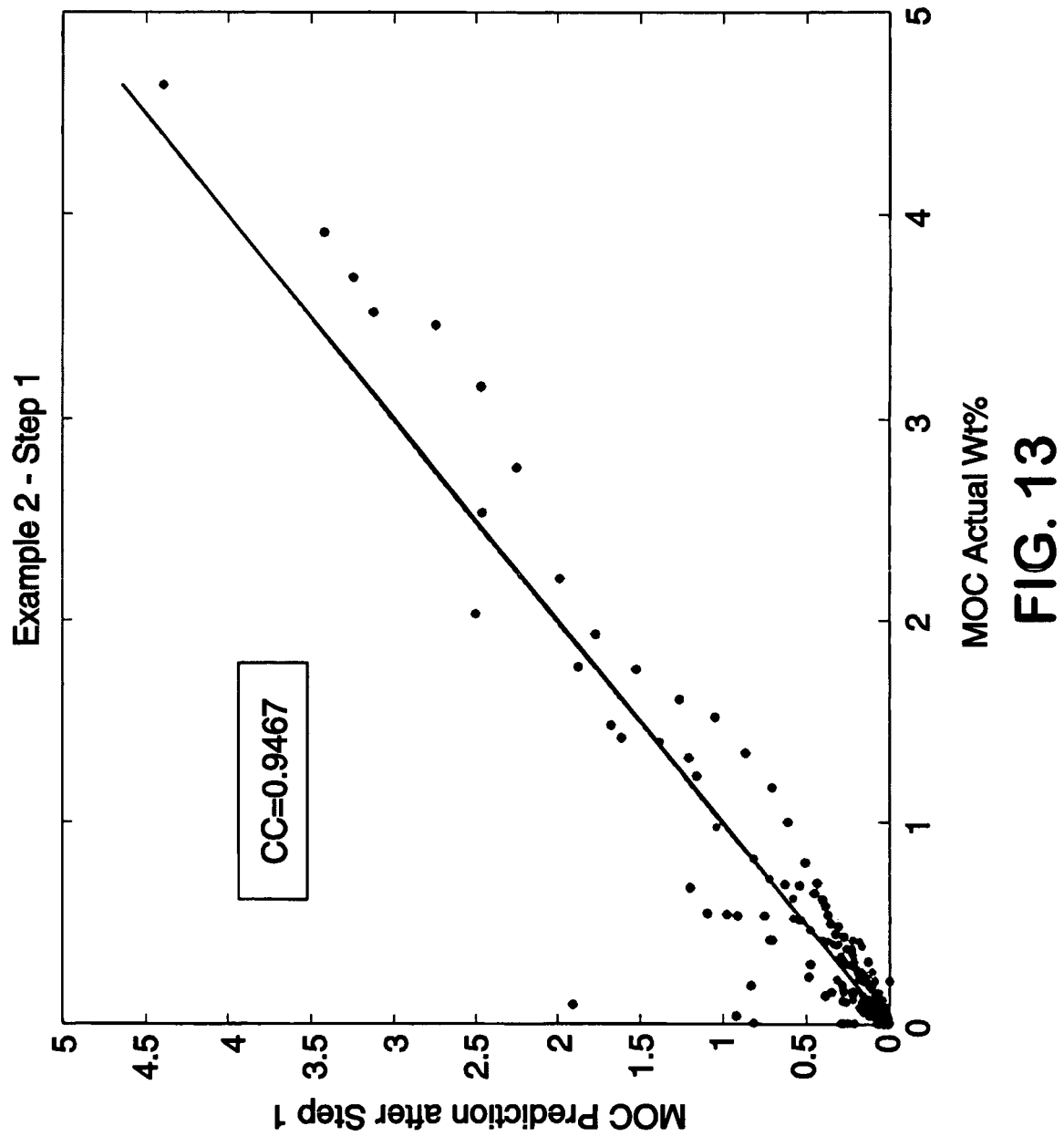
FIG. 13 shows a parity plot comparing the MOC for Example 2, Step 1 to the measured MOC.
Figure 14:
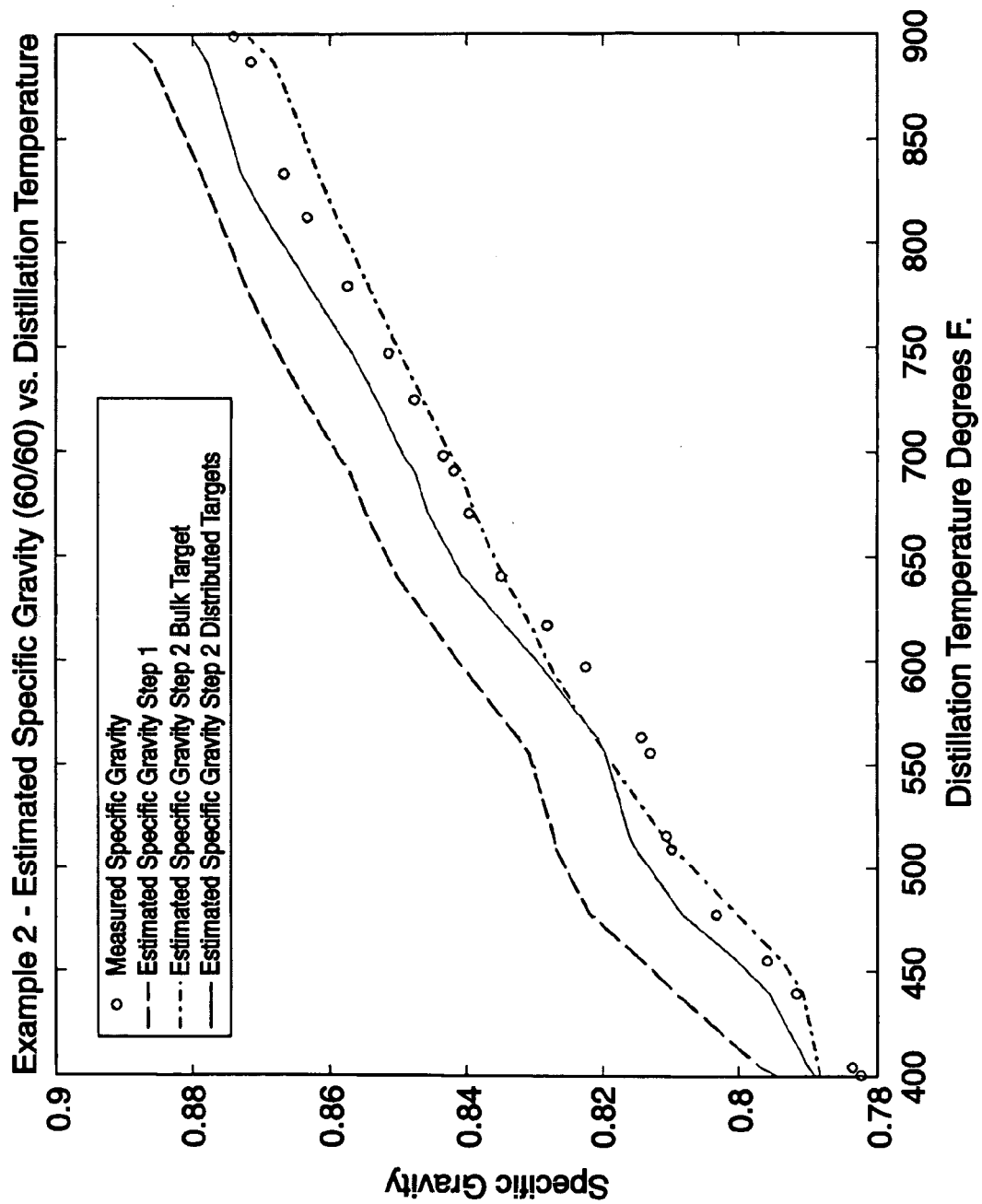
FIG. 14 compares the distillation calculated from the MOC of Example 2, Step 1, Step 2 using bulk properties and Step 2 using distributed properties to the measured distillation.
Figure 15:
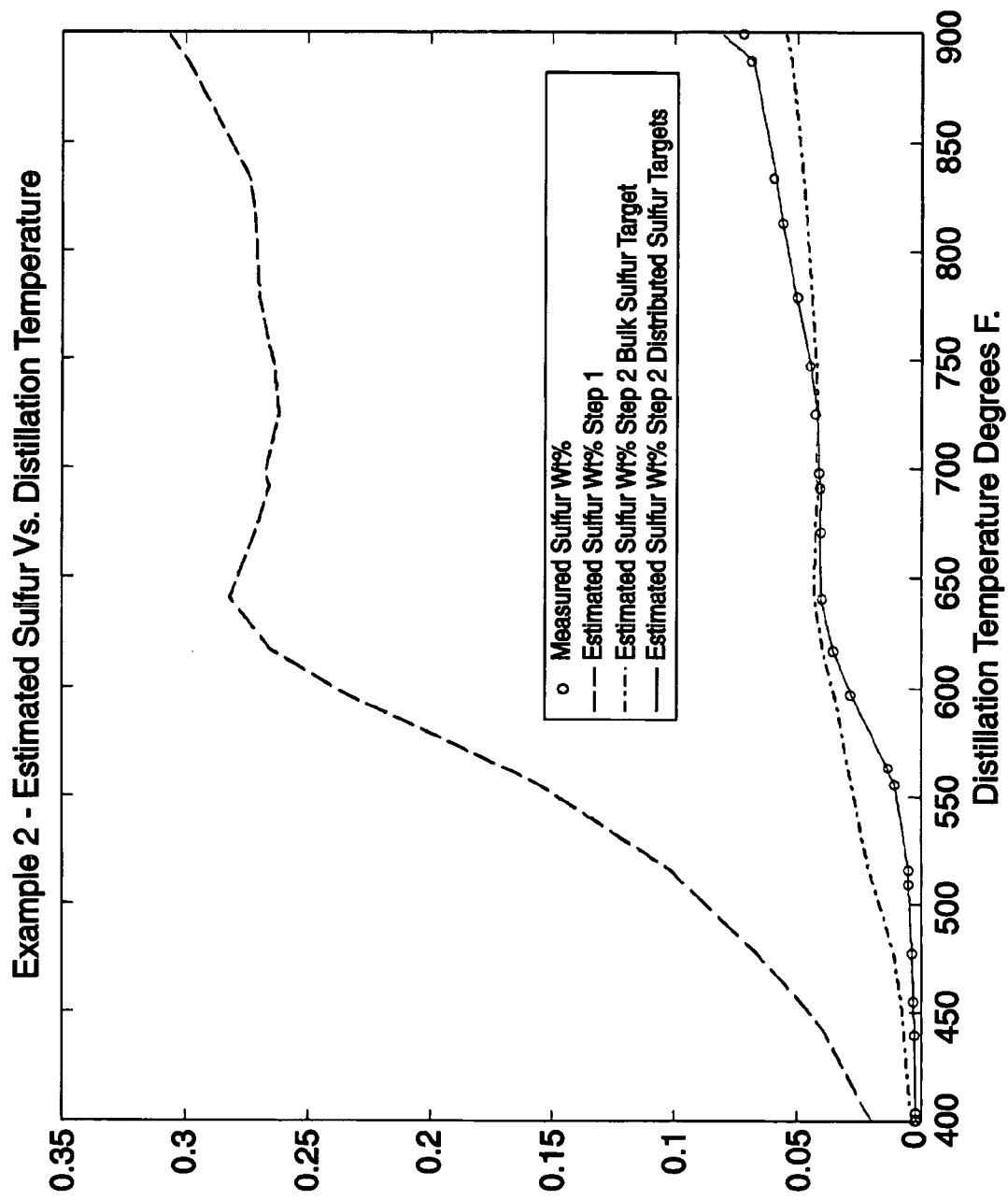
FIG. 15 compares the sulfur calculated from the MOC of Example 2, Step 1, Step 2 using bulk properties and Step 2 using distributed properties to the measured sulfur.
Figure 16:
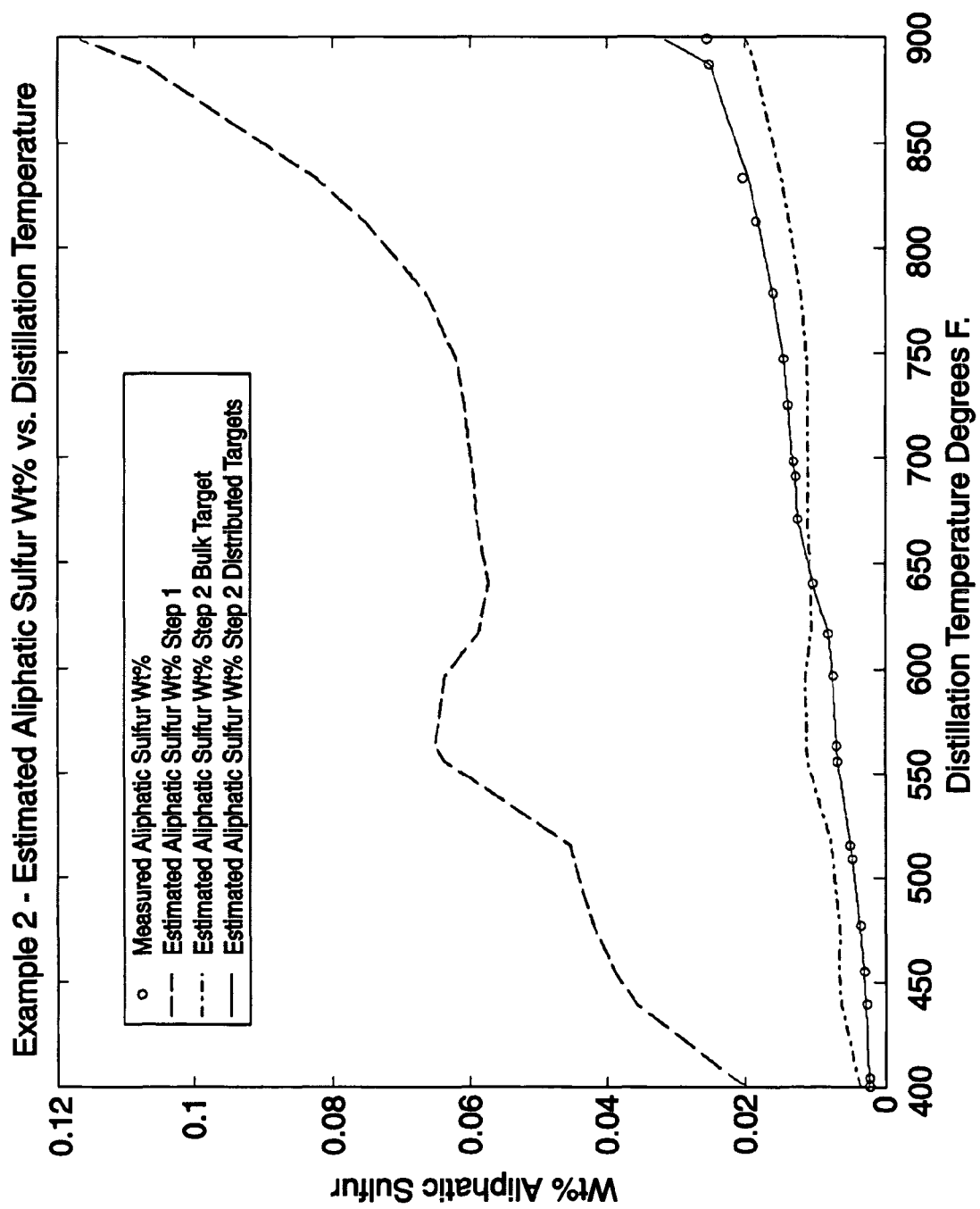
FIG. 16 compares the aliphatic sulfur calculated from the MOC of Example 2, Step 1, Step 2 using bulk properties and Step 2 using distributed properties to the measured aliphatic sulfur.
Figure 17:
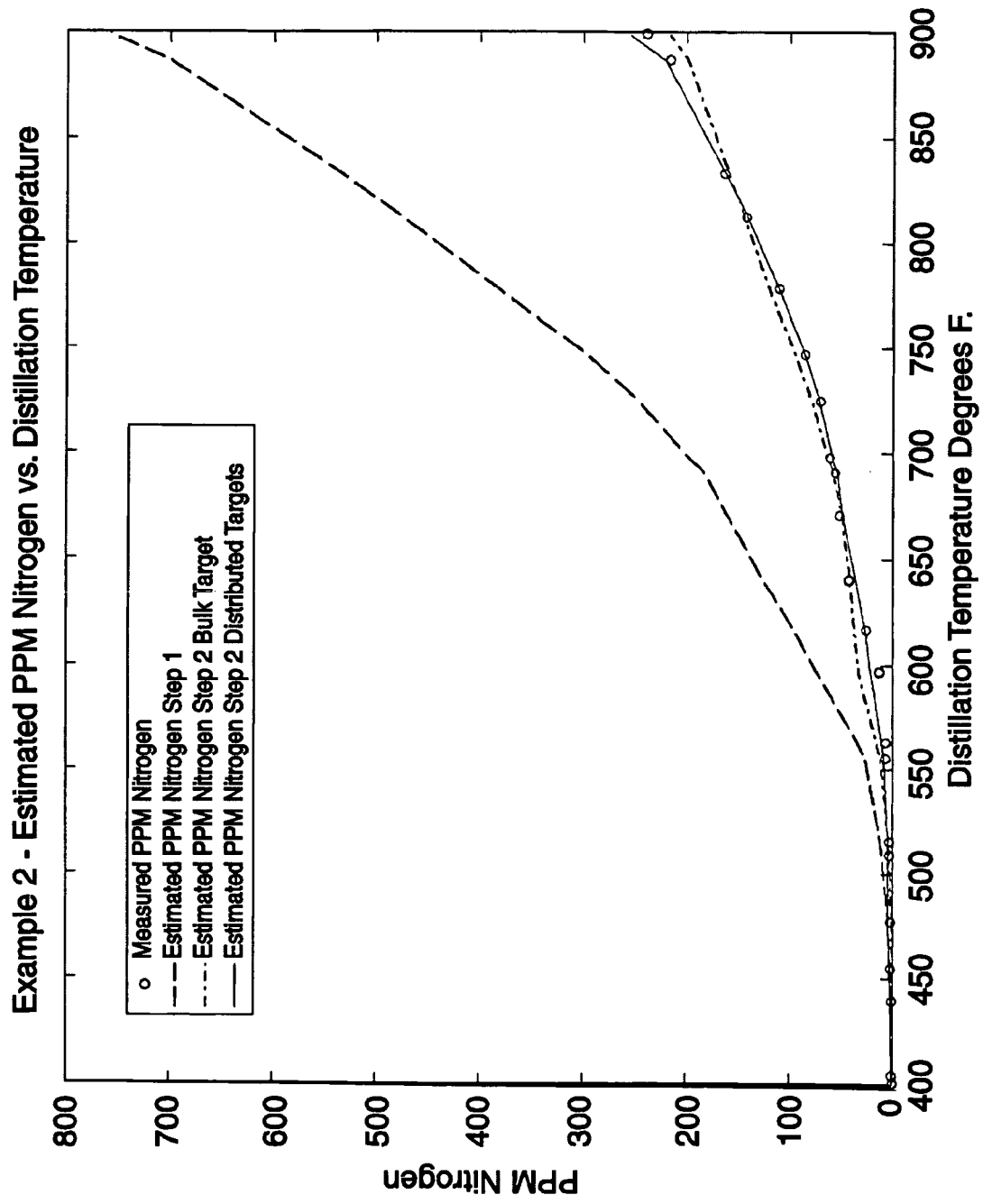
FIG. 17 compares the nitrogen calculated from the MOC of Example 2, Step 1, Step 2 using bulk properties and Step 2 using distributed properties to the measured nitrogen.

A Brookland crude was analyzed relative to the 72 other reference crudes in the library. The blend calculated from Step 1 is shown in Table 3. Note in this case, the FQR statistic is 2.43 indicating that, because of the small library size, the blend is not a good match to the crude being analyzed. As seen in FIG. 13, there is poorer agreement between the MOC weights predicted from the blended reference (y-axis) and those measured for the Brookland crude (x-axis). The correlation coefficient is 0.9467. From Table 4, and FIGS. 14-17 compare the properties calculated from the blended reference MOC (Table 4, column 3 and FIGS. 14-17 dashed lines) to those measured for Brookland crudes (column 2 and open circles). The model of composition for the blended reference (curves) differs significantly from the actual measured crude MOC, particularly in terms of the aromatic and sulfide components.

TABLE 3

| Component | % |
|---|---|
| N"KOSSA | 40.99 |
| MARGHAM CONDENSATE | 34.22 |
| TENGIZ | 14.82 |
| TAPIS | 8.96 |
| COOPER BASIN | 1.01 |

Figure 18:
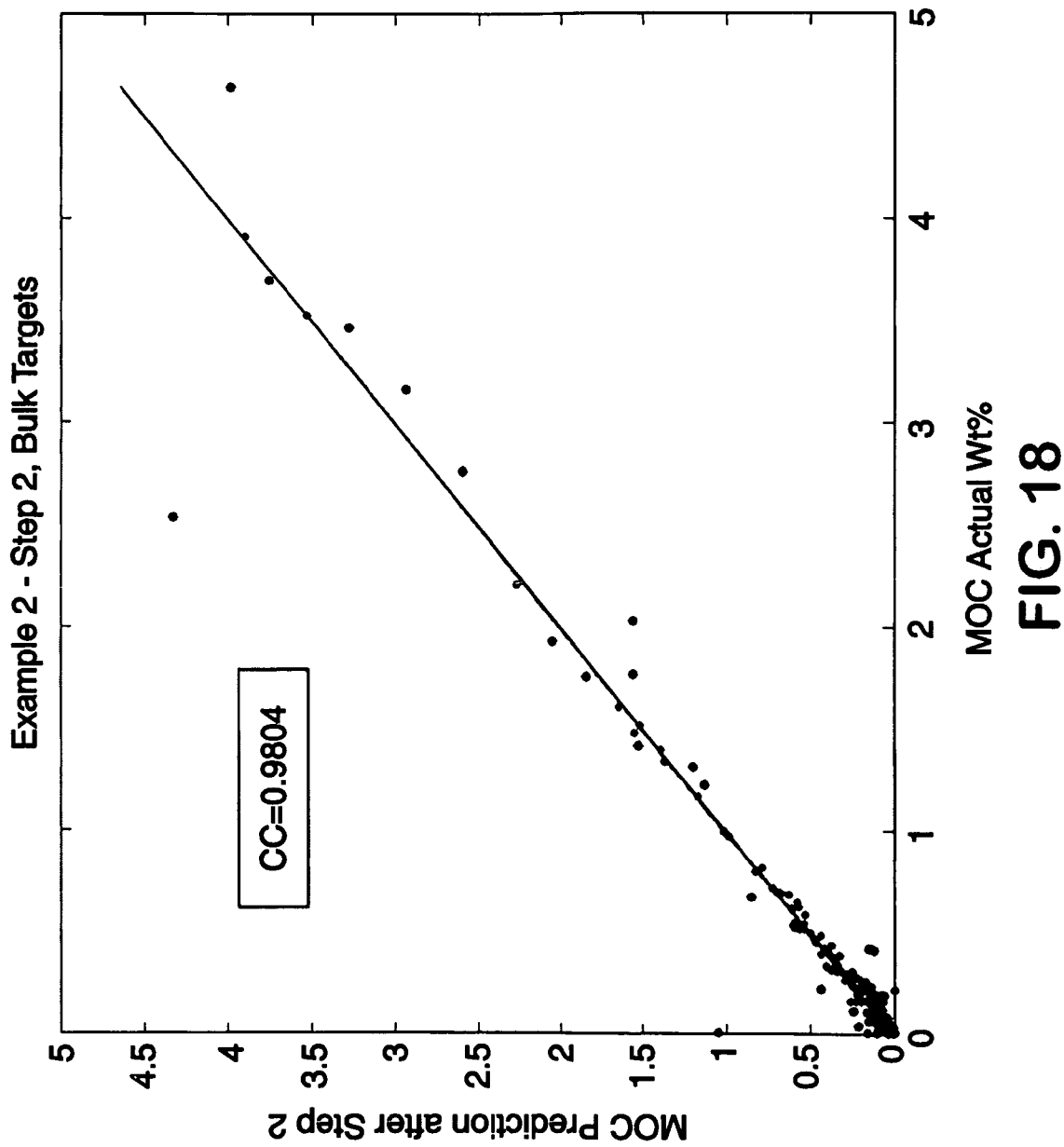
FIG. 18 shows a parity plot comparing the MOC for Example 2, Step 2 using bulk targets to the measured MOC.
Figure 19:
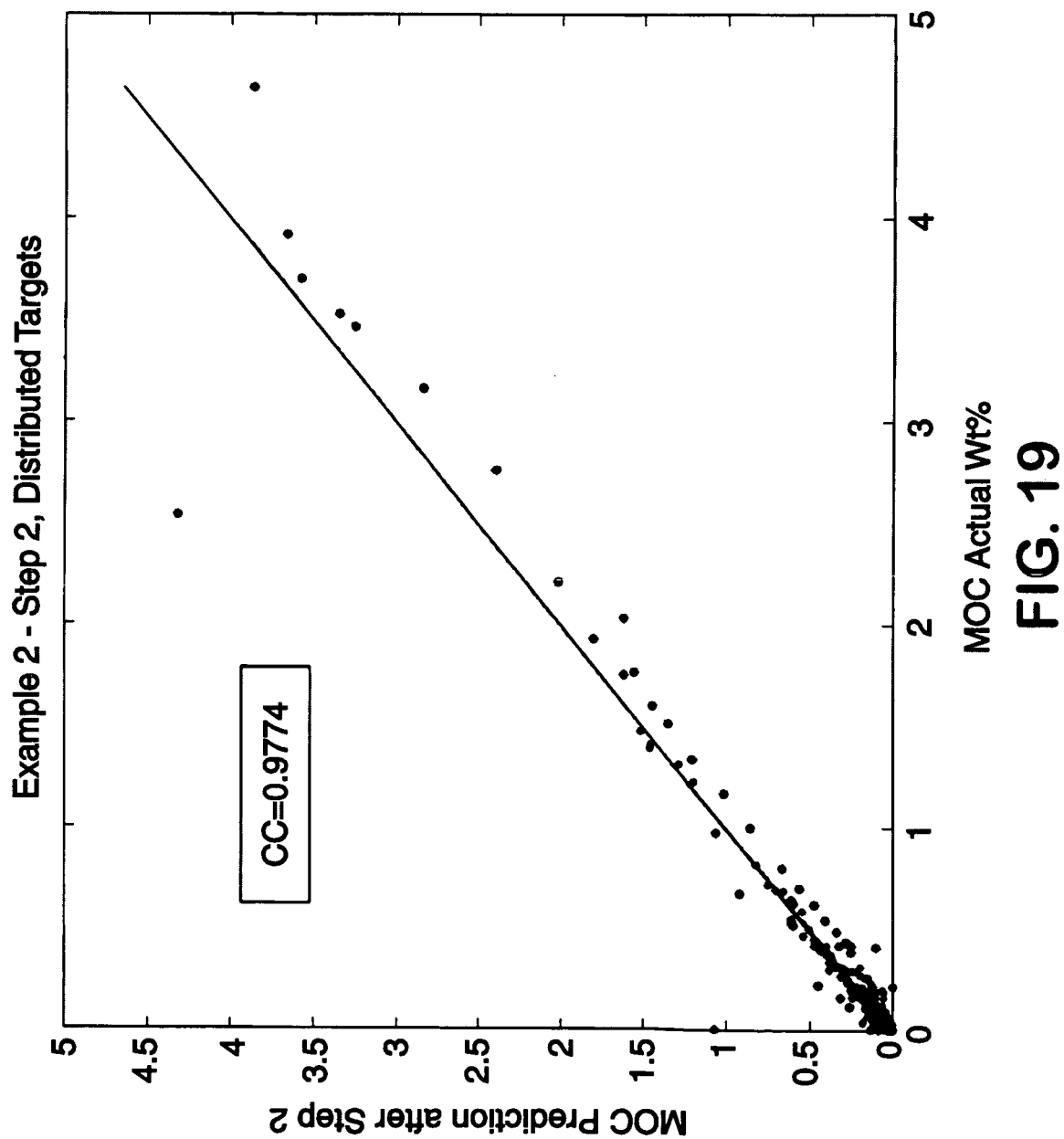
FIG. 19 shows a parity plot comparing the MOC for Example 2, Step 2 using distributed targets to the measured MOC.

FIGS. 18-19y show the weights for MOC results of step 2 synthesis to bulk and distributed properties respectively. In both cases, targets included gravity, boiling curve, sulfur, aliphatic sulfur, nitrogen and basic nitrogen. The synthesized models of composition are much closer matches to the measured model of composition, particularly with respect to the aromatics and sulfides. FIGS. 14-17 show property predictions for the various models of composition (dashed curves for Step 1 MOC, dash-dot curve for MOC after Step 2 synthesis with bulk property targets, and solid curve for MOC after Step 2 synthesis with distributed targets) compared to those based on the measured model of composition (open circles). Table 4 summarizes some key properties.

This example illustrates that while the reference selection procedure may sometimes suffer from lack of adequate references in the FTIR-HDHA library, it can, with the synthesis procedure, still estimate the composition to a reasonable degree of accuracy. Given the cost of generating the MOC reference data, this extended applicability increases the value of this two step procedure relative to that of Step 1 (U.S. Pat. No. 6,662,116) alone.

TABLE 4

| | Actual | Blended Reference | Tuned to Bulk Targets | Tuned to Dist Targets |
|---|---|---|---|---|
| API | 39.99 | 37.7 | 39.98 | 38.93 |
| SAT wt % | 88.7 | 82.1 | 88.6 | 86.6 |
| n-PAR wt % | 22.16 | 20.97 | 24.35 | 22.45 |
| i-PAR wt % | 28.46 | 20.6 | 23.89 | 21.87 |
| Naphthenes | | | | |
| 1-ring | 23.06 | 23.79 | 24.49 | 24.94 |
| 2-ring | 11.04 | 11.65 | 11.12 | 11.94 |
| 3-ring | 3.36 | 411 | 3.84 | 4.26 |
| 4-ring | 0.41 | 0.76 | 0.72 | 0.87 |
| 5-ring | 0.12 | 0.21 | 0.18 | 0.24 |
| 6-ring | 0.060 | 0.030 | 0.020 | 0.020 |
| S wt % | 0.030 | 0.170 | 0.030 | 0.030 |
| aliph S wt % | 0.010 | 0.050 | 0.010 | 0.010 |
| tot N ppm | 53.330 | 144.070 | 53.410 | 53.770 |
| basic N ppm | 18.840 | 36.700 | 20.200 | 18.910 |
| H2 wt % | 14.140 | 13.740 | 14.170 | 14.040 |
| POLAR wt % | 0.060 | 0.120 | 0.060 | 0.070 |
| ARO + SUL wt % | 11.27 | 17.77 | 11.33 | 13.34 |
| ARC1 | 6.13 | 9.36 | 7.18 | 8.06 |
| ARC2 | 3.32 | 5.08 | 2.72 | 3.47 |
| ARC3 | 1.31 | 2.15 | 1.09 | 1.35 |
| ARC4 | 0.4 | 0.73 | 0.27 | 0.36 |
| RI@70 | 1.4384 | 1.4448 | 1.4377 | 1.4405 |
| % CA | 5.45 | 9.16 | 4.95 | 5.99 |
| pour pt C. | 35.3 | 16.4 | 24.5 | 21.6 |
| cloud pt C. | 57.3 | 38.8 | 43.5 | 41.6 |
| freeze pt C. | 57.3 | 38.8 | 43.5 | 41.6 |
| TAN mg/g | 0 | 0.1 | 0 | 0 |

EXAMPLES 3-7

For examples 3-7, a library of 705 process stream samples was used. These samples are kerosene and gasoil range materials which are feeds and products of various refinery processes. For each of the 705 samples, an FT-IR spectrum was collected covering the 5000-400 cm$^{-1}$ range using a 0.25 mm fixed path flow cell with CaF$_2$ windows. Samples were maintained at 65° C. during spectral data collection. For each sample in the library, HDHA was measured, as were various bulk properties including but not limited to API gravity, SimDis, sulfur, aliphatic sulfur, nitrogen, and basic nitrogen. The HDHA of the reference samples were tuned to the measured bulk properties.

A cross-validation analysis was conducted in which each of the 705 samples were taken out of the library and treated as an unknown, being analyzed relative to the remaining 704 samples. The analyses were conducted in two modes: (1) in the IR-Only mode, the FT-IR spectrum of the unknown was fit as a linear combination of the remaining 704 spectra over the spectral ranges from 4998.6-3139.5 cm$^{-1}$, 2760.6-2400.9 cm$^{-1}$, 2200.4-1636.3 cm$^{-1}$ and 1283.4-925.7 cm$^{-1}$. Spectral data in the 3139.5-2760.6 cm$^{-1}$ and 1636.3-1283.4 cm$^{-1}$ ranges was not used since the absorbances in these ranges exceeded the linear response range of the FT-IR detector. Data in the 2400.9-2200.4 cm$^{-1}$ range was not used to avoid interferences from atmospheric carbon dioxide, and data below 925.7 cm$^{-1}$ was not used because of poor signal-noise near the CaF$_2$ cell window cutoff. The spectra were orthogonalized to baseline, water vapor and liquid water corrections as described in U.S. Pat. No. 6,662,116. The fit was obtained using a nonnegative least squares algorithm. (2) in the IR-Bulk mode, the FT-IR spectrum of the unknown was augmented with volumetrically blendable data for API (specific) gravity, SimDis and sulfur, and fit as a linear combination of reference spectra which are similarly augmented. SimDis data was converted to wt % evaporated at fixed temperature which is multiplied by sample specific gravity so as to be volumetrically blendable. Sulfur wt % is multiplied by specific gravity so as to be volumetrically blendable. For the IR-Bulk mode, the spectral ranges used are the same as for the IR-Only mode, and the spectral data is orthogonalized to the same corrections. The weights for the augmented properties relative to the FT-IR data were optimized as described in Appendix D. Fits were calculated using a nonnegative linear least squares algorithm.

EXAMPLE 3

Figure 20:
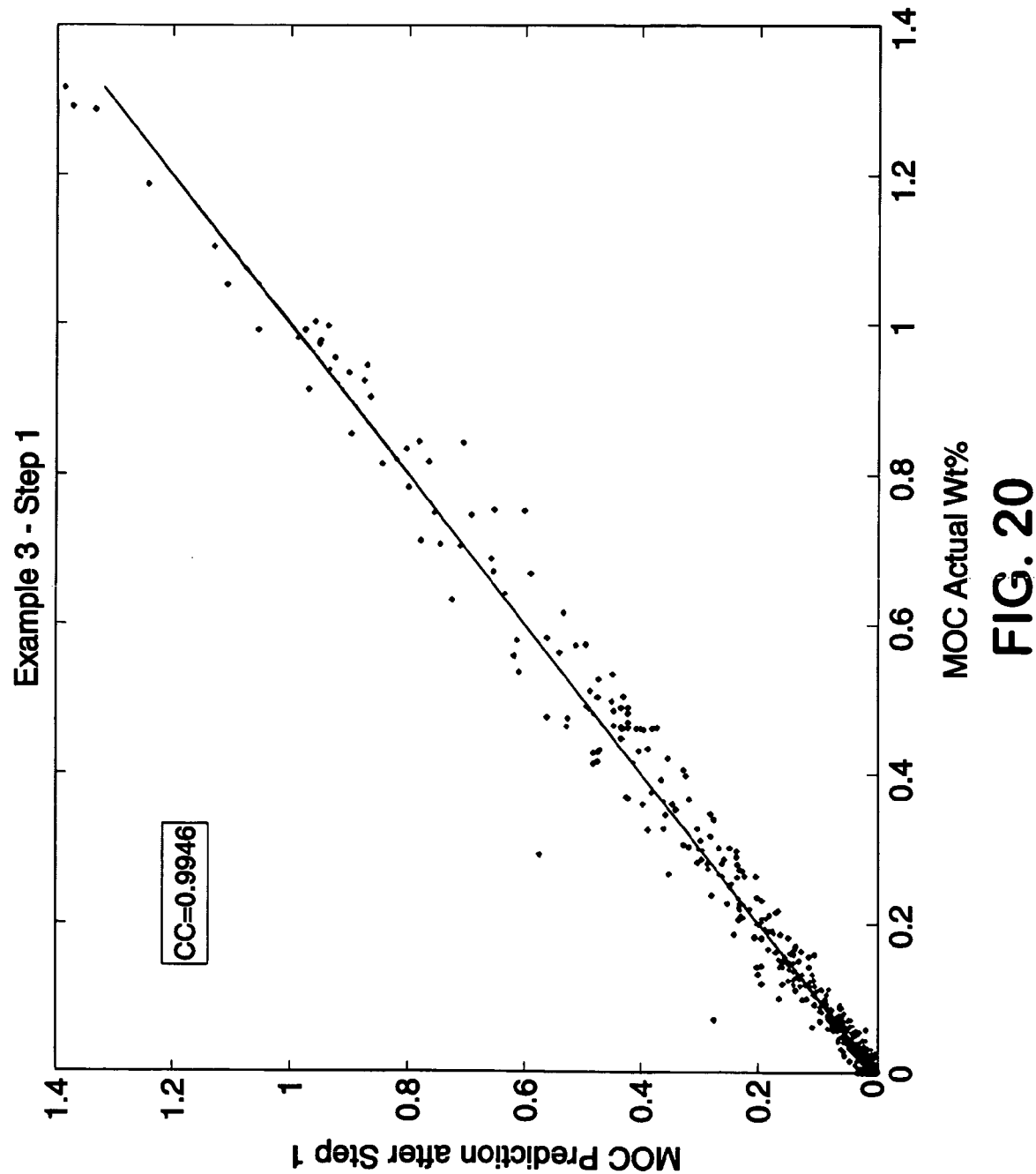
FIG. 20 shows a parity plot comparing the MOC for Example 3, Step 1 to the measured MOC.
Figure 21:
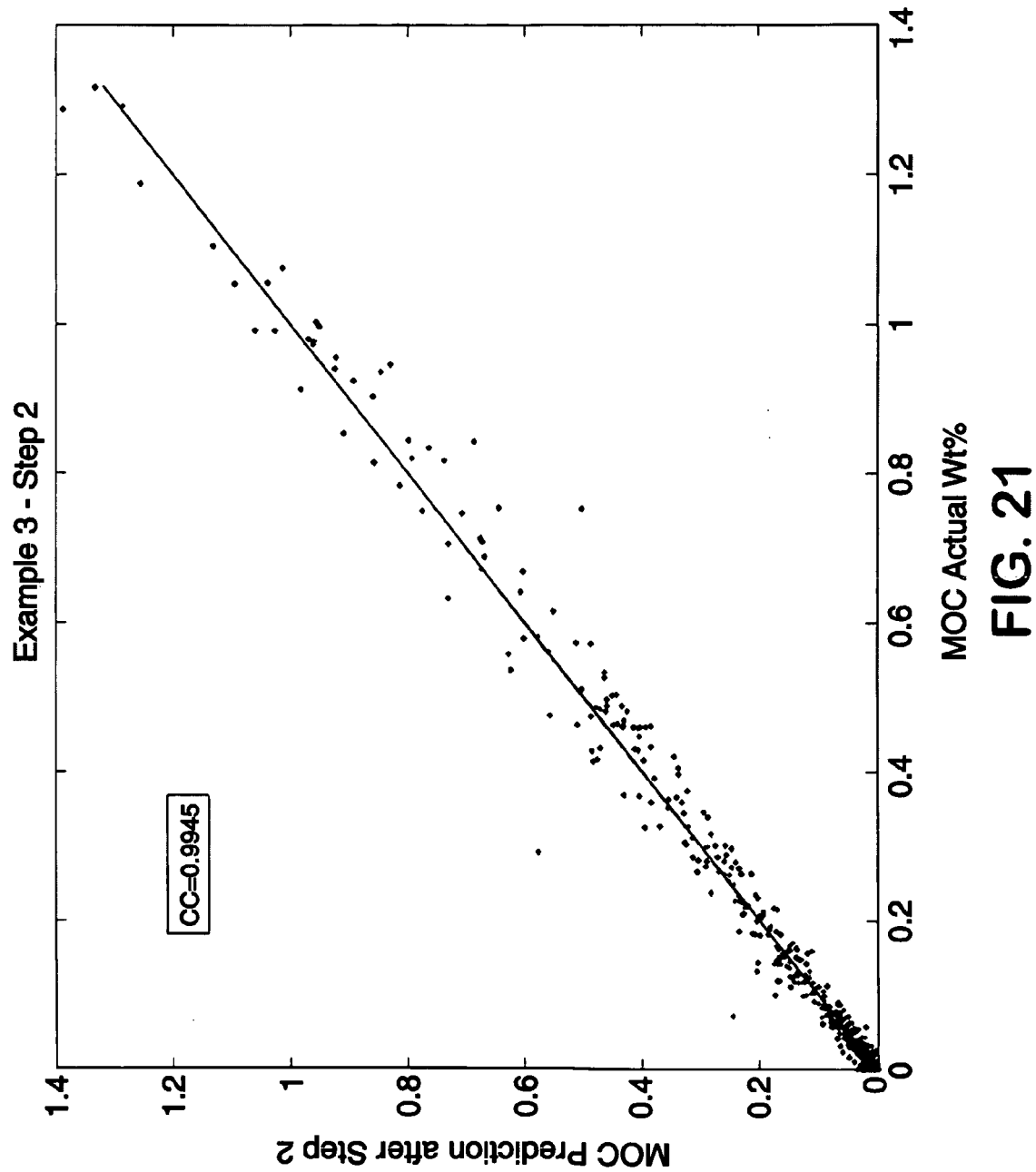
FIG. 21 shows a parity plot comparing the MOC for Example 3, Step 2 to the measured MOC.
Figure 22:
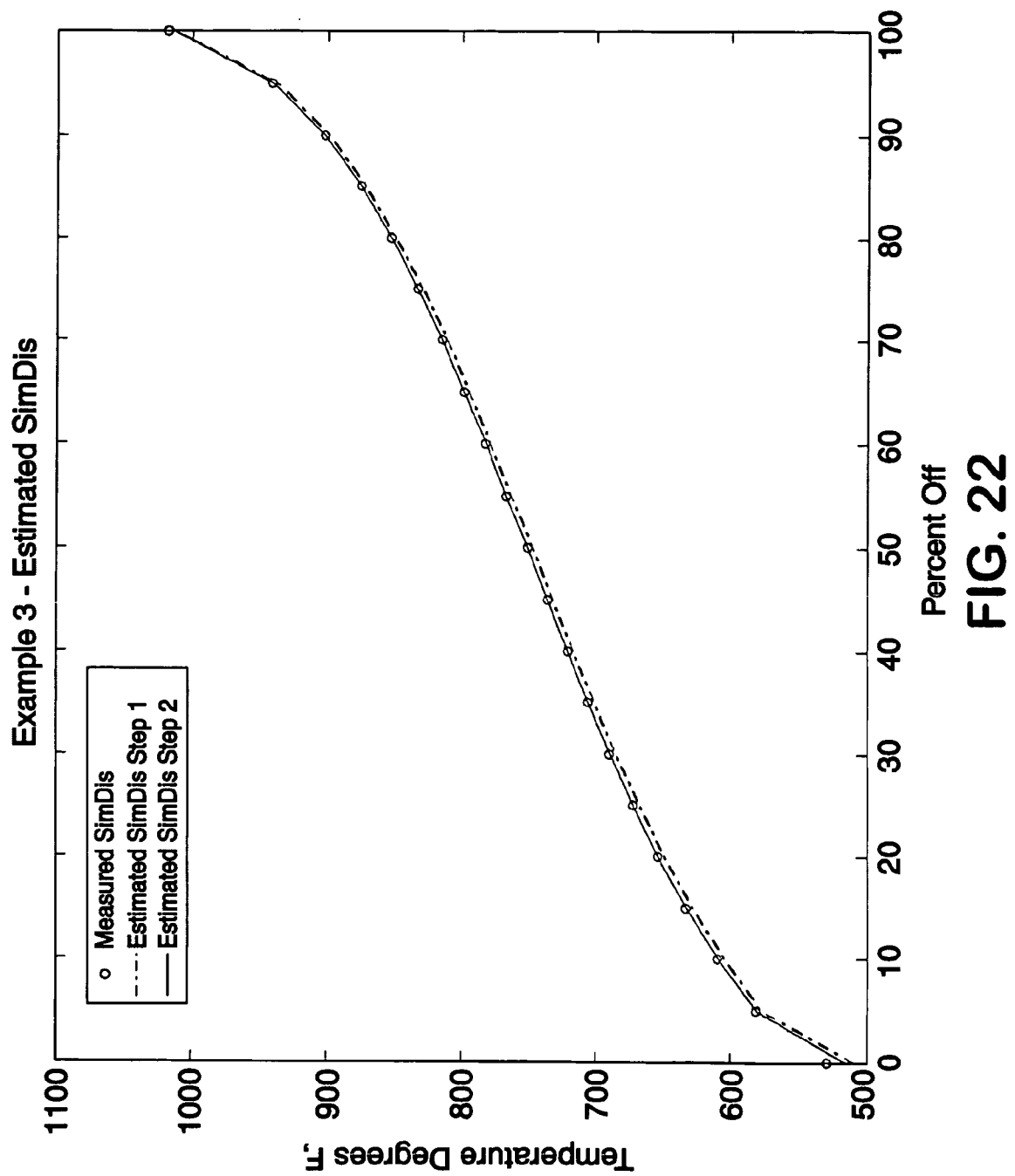
FIG. 22 compares the distillation calculated from the MOC of Example 3, Step 1 and Step 2 to the measured distillation.

Step 1: A spectrum of a gas oil product from a hydrocracking unit (hydrocrackate) was analyzed in the IR-only mode. The spectrum of the gas oil was fit as a linear combination of 14 reference spectra from the library as shown in 28 to produce the blend in Table 5. Because of the relatively high number of other hydrocrackate references in the library, this spectrum can be extremely well fit, giving an FQR value of 0.48. The composition estimated from Step 1 is a very good reference for the measured composition as shown in FIG. 20, but there is a slight difference between the API and SimDis calculated from the blend and that measured for the sample. In step 2, this reference composition is tuned to the API and SimDis to give the final composition shown in Table 6 and FIG. 21. Note that since the sample contains no sulfur, sulfur did not need to be used as a target in the tuning process.

TABLE 5

Blend for IR-Only Analysis of Hydrocracker Product

| Component | Volume Percent |
| --- | --- |
| Coker Naphtha | 0.07 |
| Diesel Fuel | 1.08 |
| Gofinate | 0.14 |
| Hydrocrackate | 12.00 |
| Hydrocrackate | 18.00 |
| Hydrocrackate | 35.44 |
| Hydrocrackate | 3.73 |
| Hydrocrackate | 25.28 |
| Hydrocrackate | 3.30 |
| Coker Gas Oil | 0.12 |
| FCC Feed | 0.30 |
| Hydrocracker Feed | 0.34 |
| Crude Vacuum Gas Oil | 0.14 |
| Lubes Extract | 0.08 |

TABLE 6

| | Actual | Step 1 Blended Reference | Step 2 Tuned to Bulk Targets |
| --- | --- | --- | --- |
| API | 27.6 | 27.8 | 27.6 |
| SAT wt % | 70.16 | 69.87 | 69.77 |
| Total Paraffins | 17.31 | 18.4 | 18.24 |
| Total Naphthenes | 52.86 | 51.44 | 51.51 |
| Total Aromatics | 29.84 | 30.15 | 30.25 |
| S wt % | 0.00 | 0.00 | 0.00 |
| aliph S wt % | 0.00 | 0.00 | 0.00 |
| tot N ppm | 19 | 34 | 38 |
| basic N ppm | 5 | 10 | 11 |
| ARC1 | 22.87 | 23.12 | 22.93 |
| ARC2 | 4.01 | 4.38 | 4.49 |
| ARC3 | 1.11 | 1.15 | 1.2 |
| ARC4 | 0.98 | 1.16 | 1.25 |
| POLAR wt % | 0.87 | 0.32 | 0.35 |
| SimDist D2887 | | | |
| IBP | 529 | 510 | 517 |
| 10% Off | 610 | 604 | 609 |
| 30% Off | 690 | 685 | 689 |
| 50% Off | 751 | 747 | 751 |
| 70% Off | 815 | 811 | 815 |
| 90% Off | 902 | 899 | 903 |
| EP | 1018 | 1012 | 1013 |

EXAMPLE 4

Figure 23:
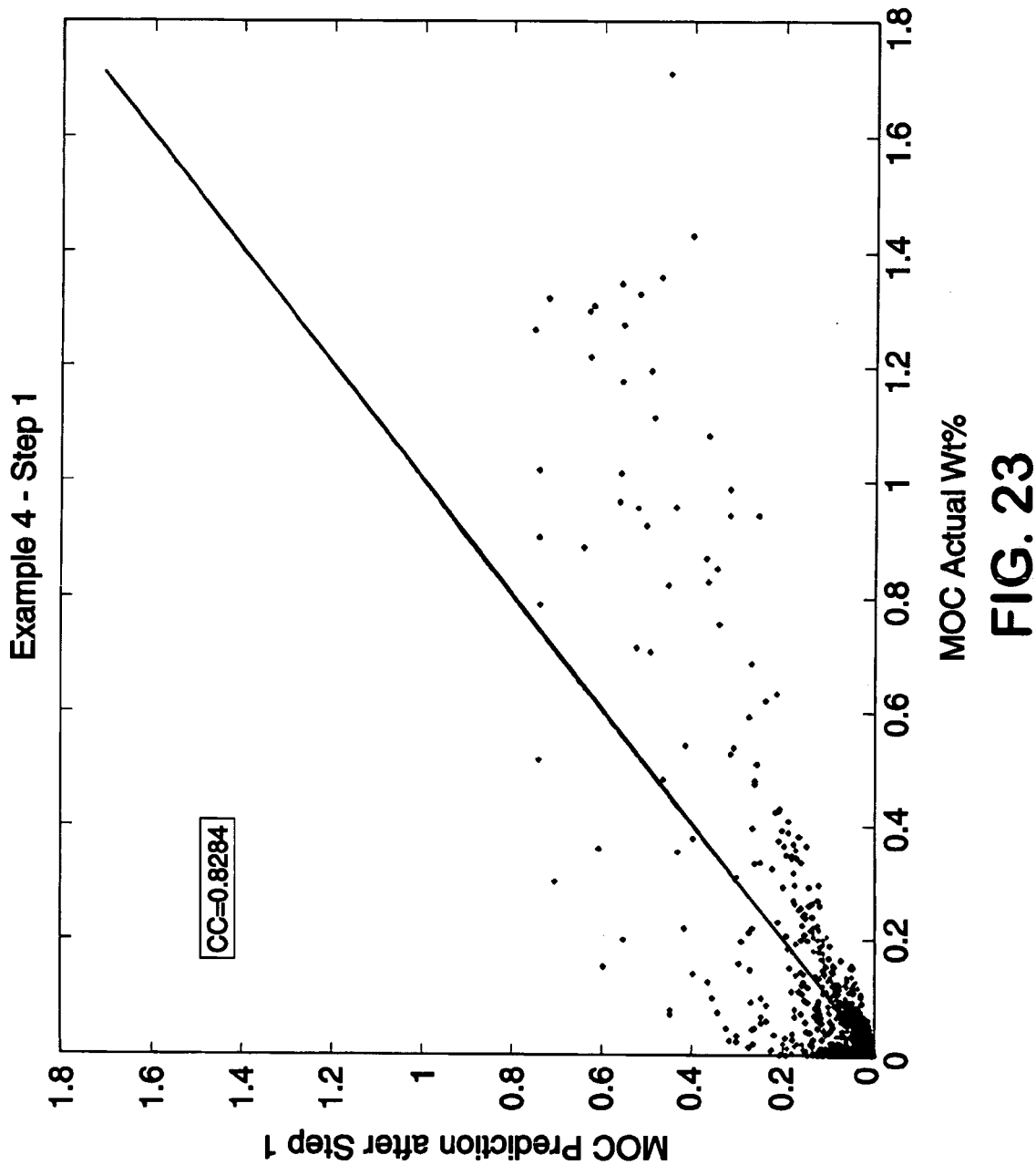
FIG. 23 shows a parity plot comparing the MOC for Example 4, Step 1 to the measured MOC.
Figure 24:
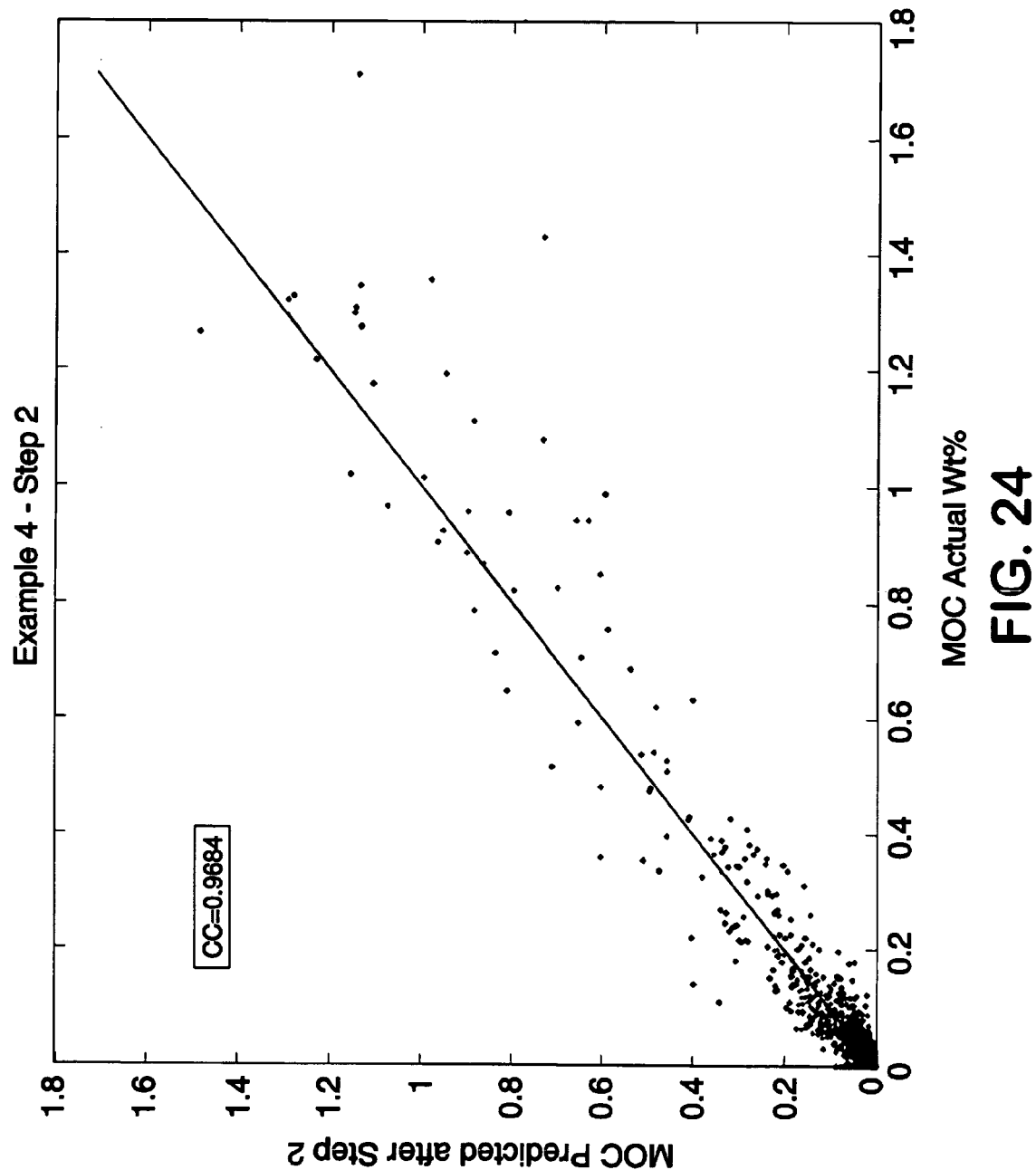
FIG. 24 shows a parity plot comparing the MOC for Example 4, Step 2 to the measured MOC.
Figure 25:
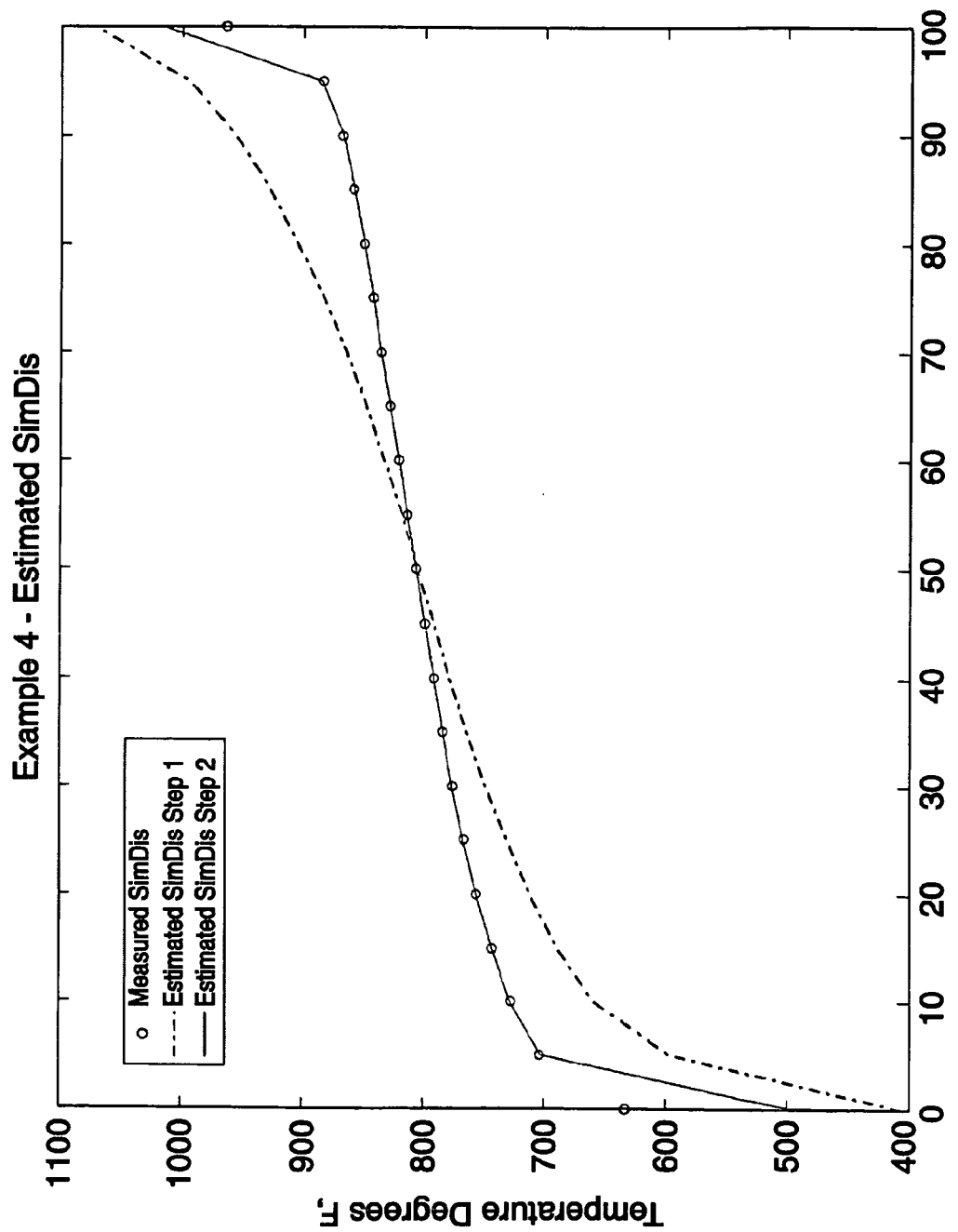
FIG. 25 compares the distillation calculated from the MOC of Example 4, Step 1 and Step 2 to the measured distillation.

A M100 gas oil was analyzed using the IR-only mode. In Step 1, the spectrum of the gas oil was fit as a blend of the spectra of 23 references. The FQR for the fit was 0.96 indicating that the blend is a good match to the functionality of the sample. However, since the IR is not overly sensitive to molecular weight, the reference composition that is estimated differs significantly from the measured composition for the gas oil (Table 7 and FIG. 23), particularly in terms of boiling point distribution (FIG. 25, dash-dot line). However, once this reference composition is synthesized to API gravity, SimDis and sulfur targets in Step 2, the estimated composition is in good agreement with the measured composition as shown in FIG. 24. The distillation estimated from the 2nd step MOC (FIG. 25, dashed line) now agrees closely with that measured (open circles). The two step procedure of the current invention clearly provides a superior MOC relative to the one derived from the blended reference alone.

TABLE 7

| | Actual | IR-Only Step 1 Blended Reference | IR-Only Step 2 Tuned to Bulk Targets | IR-Bulk Step 1 Blended Reference | IR-Bulk Step 2 Tuned to Bulk Targets |
| --- | --- | --- | --- | --- | --- |
| API | 23.8 | 23.7 | 23.8 | 23.6 | 23.8 |
| SAT wt % | 54.17 | 50.43 | 52.74 | 57.79 | 58.46 |
| Total Paraffins | 26.71 | 21.68 | 23.15 | 23.71 | 24.21 |
| Total Naphthenes | 27.46 | 28.73 | 29.58 | 33.86 | 34.03 |
| Total Aromatics | 45.83 | 49.6 | 47.27 | 42.43 | 41.76 |
| S wt % | 1.56 | 1.48 | 1.56 | 1.49 | 1.56 |
| aliph S wt % | 0.49 | 0.52 | 0.57 | 0.40 | 0.41 |
| tot N ppm | 1197 | 1139 | 1150 | 991 | 929 |
| basic N ppm | 359 | 333 | 281 | 257 | 231 |
| ARC1 | 17.97 | 20.13 | 19.66 | 16.52 | 16.31 |
| ARC2 | 14.59 | 15.11 | 14.02 | 11.88 | 11.85 |
| ARC3 | 6.12 | 7.05 | 6.96 | 5.89 | 5.91 |
| ARC4 | 3.48 | 3.67 | 3.67 | 4.97 | 4.85 |
| POLAR wt % | 3.67 | 6.61 | 2.96 | 2.95 | 2.62 |
| SimDist D2887 | | | | | |
| IBP | 633 | 407 | 498 | 611 | 624 |
| 10% Off | 728 | 660 | 729 | 719 | 728 |
| 30% Off | 776 | 749 | 776 | 771 | 776 |
| 50% Off | 806 | 805 | 806 | 804 | 806 |
| 70% Off | 836 | 865 | 836 | 836 | 836 |
| 90% Off | 869 | 956 | 968 | 878 | 868 |
| EP | 963 | 1072 | 1016 | 988 | 951 |

EXAMPLE 5

Figure 26:
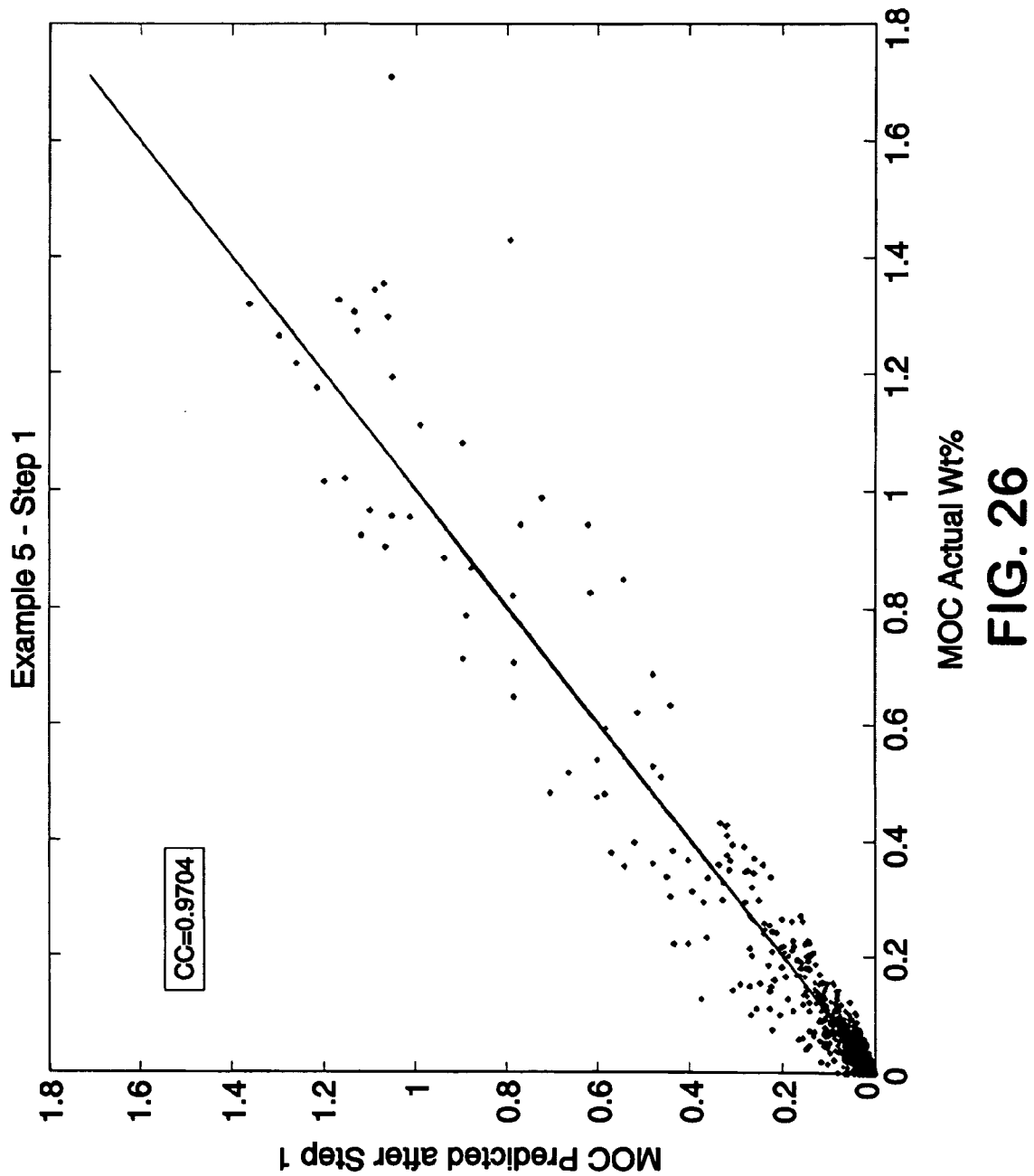
FIG. 26 shows a parity plot comparing the MOC for Example 5, Step 1 to the measured MOC.
Figure 27:
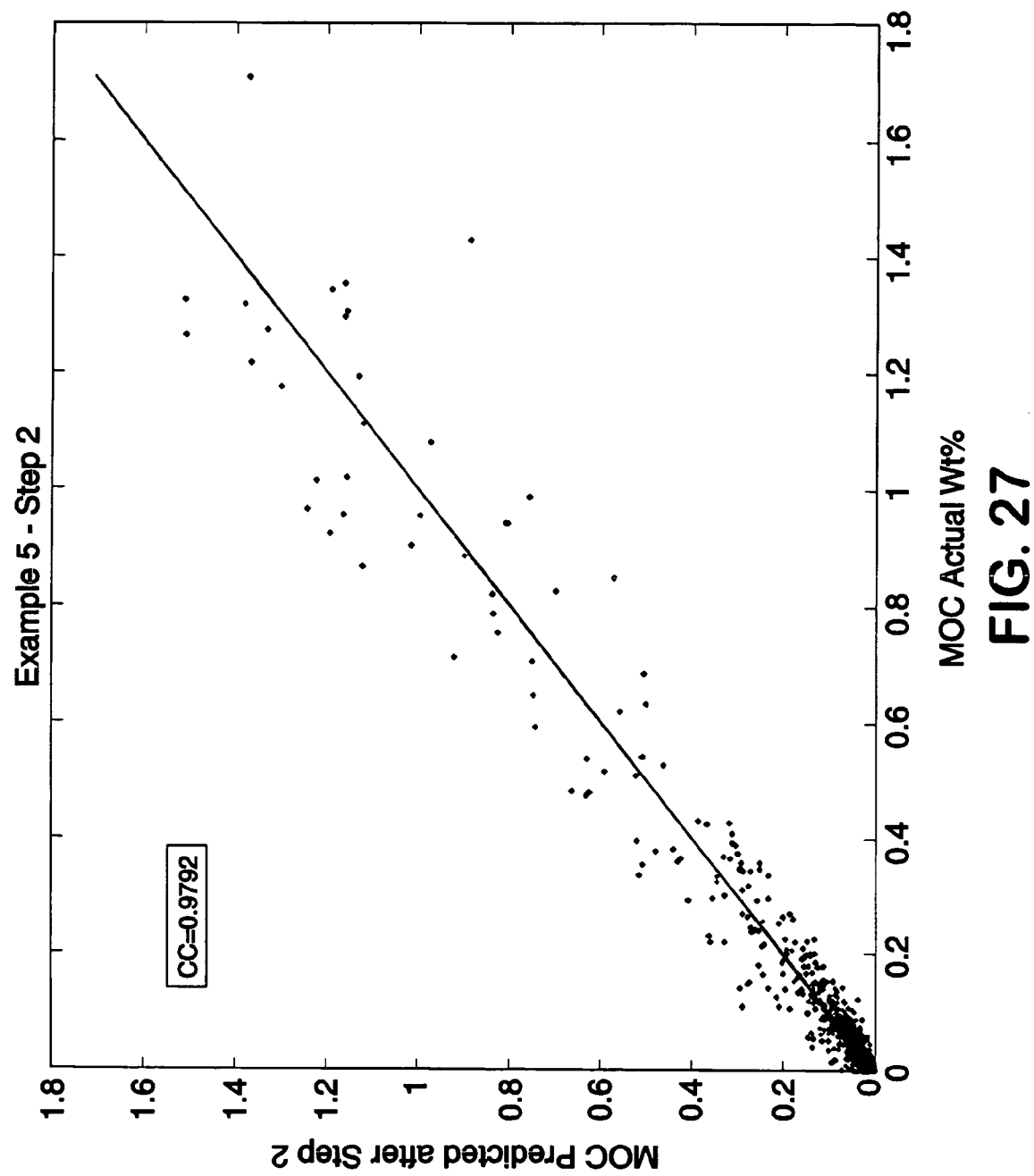
FIG. 27 shows a parity plot comparing the MOC for Example 5, Step 2 to the measured MOC.

The same gas oil from Example 4 was analyzed using the IR-Bulk mode, wherein the FT-IR spectrum was augmented with API gravity, SimDis and sulfur. A blend of 12 references was obtained, the FQR for the fit of 0.95 indicating a good match to the composition. With the use of these bulk properties in the blend calculation, the molecular weight distribution of the reference from Step 1 is a much better match to that measured for the gas oil as shown in Table 7 and by comparison of FIG. 26 to FIG. 23, and the estimated composition after Step 2 is again in good agreement with that measured for the gas oil (FIG. 27).

EXAMPLE 6

Figure 28:
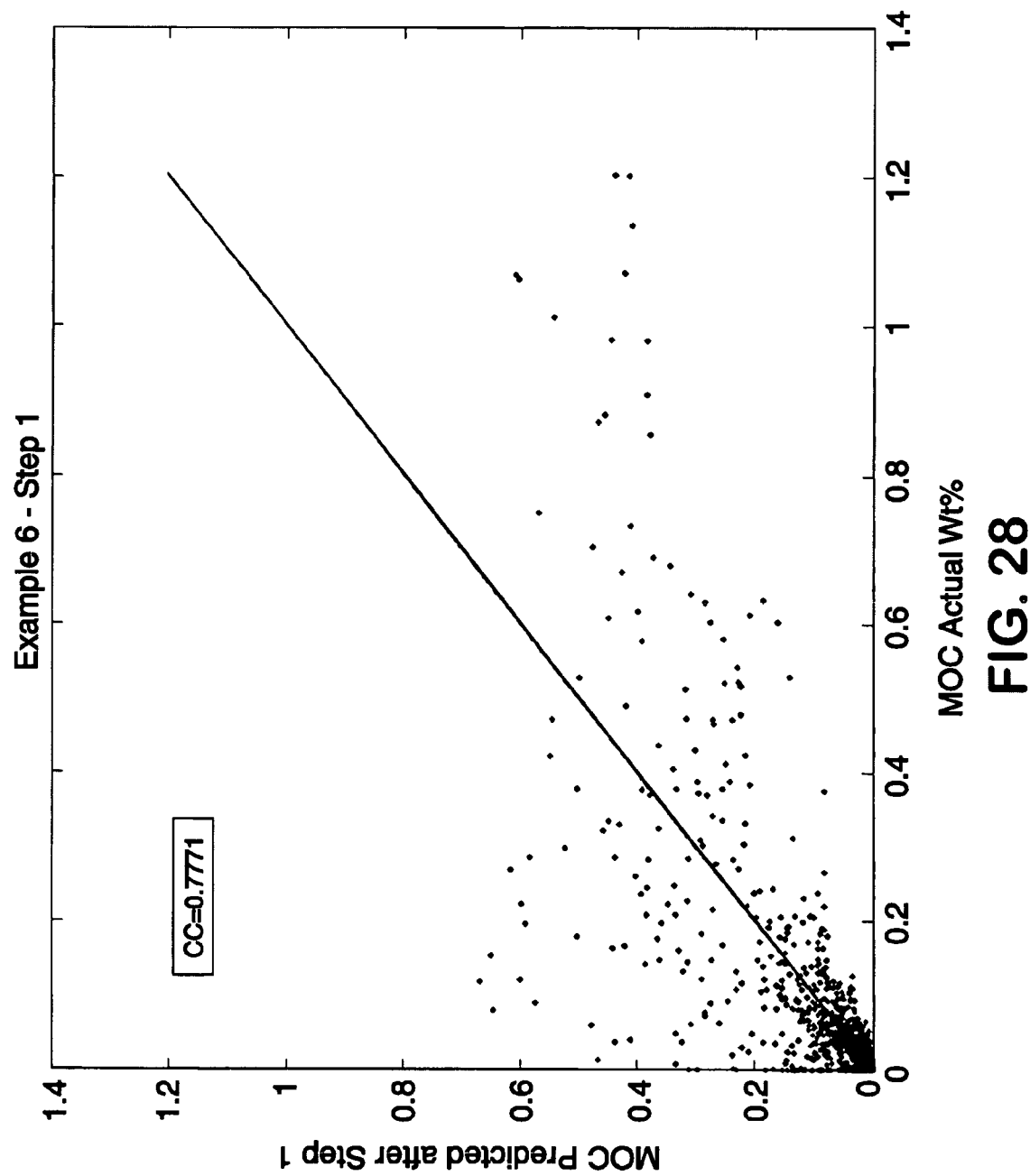
FIG. 28 shows a parity plot comparing the MOC for Example 6, Step 1 to the measured MOC.
Figure 29:
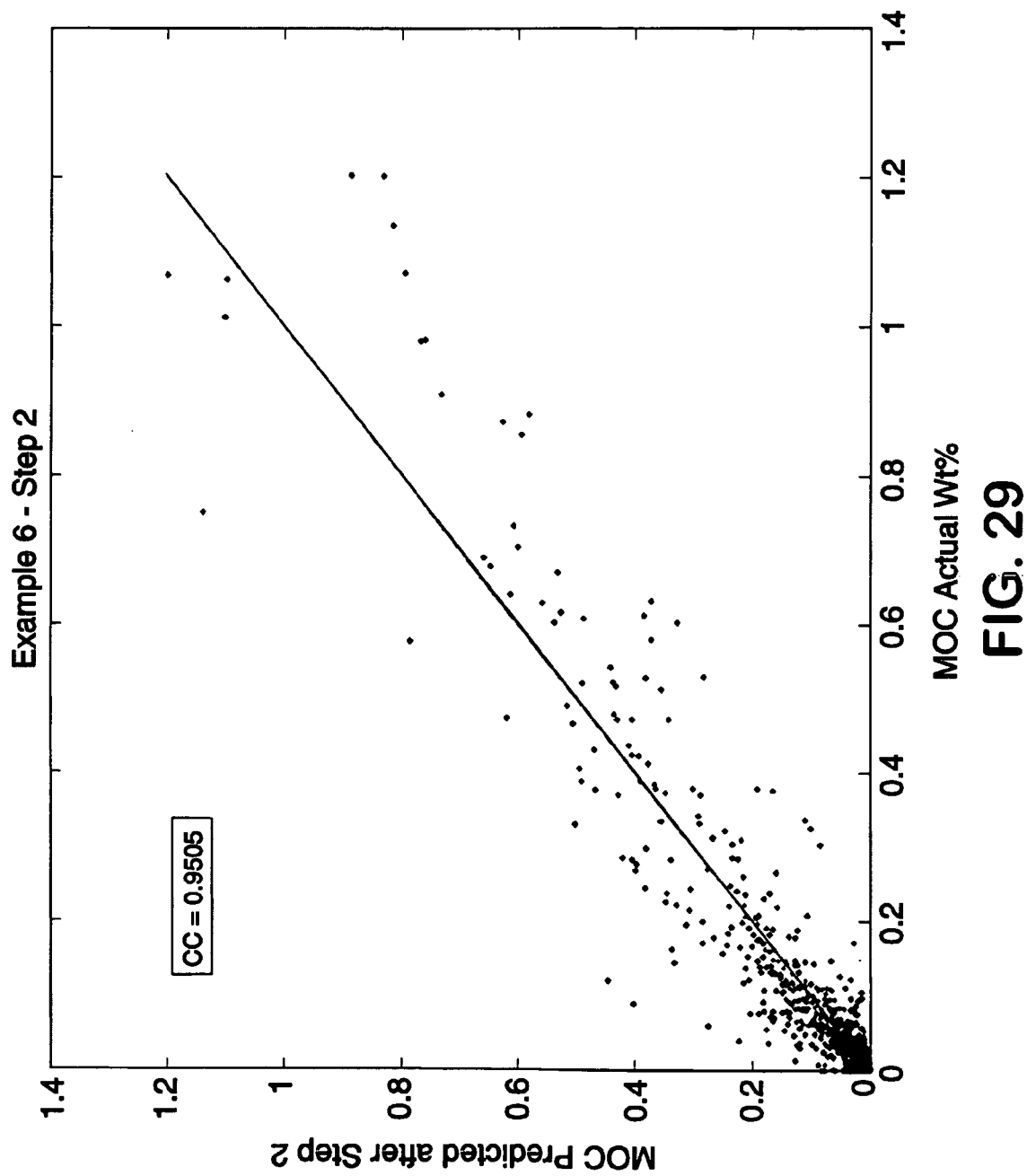
FIG. 29 shows a parity plot comparing the MOC for Example 6, Step 2 to the measured MOC.
Figure 30:
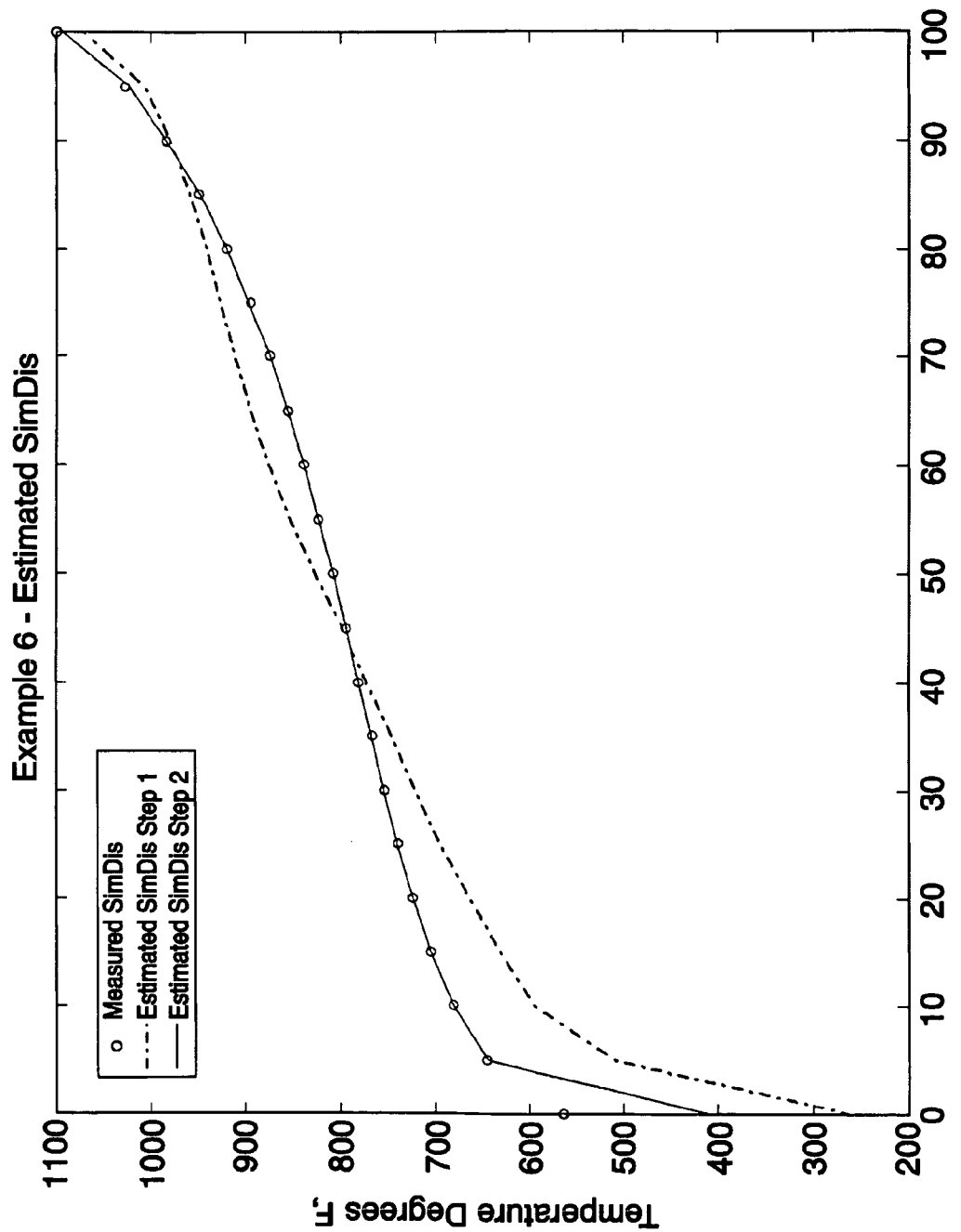
FIG. 30 compares the distillation calculated from the MOC of Example 6, Step 1 and Step 2 to the measured distillation.

A vacuum gas oil was analyzed using the IR-only mode, yielding from Step 1 a blend of blend of 25 references and an FQR of 2.26. The high FQR value indicates that the gas oil is fairly dissimilar to the references in the library, and in fact the reference composition agrees poorly with the measured composition (Table 8 and FIG. 28). The Step 2 synthesis is performed using API gravity, SimDis and Sulfur targets to give the composition shown in Table 8 and FIG. 29. Despite the relatively poor reference, the synthesized composition is in relatively good agreement with the measured composition. Again, the two step procedure of the current invention produces a significantly better MOC than the one step blended reference.

TABLE 8

|  | Actual | IR-Only Step 1 Blended Reference | IR-Only Step 2 Tuned to Bulk Targets |
|---|---|---|---|
| API | 23.6 | 24.5 | 23.6 |
| SAT wt % | 56.78 | 56.38 | 55.97 |
| Total Paraffins | 32.51 | 29.01 | 30.3 |
| Total Naphthenes | 23.34 | 26.77 | 25.32 |
| Total Aromatics | 44.15 | 44.22 | 44.38 |
| S wt % | 1.36 | 1.25 | 1.36 |
| aliph S wt % | 0.24 | 0.20 | 0.20 |
| tot N ppm | 639 | 756 | 951 |
| basic N ppm | 146 | 139 | 155 |
| ARC1 | 12.9 | 15.48 | 13.38 |
| ARC2 | 9.12 | 10.08 | 9.70 |
| ARC3 | 9.32 | 6.82 | 7.95 |
| ARC4 | 8.59 | 7.72 | 9.45 |
| POLAR wt % | 3.31 | 3.52 | 3.55 |
| SimDist D2887 | | | |
| IBP | 563 | 261 | 409 |
| 10% Off | 680 | 594 | 680 |
| 30% Off | 754 | 722 | 754 |
| 50% Off | 807 | 826 | 807 |
| 70% Off | 873 | 910 | 874 |
| 90% Off | 983 | 978 | 983 |
| EP | 1100 | 1071 | 1092 |

EXAMPLE 7

Figure 31:
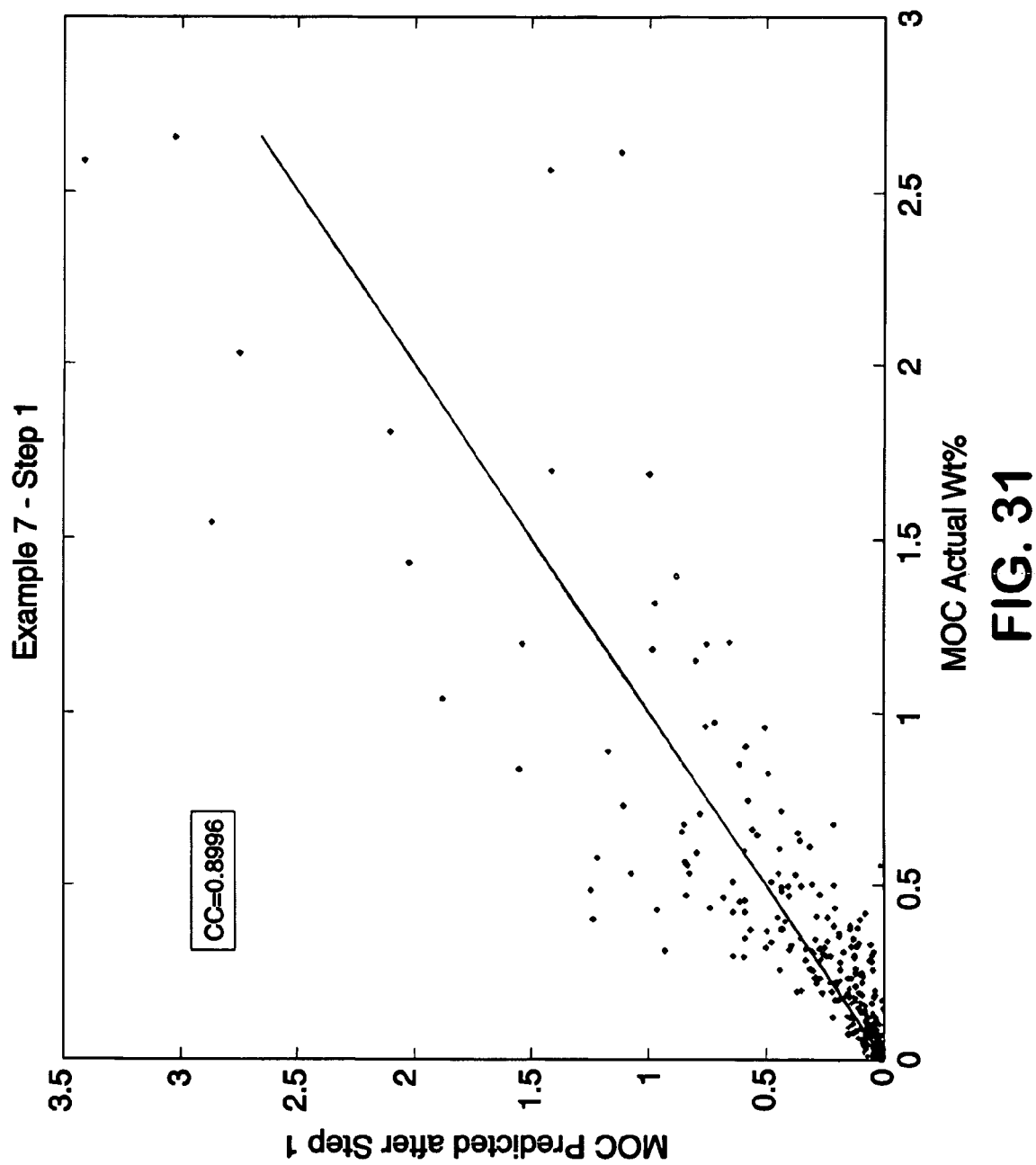
FIG. 31 shows a parity plot comparing the MOC for Example 7, Step 1 to the measured MOC.
Figure 32:
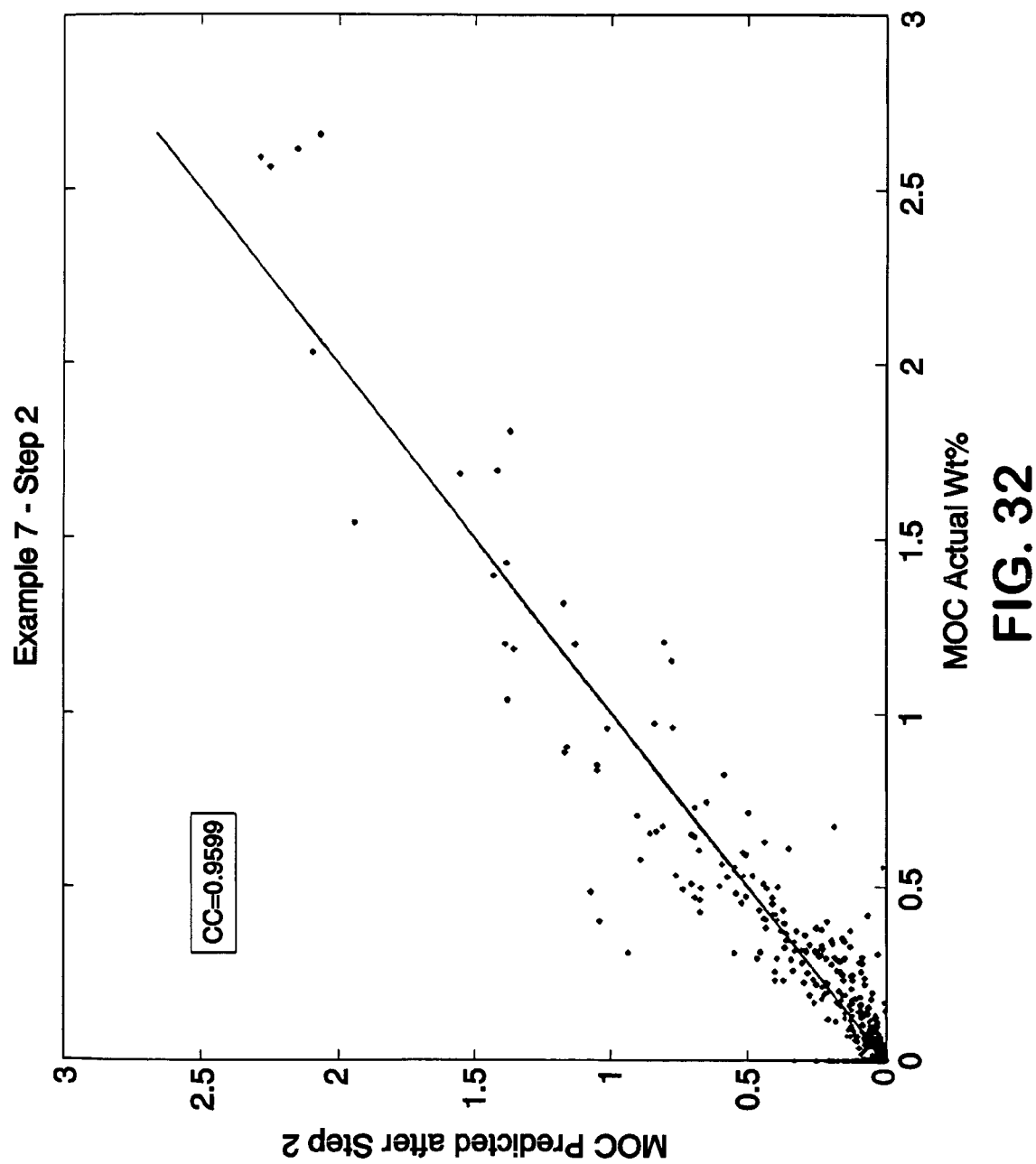
FIG. 32 shows a parity plot comparing the MOC for Example 7, Step 2 to the measured MOC.
Figure 33:
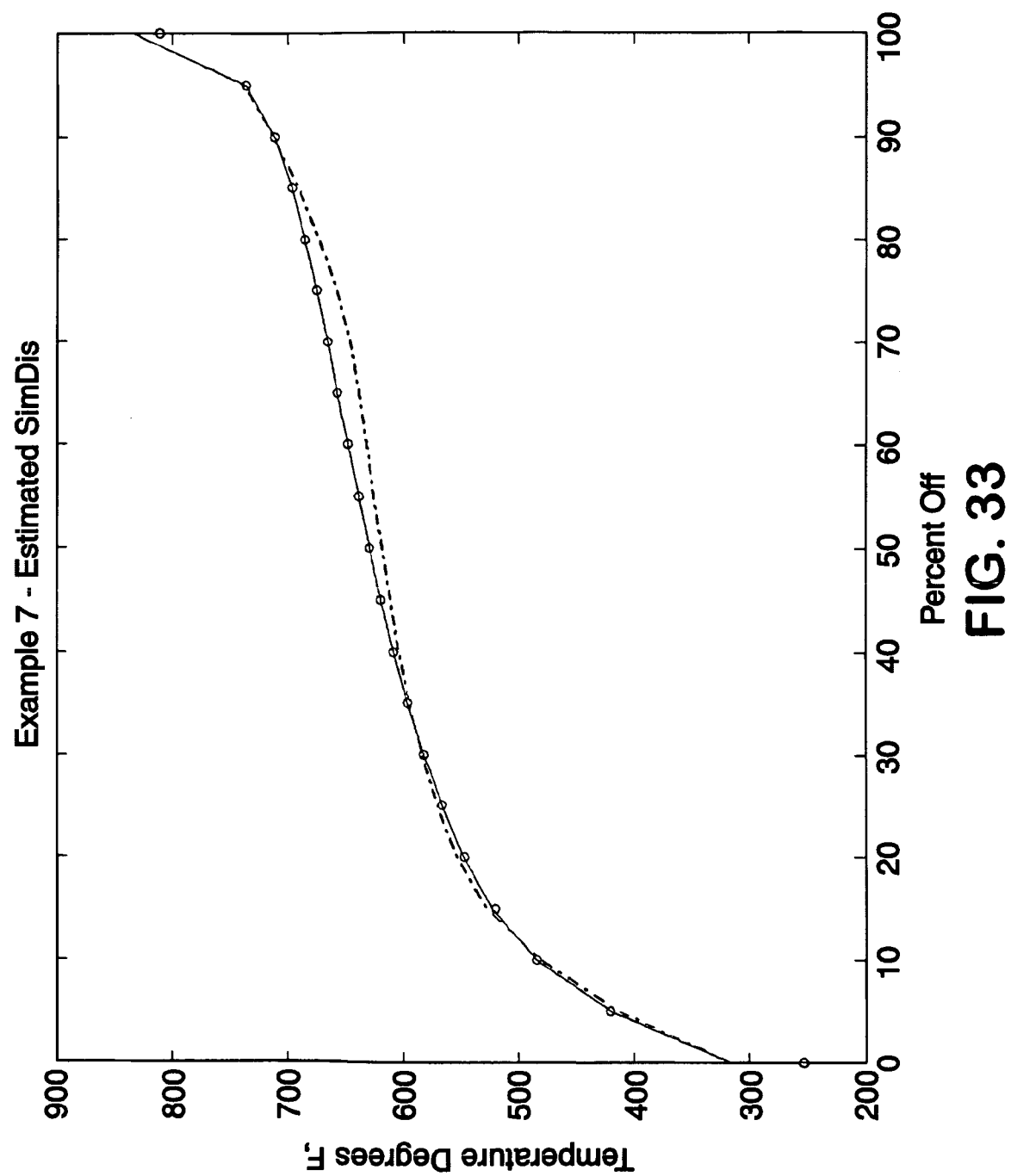
FIG. 33 compares the distillation calculated from the MOC of Example 7, Step 1 and Step 2 to the measured distillation.

A diesel fuel was analyzed using the IR-Bulk mode with the FT-IR spectrum augmented with API gravity, SimDis and sulfur. A blend of 14 references is calculated giving an FQR of 1.07. The fact that the FQR value is greater than 1 indicates that the diesel fuel is somewhat different than reference samples in the library, so that the sample composition cannot be matched well as a blend of these references. As seen in Table 9 and FIGS. 31 and 33, the molecular weight distribution and distillation for the reference blend from Step 1 is different from that measured. After the Step 2 synthesis is performed using API gravity, SimDis and sulfur as targets, the resultant composition (Table 9 and FIGS. 32 and 33) is in good agreement with that which was measured.

TABLE 9

|  | Actual | IR-Bulk Step 1 Blended Reference | IR-Bulk Step 2 Tuned to Bulk Targets |
|---|---|---|---|
| API | 29.4 | 29.4 | 29.4 |
| SAT wt % | 62.37 | 65.06 | 64.78 |
| Total Paraffins | 20.25 | 24.01 | 24.57 |
| Total Naphthenes | 42.12 | 40.80 | 39.94 |
| Total Aromatics | 37.63 | 35.20 | 35.49 |
| S wt % | 1.37 | 1.08 | 1.37 |
| aliph S wt % | 0.55 | 0.34 | 0.43 |
| tot N ppm | 190 | 204 | 194 |
| basic N ppm | 73 | 91 | 88 |
| ARC1 | 18.27 | 18.27 | 17.39 |

TABLE 9-continued

|  | Actual | IR-Bulk Step 1 Blended Reference | IR-Bulk Step 2 Tuned to Bulk Targets |
|---|---|---|---|
| ARC2 | 15.22 | 13.01 | 12.73 |
| ARC3 | 3.29 | 3.67 | 3.94 |
| ARC4 | 0.53 | 0.49 | 0.49 |
| POLAR wt % | 0.32 | 0.65 | 0.68 |
| SimDist D2887 | | | |
| IBP | 253 | 316 | 317 |
| 10% Off | 485 | 481 | 485 |
| 30% Off | 583 | 584 | 588 |
| 50% Off | 629 | 619 | 629 |
| 70% Off | 665 | 646 | 666 |
| 90% Off | 711 | 712 | 711 |
| EP | 811 | 833 | 834 |

Appendix A: Organizing the Model-of-Composition

The model-of-composition is organized initially into four major groups: saturates, aromatics, sulfides and polar molecules. Olefins are rare in crude petroleum, but are generated in refining processes that involve thermal or catalytic cracking and comprise a fifth major group. Within each major group, we organize molecules by homologous series. A homologous series is a molecular group that shares the same chemical structure (core), but has alkyl side chains of differing carbon number, arrangement and branching patterns. FIG. 34 shows the aromatic core structures for sample homologous series of benzene, naphthalene, fluorene, and dibenzothiophene.

It is convenient to organize hydrocarbon homologous series by hydrogen deficiency. Hydrogen deficiency can be organized into 14 classes (the primary x-classes) according to the formula:

$$x\text{-class} = (-14) + \mod(MW, 14). \quad \text{A1.}$$

The x-class is the remainder of the "nominal" molecular weight divided by 14. By convention the values −12, −13, −14 are replaced with 2 1 0 so x-class runs from −11 to 2. Although several homologous series present in petroleum share the same x-class, all molecules within each homologous series share the same x-class because the molecular weight of a —CH$_2$— group is 14.

Saturate Molecules

Saturate molecules contain only aliphatic carbons and hydrogen and their x-classes take the even integers −12, −10, −8, −6, −4, −2, 0 2. FIG. 35 show sample saturates arranged by x-class. Reading from right to left the molecules are 0 ring saturates, 1 ring saturates, 2 ring saturates etc. Notice that there are many similar (but related) molecules present in each x-class. These molecules are structural isomers sharing the identical mass and often very difficult to identify analytically in the complex mixture. A representative structure in each x-class (sometimes more than one) then becomes the model-of-composition. The preferred structures are shown in bold.

Aromatic Molecules

Aromatic molecules have carbon atoms in aromatic rings. Aromatic molecules found in petroleum often contain sulfur and non-basic nitrogen (—NH—) groups. We have organized aromatic molecules by ring class, i.e. 1, 2, 3 and 4+.

1 Ring Aromatic Molecules

FIG. 36 shows 1 ring aromatic cores arranged by x-class. Preferred structures are in bold. Some of these cores actually contain two aromatic rings separated by naphthenic rings or alkyl chains x-class −4, −2, 0 in FIG. 36) but are predominantly 1 ring in character. The alternate structures in x-class −4, −2, 0 have 4, 5 and 6 naphthenic rings, and are rare in petroleum. In the model-of-composition, thiophene is equivalent to an aromatic ring. Thiophenes x-class −4, −2, 0) are rare in crude petroleum, but are made in refining processes that involve thermal or catalytic cracking.

2 Ring Aromatic Molecules

Two ring aromatic cores shown in FIG. 37 have x-classes that take the even integers −10, −8, −6, −4, −2, 0, 2. Three of the preferred structures shown in bold are benzothiophenes x-classes −10, −8, −6). In the model-of-composition, a thiophene group is equivalent to an aromatic ring. Molecules containing the benzothiophene core x-class −6 in FIG. 37) are much more common in petroleum than those containing less preferred structure, phenylnaphthalene. Biphenyl cores x-class −2) are more abundant in petroleum than are tetrahydrophenanthrene cores. However, in hydroprocessed petroleum streams tetrahydrophenanthrenes are more abundant than are biphenyls.

Figure 38:
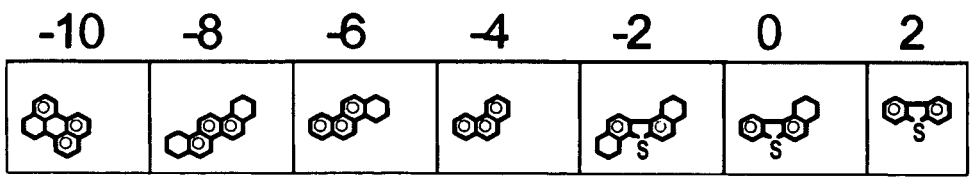
FIG. 38 shows 3-ring aromatic cores.

3 Ring Aromatic Molecules 3 ring aromatic cores shown in FIG. 38 have x-classes that take the even integers −10, −8, −6, −4, −2, 0, 2. Dibenzothiophenes x-classes −2, 0, 2), abundant in petroleum, have three-ring aromatic character. Phenanthrene and anthracene x-class −4) are both three-ring aromatics. Phenathrene is common in petroleum; anthracene is common in coal.

Figure 39:
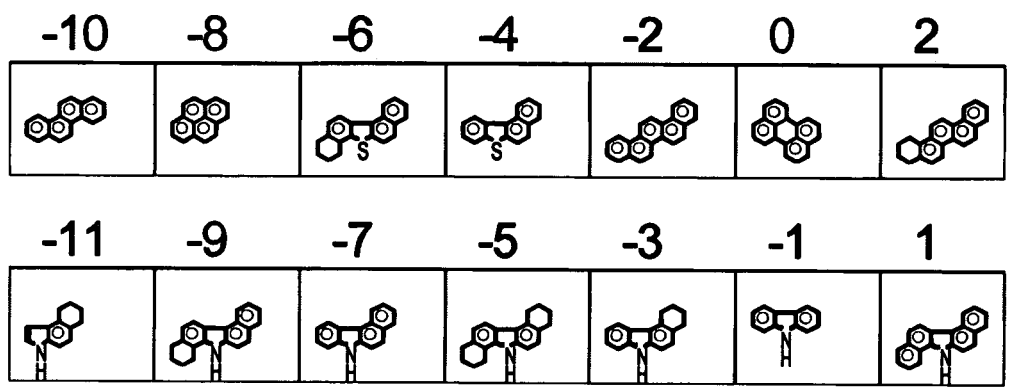
FIG. 39 shows 4-ring aromatic cores.

4 Ring Aromatic Molecules 4 ring aromatic cores shown in FIG. 39 have x-classes that take the even integers −10, −8, −6, −4, −2, 0, 2, and the odd integers −11, −9, −7, −5, −3, −1, 1. Each of the odd x-class cores contain a non-basic nitrogen group (—NH—). In the model-of-composition, all aromatic molecules that have non-basic nitrogen take four ring aromatic character. Several structures have one or two thiophenic sulfur groups. The homologous series containing benzopyrene cores x-class 0) includes benzo(a)pyrene, a potent carcinogen.

Sulfide Molecules

Figure 40:
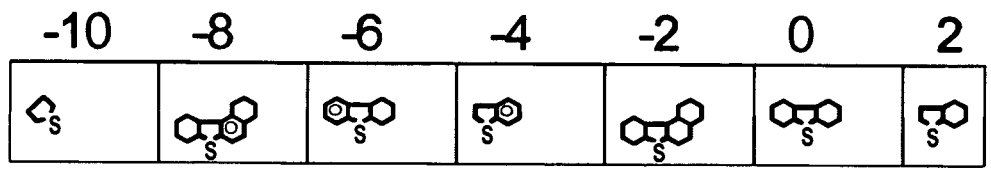
FIG. 40 shows sulfide cores.

Sulfide molecules contain aliphatic sulfur, but they have neither oxygen nor nitrogen. The cores shown in FIG. 40 have x-classes that take the even integers −10, −8, −6, −4, −2, 0, 2. Preferred structures are in bold. Alkyl sulfides x-class −8), and benzyl sulfides x-class −2) are not preferred because they are rare in petroleum. Sulfide cores in the model-of-composition have either one or aliphatic sulfur groups. Some of these cores contain only aliphatic carbon; others contain both aliphatic and aromatic carbon.

Polar Molecules

Figure 41:
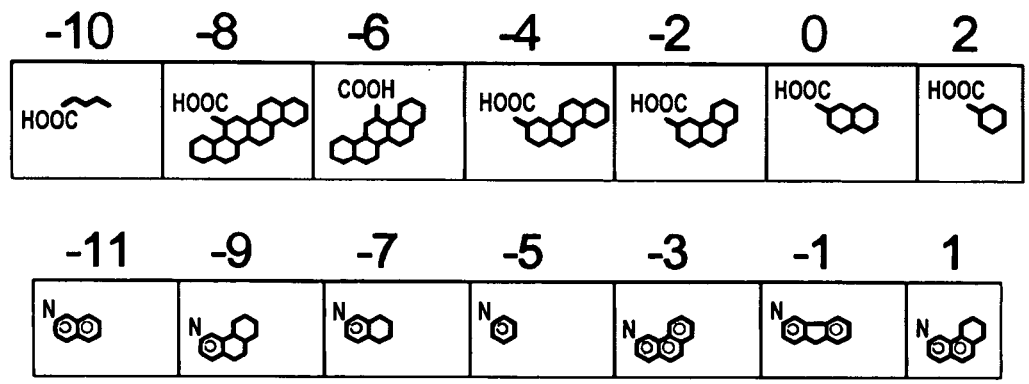
FIG. 41 shows polar cores.

Polar cores shown in FIG. 41 are organized into even X-class acids (−10, −8, −6, −4, −2, 0, 2), and odd X-class basic nitrogen molecules (−11, −9, −7, −5, −3, −1, 1). Some of the acid cores included in the model-of-composition contain aliphatic sulfur. Other polar oxygenates, e.g. alcohols and sulfoxides (not shown) are less abundant in petroleum than are acids, and do not appear in the model-of-composition. All odd x-class cores contain one basic nitrogen group.

Olefins and Thiophenes

Figure 42:
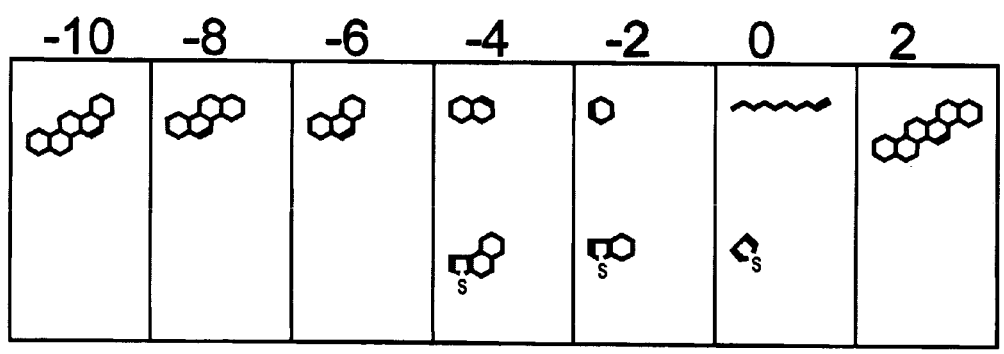
FIG. 42 shows olefin and thiophene cores.

Olefin and thiophene cores shown in FIG. 42 have x-classes that take the even integers −10, −8, −6, −4, −2, 0, 2. Olefin and thiophene cores appear in FIG. 66; preferred structures are in bold. We have added a double bond to each of the preferred saturate cores (see structures of FIG. 35) to create the olefin cores in the top row of FIG. 42. The formation of each double bond present in an olefin requires the removal of two hydrogen atoms. Thus, the X-class of each of these mono-olefin cores is two less than that of the corresponding saturates core. Similarly, we could removed two hydrogen atoms from each of selected 1 ring aromatic cores (see FIG. 36, and from 2 ring aromatic cores (see FIG. 37) to create olefin cores. Thiophenes (see second row of FIG. 42) are created by removing four hydrogen atoms from tetrahydrothiophene cores (see FIG. 40). Olefin cores containing more than one double bond, e.g. diolefins, are not preferred in the model-of-composition. Such molecules tend to be highly reactive and are therefore rare in petroleum.

Appendix B: Analysis of Petroleum

Figure 43:
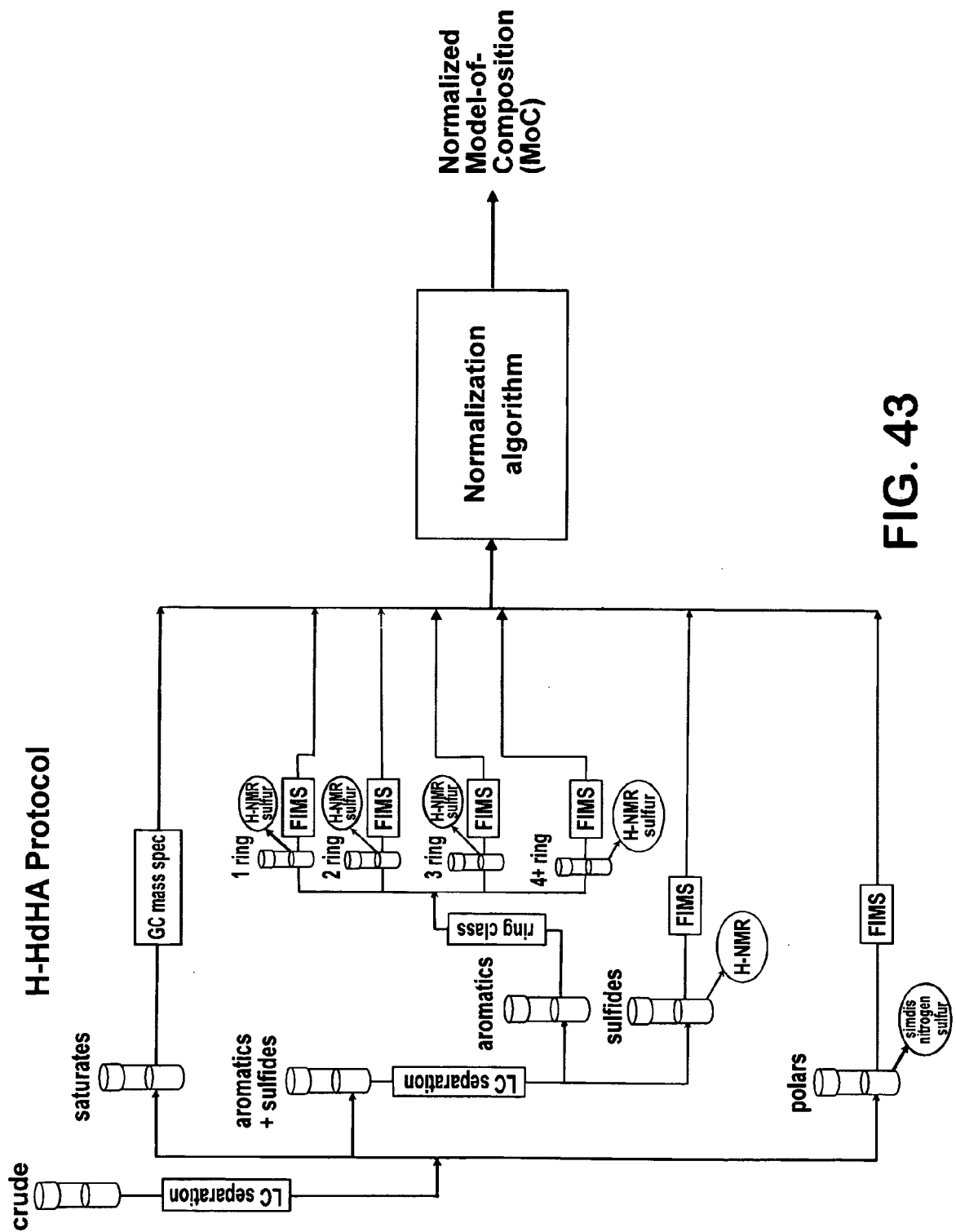
FIG. 43 shows an example of an analytical scheme for measuring the MOC of a vacuum gas oil.

The petroleum industry analyzes complex hydrocarbon mixtures using a wide variety of techniques. In this appendix, we focus attention on analytical techniques that enable us to build models-of-composition (see summary in Table B1). We discuss these techniques in a protocol that is consistent with the model-of-composition's organization and structure discussed above. A diagram of the analytical protocol for a petroleum gasoil appears in FIG. 43.

Liquid Chromatography (LC)

Multiple liquid chromatography (LC) separations comprise the first steps in the analytical protocol (see FIG. 67). The sample is separated into saturate, aromatic, sulfide, and polar fractions in the first LC separation step. Here, the sample is dissolved in a solvent and added to two stacked LC columns consisting of silica gel or other suitable agent. Neither column retains the saturate fraction, which is collected first. The first column retains the aromatics and polars fractions. The second column retains the sulfide fraction. The aromatic fraction is eluted from the silica gel column by injecting a suitable solvent. The polars is eluted by methanol. The sulfide fraction is eluted from the second column with a mixture of methanol and toluene. In the second LC separation step, the aromatic fraction is further separated into ring class fractions (1, 2, 3, and 4+). If significant olefins are present, a fifth fraction containing olefins and thiophenes is also collected.

The LC separations described above allow us to material balance the model-of-composition according to molecular groups discussed above. Also, we analyze each fraction collected from these separations with techniques described below.

Analyzing Saturate Fractions

We analyze saturate fractions with gas chromatography (GC) combined with miss spectrometry (GC/MS) to measure distributions of molecules by molecular weight (and x-class) by boiling point. In saturate molecules, x-class identifies the number of naphthenic rings per molecule (see FIG. 58). Thus, GC combined with GC/MS measures distributions of total paraffins, and of naphthenes by ring class. The mass spectrometer used in the GC/MS technique operates in electron impact (EI) mode. In this measurement, certain naphthenes and paraffins produce ion fragments of indistinguishable mass. In gasoil samples, we analyze only the saturate fraction by SFC (see FIG. 43). In other samples where LC separation is infeasible, we analyze the total sample by SFC to material balance the sample according to the major molecular groups (see Table B1).

TABLE B1

Analytical Protocol for a Petroleum Gasoil

| Technique or Property Type | Technique | Output | Total | Saturate | Aromatic | Aromatic Ring class 1 | 2 | 3 | 4 | Sulfide | Polar | Olefins/Thiophenes |
|---|---|---|---|---|---|---|---|---|---|---|---|---|
| Chromatography | Liquid Chromatography (LC) | Fraction samples and material balance | X | | X | | | | | | | |
| | Supercritical Fluid Chromatography (SFC) | Fraction material balance | X | X | | | | | | | | |
| | GC | n-paraffin distribution | | X | | | | | | | | |
| Mass spectroscopy (MS) | GC/MS | Molecular weight, X-class distributions by boiling point | | X | | | | | | | | |
| | FIMS | Molecular weight, X-class distributions | | | | X | X | X | X | X | X | X |
| | ESI-MS | Molecular weight, X-class distributions | | | | | | | | | X | |
| Nuclear Magnetic Resonance (NMR) | H-NMR | Proton chemical shift | | X | | X | X | X | X | | | X |
| | C13-NMR | Carbon chemical shift | | X | | | | | | | | |
| Elemental Properties | Sulfur | Sulfur by X-ray spectroscopy, wt % | X | | X | X | X | X | X | X | X | X |
| | Nitrogen | Nitrogen by chemiluminescence, ppm | X | | | | | | | | | |
| | Basic Nitrogen | Basic nitrogen by titration, ppm | X | | | | | | | | | |

All normal (n-) paraffins in the total sample are collected in the saturate fraction. The boiling points of n-paraffins are well known and are readily identified by GC. Similarly, we identify mono-methyl paraffins by a proprietary GC analysis technique. Multi-branched paraffins are x-class 2 saturate molecules other than normal and mono-methyl paraffins. Nuclear magnetic resonance (NMR) measures the chemical shifts of hydrogen (H-NMR) or carbon atoms (C13-NMR) with respect to their bonding environments. In saturate molecules, H-NMR counts the fraction of hydrogen atoms in methyl vs. methylene groups. Thus, NMR reveals the average degree of branching per molecule (other than n-paraffins) in the saturate fraction.

Analyzing Aromatic and Ring Class Fractions

Aromatic and ring class fractions prepared by LC separation contain sulfur and nitrogen, unlike the saturate fraction. We therefore subject aromatic and ring class fractions to an analytical protocol that differs from that of saturate fractions (see FIG. 57).

We measure the sulfur content of the aromatic fraction, and of the ring class fractions by X-ray spectrometry (see FIG. 67, Table B1). Nitrogen in aromatic molecules is non-basic, and is concentrated in the 4+ ring class fraction. Basic nitrogen is concentrated in the polar fraction. Unlike sulfur, which occurs in weight percent quantities in petroleum, nitrogen is often at ppm levels. Due to nitrogen's lower abundance relative to sulfur, we do not attempt to measure nitrogen content of aromatics or ring class fractions. Instead, we measure the total sample's nitrogen content by chemiluminescence, and basic nitrogen content by titration (see Table B1).

The analytical protocol for aromatic ring class fractions includes measurements other than sulfur content (see FIG. 67). We measure the molecular weight (and x-class) distributions of each aromatic ring class fraction by field-emission mass spectroscopy (FIMS). The FIMS technique generates strong ion currents from aromatic molecules with minimal ion fragmentation, unlike EI-MS used in saturate fraction GC/MS analysis (see above). Because FIMS measures x-class distributions, the technique can distinguish between even x-class molecules, and odd x-class molecules present in the 4+ ring class fraction (see FIG. 43). $^1$H-NMR counts the fraction of protons in methyl groups, methylene groups, and in aromatic rings within each ring class fraction. For samples where olefinic molecules co-elute with ring class fractions prepared by LC, H-NMR also counts the fraction of protons in olefinic bonds. In ring class 3 and 4+ fractions, $^1$H-NMR also counts the fraction of protons in bay regions.

Analyzing Sulfide Fractions

Sulfide fractions are analyzed using a subset of measurements typically performed on ring class fractions (see Table B1). We measure total sulfur content of the sulfide fraction. We also measure the distribution of molecular weights (and x-class) by FIMS.

Analyzing Polar Fractions

The polar fraction analysis protocol is similar to that of the sulfide fraction. Again, we measure the sulfur content of the polar fraction. Also, we measure the molecular weight distribution of even x-class molecules, and of odd x-class basic nitrogen molecules (see polar cores in FIG. 65) using FIMS. In recent years., we have found that electrospray ionization mass spectrometry (ESI-MS) improves our ability to discriminate polar molecules by x-class relative to FIMS (see Qian, K., K. E. Edwards, J. H. Diehl, and L. A. Green, "Fundamentals and Applications of Electrospray Mass Spectrometry for Petroleum Characterization", Energy & Fuels, v. 18, pp. 1784-1791, 2004.).

In samples containing more than 0.5 wt % olefins and thiophenes, a LC fraction containing olefins and thiophenes is recovered (not shown in FIG. 67). We analyze these fractions with a protocol identical to that of the ring class fractions: sulfur measurement, molecular weight (and x-class) distribution by FIMS, and proton chemical shift by H-NMR.

Appendix C: Normalizing Analytical Protocols to the Model-of-Composition

Once we have analyzed a gasoil sample by the protocol described in Appendix B, the model-of-composition must be reconciled to all measurements in the analytical protocol. In particular, the model-of-composition must reproduce all measurements in the analytical protocol as closely as possible, and at the same time satisfy a set of property balances, e.g. mass and elemental composition. We call this reconciliation procedure normalization. The mathematics of normalization is a constrained optimization problem: we optimize the model-of-composition's fidelity to the test results of the analytical protocol subject to the property balance constraints. The model-of-composition's purpose in refinery process modeling is to convey detailed information about molecular abundance into and out of refinery process models. The analytical test results are sources of molecular abundance information. When we optimize the model-of-composition's fidelity to these test results, we minimize the total amount of information lost by forcing the model-of-composition to satisfy property balances.

In order to quantify this lost information, we must express the model-of-composition as a distribution function over composition space. Composition space is the list of molecular lumps contained in a model-of-composition (see Appendix A). The distribution function is the abundance of each molecular lump $\{w_i\}$, where the index $i=1, 2, \ldots, N$, the total number of molecular lumps is N, and the units of the abundance $w_i$ are in weight percent for convenience.

Assume the normalized model-of-composition has a distribution function $\{w_i\}$, and the reference model-of-composition has a distribution function $\{w_i^*>\}$ that exactly matches the results of selected analytical tests detailed in Appendix A. The amount of information we lose by normalizing the reference model-of-composition equals the Shannon mutual information entropy, I, defined by Cover and Thomas:

$$I = \sum_{i=1}^{N} w_i * \ln(w_i / w_i^*). \quad (C1)$$

The properties we force the model-of-composition to balance include mass, e.g. total sample weight, LC or SFC fraction weights (see Table B1). These properties also include elemental composition e.g. sulfur, nitrogen content, weight or mole percent total hydrogen, or hydrogen of prescribed chemical shift, etc. These properties are constant for each molecular lump. Therefore, the property balance constraints are linear in the weight percents $\{w_i\}$ $$\sum_{i=1}^{N} a_{ji} w_i = b_j \text{ for } j = 1, 2, \ldots, NP \quad (C2)$$

where $a_{ji}$ is the density of property j in molecular lump i, $b_j$ is the sample's measured value of property j, and NP is the number of properties to be balanced.

Normalization Algorithm

To minimize the amount of lost information defined in Equation (C1), subject to the property balance constraints in Equation (C2), we use the method of Lagrangian multipliers (see e.g. Denn, M. M. "Optimization by Variational Methods", Chapter 1, McGraw-Hill, NYC, 1969.). In this method, we seek the stationary solution of the Lagrangian L $$L \equiv \sum_{i=1}^{N} w_i * \ln(w_i / w_i^*) + \sum_{j=1}^{NP} \lambda_j \left( b_j - \sum_{i=1}^{N} a_{ji} w_j \right) \quad (C3)$$

that satisfies $$\frac{\delta L}{\delta w} = 0, \frac{\partial L}{\partial \lambda_j} = 0 \text{ for } j = 1, \ldots, NP$$

where $\lambda_j$ is the Lagrangian multiplier of the j-th property balance constraint Equation (C2). From $\partial L/\partial \lambda_j = 0$ we recover the constraint Equations (C2). We evaluate the functional derivative $\delta L/\delta w$ using calculus of variations (see e.g. Davis, H. T., "Statistical Mechanics of Phases, Interphases and Thin Films", Chapter 12, VCH Publishers, 1996.). For the Lagrangian in Equation (C3), the stationary solution is $$w_i = w_i^* * \exp\left(-1 + \sum_{j=1}^{NP} a_{ji} \lambda_j\right) \text{ for } i = 1, \ldots, N \quad (C4)$$

Next, we substitute the stationary solution (C4) into the constraint Equations (C2) and eliminate the unknown weight percents $\{w_i\}$:

$$\sum_{i=1}^{N} a_{ji} w_i^* * \exp\left(-1 + \sum_{k=1}^{NP} \lambda_k a_{ki}\right) = b_j \quad (C5)$$

$$\text{for } j = 1, \ldots, NP$$

The number of molecular lumps, N, can be several thousand in a model-of-composition. Meanwhile, the number of properties we use to normalize the model-of-composition, NP, is of order 10-100, i.e. the optimization problem described in Equations (C1-C5) is under-constrained. Newton's method solution of the nonlinear equation system (C5) for the Lagrangian multipliers $\{\lambda_k\}$ is rapid, even for large N. In model-of-composition normalization, the constraint matrix $\alpha$ can be sparse. We save additional computing time by exploiting this sparsity in the algorithm. Once we have solved the equation system (C5) for these Lagrangian multipliers, we substitute them into the stationary solution (C4) and obtain the weight percents of the normalized model-of-composition $\{w_i\}$.

After we have solved the nonlinear equation system (C5), the normalized weight percents $\{w_i\}$ obtained from Equation (C4) satisfy the property balance Equations (C2) to machine precision. In reality, the measured value of each property, $b_j$, has uncertainty due to measurement error. Where measurement errors are significant, the property balances (C2) should be "soft" constraints. To accommodate soft constraints in the normalization algorithm, we have heuristically modified Equation (C5) to read $$\sum_{i=1}^{N} a_{ji} w_i * \exp\left(-1 + \sum_{k=1}^{NP} \lambda_k a_{ki}\right) = b_j \exp(-f_j \lambda_j) \quad (C6)$$

for $j = 1, \ldots, NP$ where the softness parameter $f_j > 0$ for soft constraints, and $f_j = 0$ for hard constraints.

Reference Model-of-Composition

The analytical test results we use to set the reference weights $\{w_i^*\}$ in a gasoil's model-of-composition are summarized in Table C1. Each molecular lump in the model-of-composition is of known molecular weight (and x-class). Hence, it is natural to make the reference weights $\{w_i^*\}$ consistent with mass spectra where available. We make the reference weights of naphthenes and paraffins consistent with the GC/MS spectrum measured on the saturate fraction. The reference weights of molecular lumps in aromatic ring class fractions and sulfides fractions are made consistent with FIMS spectra measured on each fraction. In polar fractions, we use FIMS, or ESI-MS spectra if available. Normal and monomethyl paraffin reference weights equal those measured by GC. We make the reference weights of multi-branched paraffin molecular lumps consistent with the difference between GC/MS and GC results. Because the reference weights arise from MS and GC analysis of each LC fraction, we normalize each mass spectrum to its measured LC weight, so that the reference weights $\{w_i^*\}$ sum to the LC fraction weights, and to 100 wt % over the entire sample.

At present, mass spectrometry methods used in model-of-composition development are capable of measuring only nominal masses (and x-class). In all LC fractions detailed in Section 2, and in most of the x-classes in each fraction, more than one molecular structure shares the same nominal molecular weight. Therefore, we must decide how to partition each mass signal among multiple structures. In the absence of other information, we partition each mass signal equally among preferred structures. Less preferred structures are assigned reference weights of 0.1% of the mass signal or less.

Property Balance Constraints in Model-of-Composition Normalization

The property balance constraints we enforce in the normalization algorithm (Equations C4, C6) are summarized in Table C2. Properties we balance include total sample weight (100 wt %), LC fraction weights, sulfur contents of each LC fraction (except for the saturate fraction), as well as total and basic nitrogen content of the entire sample. We also balance olefinic hydrogen content in ring class fractions, and bay region hydrogen content in the 3 and 4+ ring class fractions, as measured by H-NMR. We have also assigned a softness parameter $f_j$ to each property balance constraint (see Table C2). Their values are assigned heuristically to be consistent with each measured property's repeatability.

During normalization, we balance certain properties by methods other than adjusting reference weights of molecular lumps in the algorithm detailed above. H-NMR chemical shifts reveal the average branching and methylation of selected LC fractions, as noted above. We balance these properties to the model of composition by adding appropriate numbers of branches and methyl groups to each molecular lump within the LC fraction after completing the algorithm detailed in Equations C4 and C6.

TABLE C1

Analytical Test Results Used to Set Reference Weight Distributions In the Model-of-Composition

| Analytical Test | Results | Fractions |
|---|---|---|
| GC | Wt % n-paraffins by carbon number | saturates |
| GC/MS | Wt % molecules by molecular weight and x-class | saturates |
| SFC | Wt % Total paraffins, naphthenes | saturates |
| LC | Wt % of LC fractions | all |
| FIMS | Wt % molecules by molecular weight and x-class | aromatic ring classes 1-4+, sulfides, polars |
| ESI-MS | Wt % molecules by molecular weight and x-class | polars |

TABLE C2

Property Balance Constraints in Model-of-Composition Normalization

| Property value, b | Softness parameter, f | Property density, $a_{ji}$ |
|---|---|---|
| Total weight (100 wt %) | 0 | $a_i = 1$ for all molecules i |
| LC fraction wt % | 1.0E−09 | $a_{ji} = 1$ for all molecules i in fraction j<br>$a_{ji} = 0$ otherwise. |
| Wt % sulfur in LC fraction, total sample basis. | 1.0E−08 | $a_{ji}$ = weight fraction sulfur of molecule i in fraction j<br>$a_{ji} = 0$ otherwise. |
| Wt % olefinic protons in LC fraction, total sample basis. | 1.0E−03 | $a_{ji}$ = weight fraction olefinic protons of molecule i in fraction j<br>$a_{ji} = 0$ otherwise. |
| Wt % bay region protons in aromatic ring class 3, 4+ fractions, total sample basis. | 1.0E−03 | $a_{ji}$ = weight fraction bay region protons of molecule i in fraction j.<br>$a_{ji} = 0$ otherwise. |
| Average number of branches, methyl groups per molecule in each LC fraction. | N/A | N/A |

Appendix D: Optimization of Weights

When the multivariate analytical data such as FT-IR is augmented with other property data such as API gravity, viscosity, SimDis and sulfur, the relative importance of these data relative to the multivariate data must be adjusted so as to provide reference blends that yield the best estimate of composition. In particular, the adjustable parameter $\alpha$ in [3] must be set for each property and property combination, i.e. the optimum value of $\alpha$ for weighting API gravity when augmenting FT-IR with API Gravity alone will typically be similar, but not identical to the optimum value of $\alpha$ for weighting API gravity when FT-IR is augmented with API Gravity, SimDis and Sulfur.

Optimization of the $\alpha$ parameters requires an estimate of the quality of the reference blends that are produced. Such an estimate is typically obtained using cross-validation of the reference library. Each sample in the library (e.g. the multivariate data such as FT-IR and corresponding property data such as API gravity, SimDis and sulfur) is removed from the library and treated as an unknown, being analyzed using the remaining samples in the library. A blend is calculated using the methodology of this invention, and a reference HDHA composition is calculated as the same blend of the HDHAs of the reference samples. The estimated HDHA is then compared to the measured HDHA for that sample to produce a measure of quality of the estimated reference. The sample is returned to the library, and the process is repeated for another other sample in the library until each sample has been left out and analyzed once.

The quality of the estimated reference can be quantified using statistics such as the correlation coefficient (cc) or the Euclidean distance (d). If h is the measured HDHA vector (with element $h_i$), and $\hat{h}$ is the corresponding estimated HDHA vector, then the correlation coefficient cc is given by $$cc = \frac{n\sum_{i=1}^{n} h_i \hat{h}_i - \sum_{i=1}^{n} h_i \sum_{i=1}^{n} \hat{h}_i}{\sqrt{\left[n\sum_{i=1}^{n} h_i^2 - \left(\sum_{i=1}^{n} h_i\right)^2\right]\left[n\sum_{i=1}^{n} \hat{h}_i^2 - \left(\sum_{i=1}^{n} \hat{h}_i\right)^2\right]}} \quad [D1]$$

and d is given by $$d = \sqrt{\sum_{i=1}^{n} (\hat{h}_i - h_i)^2} \quad [D2]$$

An optimization (fitness) function is constructed as a combination of the cc or d for the samples in the library, and is minimized using standard optimization techniques such as the Simplex Method.

Optimization of α based on the cross-validation results can be difficult due to the presence of relatively unique samples in the library. When these relatively unique samples are left out and analyzed during cross-validation, there is insufficient information left in the library to generate accurate predictions, and the resultant large errors tend to dominate most fitness functions.

To address this difficulty, the following optimization approach was developed. The Fast NonNegative Least Squares (FNNLS) algorithm used in VA and VIC was employed to do a leave-one-out cross-validation analysis of the reference HDHA data, i.e. predicting a reference HDHA based on a linear combination of the other reference HDHAs in the library. The correlation coefficient ($cc_{HDHA}$) and distanced ($d_{HDHA}$) between these estimated HDHAs and the measured HDHAs were calculated and taken to represent the best possible answer that could be obtained given this set of references. No linear combination of references obtained from this invention could match (in a least squares sense) the measured HDHA better than these results. The correlation coefficients ($cc_{TI}$) and distances ($d_{TI}$) were calculated between the HDHAs estimated using this invention, and the measured HDHAs. Fitness functions of form shown in [D3] and [D4] can used to calculate weightings, α, for API, SimDis or Sulfur, when used alone or in combination.

$$f_{cc} = \sum_{i=1}^{n} \left(\frac{cc_{HDHA} - cc_{TI}}{cc_{HDHA}}\right)^2 \quad [D3]$$

$$f_d = \sum_{i=1}^{n} \left(\frac{d_{TI} - d_{HDHA}}{d_{HDHA}}\right)^2 \quad [D4]$$

Very similar results were obtained using the correlation coefficient and distance based functions. Other fitness functions based on cc and d or other similar similarity measures can also be used in optimizing α. Table D1 shows typical weight values used in the libraries of Examples 3-7.

Separate optimizations were performed for IR augmented with one inspection (API Gravity, SimDis or Sulfur) using [7]. Weights, α, calculated from these optimizations were used as starting points for optimization using pairs of inspections, or using all three inspections.

TABLE D1

Example of Weights, α, for Library from Examples 3-7

| Property | Property Used Individually | | | Property Used Together |
|---|---|---|---|---|
| | Weight | Weight | Weight | Weights |
| API Gravity | 51.0489 | — | — | 64.6619 |
| SimDis | — | 44.6596 | — | 47.3509 |
| Sulfur | — | — | 60.2162 | 17.1682 |

Property Correlations:

In composition-based modeling, a generic scalar stream property P assumes a simple blending rule between wt % abundances, $W_i$ and property densities of each molecular lump, $p_i$. Examples of these blending rules include:

linear:

$$P = \sum_{i=1}^{N} p_i W_i$$

harmonic:

$$100/P = \sum_{i=1}^{N} W_i / p_i$$

log-linear:

$$\ln P = \sum_{i=1}^{N} (W_i/100) \ln p_i$$

where wt % abundances of molecular lumps in a stream sum to 100%. Distributed properties, e.g. boiling point distributions, are computed by re-ordering molecular lump indices such that the property density, e.g. molecular lump's boiling point in a complex mixture, is monotonically increasing, i.e.:

$$\text{cumulative wt \% off }(BP_j) = \sum_{k=1}^{j} W_k BP_k$$

where the molecular lump indices are ordered such that $BP_{k-1} < BP_k < BP_{k+1}$ for all k=2, 3, ... N−1

The property density of molecular lump i, $p_i$ is often assumed to vary smoothly between molecular lumps in the same homologous series, e.g.

$$p_i = a_m + b_m/MW_i + c_m br_i + d_m me_i/MW_i$$

where $a_m$, $b_m$, $c_m$, $d_m$ are constants chosen for the homologous series m containing molecular lump i, $MW_i$ is the molecular weight of lump i, and $b_{ri}$, $me_i$ are the respective branching and methylation indices of molecular lump i. As molecular weight increases from the lowest molecular weight feasible in a homologous series, property densities predicted from the above correlation change at a decreasing rate to a high molecular weight asymptote. This trend has been observed in analyses of pure-component properties such as specific gravity and normal boiling point of many organic compounds organized by homologous series.

What is claimed is:

1. A method for determining the composition of a material comprising:
   a) using a computer to construct an initial estimate of composition of a material by:
      acquiring multivariate analytical data of the material, and
      fitting the multivariate analytical data of the material to a combination of multivariate analytical data in a database to determine coefficients of the combination so as to determine a reference model of composition based on the coefficients and the compositions in the database, wherein said database includes multivariate analytical data of database materials whose compositions are known, wherein fitting multivariate analytical data of the material includes augmenting said multivariate analytical data with property data to form augmented data, said augmented data being fit as a combination of multivariate analytical data augmented with property data of the database materials, and
   b) using said computer to refine the determined reference model of composition by reconciling the acquired multivariate analytical data to the determined reference model of composition, defined by the determined coefficients of the combination, by adjusting the determined reference model of composition to match a set of known additional analytical properties, wherein the reconciling of the reference model of composition comprises using an optimization algorithm with said computer, whereby the determined reference model of composition is modified into a detailed model of composition to match the set of the known additional analytical properties,
   wherein said reference model of composition includes a combination of molecular lumps having a determined fraction or percent for each of the molecular lumps, wherein said reconciling the reference model of composition reconciles the lump fractions or percents to property targets.

2. The method of claim 1 wherein said property data includes at least one property data selected from the group consisting of API gravity, density, sulfur content, nitrogen content, aliphatic sulfur content, basic nitrogen content, fraction or percent distilled, boiling point temperature and simulated distillation or combinations thereof.

3. The method of claim 1 wherein said reconciling the reference model of composition is carried out by successive substitution.

4. The method of claim 1 wherein said reconciling the reference model of composition is carried out by constrained optimization.

5. The method of claim 1 wherein said reconciling the reference model of composition is carried out by constrained optimization of an information entropy of the fractions of the molecular lumps.

6. The method of claim 1 wherein said reconciling the reference model of composition is carried out by constrained optimization such that property targets can be expressed as a set of linear and/or nonlinear algebraic constraint equations.

7. The method of claim 1, wherein the property targets are scalar property targets and/or distributed property targets, wherein said reconciling the reference model of composition uses scalar property targets and/or distributed property targets.

8. The method of claim 7 wherein said scalar property targets include density or API Gravity.

9. The method of claim 7 wherein said scalar property targets include elemental composition.

10. The method of claim 7 wherein said scalar property targets include sulfur content.

11. The method of claim 7 wherein said scalar property targets include nitrogen content.

12. The method of claim 7 wherein said scalar property targets include aliphatic sulfur content.

13. The method of claim 7 wherein said distributed property targets include the fraction or percent distilled with boiling point temperature.

14. The method of claim 7 wherein said distributed property targets include the density or API gravity as a function of boiling point temperature.

15. The method of claim 7 wherein said distributed property targets include elemental composition of the material as a function of boiling point temperature.

16. The method of claim 7 wherein said distributed property targets include sulfur content of the material as a function of boiling point temperature.

17. The method of claim 7 wherein said distributed property targets include nitrogen content of the material as a function of boiling point temperature.

18. The method of claim 1 wherein said reconciling the reference model of composition is carried out by successive substitution such that property targets are outputs of any numerical algorithm that includes the model of composition as inputs.

19. The method of claim 1 wherein said property targets include functions of the adsorption spectrum of electromagnetic radiation of the material.

20. The method of claim 1 wherein said property targets include integrals over a specified range of chemical shift spectra arising from nuclear magnetic resonance (NMR) analysis of the material.

21. The method of claim 1, wherein said multivariate analytical data include infrared spectra.

22. The method of claim 2 wherein said property data include density and/or API gravity.

23. The method of claim 2 wherein said property data include fraction or percent distilled with boiling point temperature.

24. The method of claim 2 wherein said property data include sulfur content.

* * * * *